United States Patent
Mieher et al.

(10) Patent No.: US 7,379,183 B2
(45) Date of Patent: *May 27, 2008

(54) APPARATUS AND METHODS FOR DETECTING OVERLAY ERRORS USING SCATTEROMETRY

(75) Inventors: Walter D. Mieher, Los Gatos, CA (US); Ady Levy, Sunnyvale, CA (US); Boris Golovanesky, Haifa (IL); Michael Friedmann, Mountain View, CA (US); Ian Smith, Los Gatos, CA (US); Michael E. Adel, Zichron Ya'akov (IL); Christopher F. Bevis, Los Gatos, CA (US); Paola Dececco, Redwood City, CA (US); John Fielden, Los Altos, CA (US); Noah Bareket, Saratoga, CA (US); Kenneth P. Gross, San Carlos, CA (US); Mark Ghinovker, Migdal Ha'Emek (IL)

(73) Assignee: KLA-Tencor Technologies Corp., Milpitas, CA (US)

( * ) Notice: Subject to any disclaimer, the term of this patent is extended or adjusted under 35 U.S.C. 154(b) by 305 days.

This patent is subject to a terminal disclaimer.

(21) Appl. No.: 10/785,731

(22) Filed: Feb. 23, 2004

(65) Prior Publication Data

US 2004/0233442 A1      Nov. 25, 2004

Related U.S. Application Data

(63) Continuation-in-part of application No. 10/729,838, filed on Dec. 5, 2003.

(60) Provisional application No. 60/504,093, filed on Sep. 19, 2003, provisional application No. 60/498,524, filed on Aug. 27, 2003, provisional application No. 60/449,496, filed on Feb. 22, 2003.

(51) Int. Cl.
G01B 11/00  (2006.01)
G01B 11/02  (2006.01)
G01J 4/00   (2006.01)
G01N 21/55  (2006.01)

(52) U.S. Cl. .................. 356/401; 356/369; 356/445; 356/508

(58) Field of Classification Search ............... None
See application file for complete search history.

(56) References Cited

U.S. PATENT DOCUMENTS 3,594,085 A * 7/1971 Wilmanns ............... 356/365

(Continued)

FOREIGN PATENT DOCUMENTS

EP        1400855        3/2004

(Continued)

OTHER PUBLICATIONS

TDB, "Mask Overlay Determination," IBM Technical Disclosure Bulletin, Dec. 1978, pp. 2772-2773. www.delphion.com.*

*Primary Examiner*—Layla G. Lauchman
*Assistant Examiner*—Gordon J. Stock, Jr.
(74) *Attorney, Agent, or Firm*—Weaver Austin Villeneuve & Sampson LLP

(57) ABSTRACT

Disclosed is a method of determining an overlay error between two layers of a multiple layer sample. For a plurality of periodic targets that each have a first structure formed from a first layer and a second structure formed from a second layer of the sample, an optical system is employed to thereby measure an optical signal from each of the periodic targets. There are predefined offsets between the first and second structures. An overlay error is determined between the first and second structures by analyzing the measured optical signals from the periodic targets using a scatterometry overlay technique based on the predefined offsets.

44 Claims, 24 Drawing Sheets

U.S. PATENT DOCUMENTS

| | | | |
|---|---|---|---|
| 4,103,998 A | 8/1978 | Nakazawa et al. | 356/152 |
| 4,167,337 A | 9/1979 | Jaerisch et al. | 356/354 |
| 4,200,395 A | 4/1980 | Smith et al. | 356/356 |
| 4,332,473 A | 6/1982 | Ono | 356/356 |
| 4,631,416 A | 12/1986 | Trutna, Jr. | 250/548 |
| 4,647,207 A * | 3/1987 | Bjork et al. | 356/369 |
| 4,703,434 A | 10/1987 | Brunner | 364/488 |
| 4,710,642 A * | 12/1987 | McNeil | 250/559.04 |
| 4,750,836 A | 6/1988 | Stein | 356/399 |
| 4,757,207 A | 7/1988 | Chappelow et al. | 250/491.1 |
| 4,818,110 A | 4/1989 | Davidson | 356/358 |
| 4,820,055 A | 4/1989 | Muller | 356/401 |
| 4,828,392 A | 5/1989 | Nomura et al. | 356/401 |
| 4,848,911 A | 7/1989 | Uchida et al. | 356/356 |
| 4,929,083 A | 5/1990 | Brunner | 356/400 |
| 4,999,014 A | 3/1991 | Gold et al. | 356/382 |
| 5,112,129 A | 5/1992 | Davidson et al. | 356/359 |
| 5,114,235 A | 5/1992 | Suda et al. | 356/401 |
| 5,166,752 A | 11/1992 | Spanier et al. | 356/369 |
| 5,172,190 A | 12/1992 | Kaiser | 356/401 |
| 5,182,455 A | 1/1993 | Muraki | 250/548 |
| 5,182,610 A | 1/1993 | Shibata | 356/349 |
| 5,189,494 A | 2/1993 | Muraki | 356/401 |
| 5,191,393 A | 3/1993 | Hignette et al. | |
| 5,276,337 A * | 1/1994 | Starikov | 250/548 |
| 5,316,984 A | 5/1994 | Leourx | 437/250 |
| 5,327,221 A | 7/1994 | Saitoh et al. | 356/355 |
| 5,340,992 A | 8/1994 | Matsugu et al. | 250/548 |
| 5,343,292 A | 8/1994 | Brueck et al. | 356/363 |
| 5,355,306 A | 10/1994 | Waldo | |
| 5,388,909 A | 2/1995 | Johnson et al. | |
| 5,414,514 A | 5/1995 | Smith et al. | 356/363 |
| 5,416,588 A * | 5/1995 | Ducharme et al. | 356/369 |
| 5,465,148 A | 11/1995 | Matsumoto et al. | 356/349 |
| 5,525,840 A | 6/1996 | Tominaga | 257/797 |
| 5,596,406 A | 1/1997 | Rosencwaig et al. | 356/327 |
| 5,596,413 A | 1/1997 | Stanton et al. | 356/401 |
| 5,608,526 A | 3/1997 | Pinwonka-Corle et al. | 356/369 |
| 5,666,196 A | 9/1997 | Ishii et al. | 356/356 |
| 5,712,707 A | 1/1998 | Ausschnitt et al. | 356/401 |
| 5,783,342 A | 7/1998 | Yamashita et al. | 430/30 |
| 5,801,390 A | 9/1998 | Shiraishi | 250/559.3 |
| 5,805,290 A | 9/1998 | Ausschnitt et al. | |
| 5,808,742 A | 9/1998 | Everett et al. | 356/363 |
| 5,883,710 A | 3/1999 | Nikoonahad et al. | 356/237.2 |
| 5,889,593 A | 3/1999 | Bareket | 356/445 |
| 5,909,333 A | 6/1999 | Best et al. | 360/51 |
| 5,912,983 A | 6/1999 | Hiratsuka | 382/144 |
| 5,923,041 A | 7/1999 | Cresswell et al. | 250/491.1 |
| 5,966,201 A | 10/1999 | Shiraishi et al. | |
| 6,013,355 A | 1/2000 | Chen et al. | 428/209 |
| 6,023,338 A | 2/2000 | Bareket | 356/401 |
| 6,046,094 A | 4/2000 | Jost et al. | 438/400 |
| 6,077,756 A | 6/2000 | Lin et al. | 438/401 |
| 6,079,256 A | 6/2000 | Bareket | 73/105 |
| 6,081,325 A | 6/2000 | Leslie et al. | 356/327 |
| 6,128,089 A | 10/2000 | Ausschnitt et al. | 356/401 |
| 6,153,886 A | 11/2000 | Hagiwara et al. | 250/548 |
| 6,160,622 A | 12/2000 | Dirksen et al. | 356/401 |
| 6,165,656 A | 12/2000 | Tomimatu | 430/22 |
| 6,177,330 B1 | 1/2001 | Yasuda | 438/401 |
| 6,197,679 B1 | 3/2001 | Hattori | 438/636 |
| 6,255,189 B1 | 7/2001 | Muller et al. | 438/401 |
| 6,323,560 B1 | 11/2001 | Narimatsu et al. | 257/798 |
| 6,342,735 B1 | 1/2002 | Colelli et al. | 257/797 |
| 6,350,548 B1 | 2/2002 | Leidy et al. | 430/22 |
| 6,420,791 B1 | 7/2002 | Huang et al. | 257/797 |
| 6,420,971 B1 | 7/2002 | Leck et al. | 340/542 |
| 6,421,124 B1 | 7/2002 | Matsumoto et al. | 356/401 |
| 6,445,453 B1 * | 9/2002 | Hill | 356/450 |
| 6,458,605 B1 | 10/2002 | Stirton | |
| 6,462,818 B1 | 10/2002 | Bareket | 356/401 |
| 6,476,920 B1 | 11/2002 | Scheiner et al. | 356/630 |
| 6,486,954 B1 | 11/2002 | Mieher et al. | 356/401 |
| 6,522,406 B1 | 2/2003 | Rovira et al. | 356/369 |
| 6,590,656 B2 | 7/2003 | Xu et al. | 356/369 |
| 6,611,330 B2 | 8/2003 | Lee et al. | 356/369 |
| 6,633,831 B2 | 10/2003 | Nikoonahad et al. | 702/155 |
| 6,699,624 B2 * | 3/2004 | Niu et al. | 430/5 |
| 6,713,753 B1 | 3/2004 | Rovira et al. | |
| 6,767,680 B2 | 7/2004 | Schulz | |
| 6,772,084 B2 | 8/2004 | Bischoff et al. | |
| 6,813,034 B2 | 11/2004 | Rosencwaig et al. | |
| 6,815,232 B2 * | 11/2004 | Jones et al. | 438/14 |
| 6,819,426 B2 * | 11/2004 | Sezginer et al. | 356/401 |
| 6,867,870 B1 * | 3/2005 | Mihaylov et al. | 356/601 |
| 6,888,632 B2 | 5/2005 | Smith | |
| 6,900,892 B2 | 5/2005 | Shchegrov et al. | |
| 6,919,964 B2 | 7/2005 | Chu | |
| 6,949,462 B1 | 9/2005 | Yang et al. | |
| 6,982,793 B1 * | 1/2006 | Yang et al. | 356/401 |
| 6,992,764 B1 | 1/2006 | Yang et al. | |
| 7,042,569 B2 | 5/2006 | Sezginer et al. | |
| 7,046,361 B1 | 5/2006 | Yang et al. | |
| 7,046,376 B2 * | 5/2006 | Sezginer | 356/601 |
| 7,061,615 B1 | 6/2006 | Lowe-Webb | |
| 7,061,627 B2 | 6/2006 | Opsal et al. | |
| 7,080,330 B1 | 7/2006 | Choo et al. | |
| 7,242,477 B2 * | 7/2007 | Mieher et al. | 356/401 |
| 7,280,212 B2 * | 10/2007 | Mieher et al. | 356/401 |
| 7,289,213 B2 * | 10/2007 | Mieher et al. | 356/401 |
| 7,298,481 B2 * | 11/2007 | Mieher et al. | 356/401 |
| 7,301,634 B2 * | 11/2007 | Mieher et al. | 356/401 |
| 2002/0054290 A1 | 5/2002 | Vurens et al. | 356/369 |
| 2002/0072001 A1 | 6/2002 | Brown et al. | 430/30 |
| 2002/0093648 A1 | 7/2002 | Nikoonahad et al. | |
| 2002/0135875 A1 | 9/2002 | Niu et al. | 359/564 |
| 2002/0149782 A1 | 10/2002 | Raymond | 356/616 |
| 2002/0158193 A1 | 10/2002 | Sezginer et al. | 250/237 |
| 2002/0192577 A1 | 12/2002 | Fay et al. | 430/22 |
| 2003/0002043 A1 | 1/2003 | Abdulhalim et al. | 356/400 |
| 2003/0011786 A1 | 1/2003 | Levy et al. | 356/600 |
| 2003/0020184 A1 | 1/2003 | Ballarin | 257/797 |
| 2003/0156276 A1 | 8/2003 | Bowes | 356/124 |
| 2003/0223630 A1 | 12/2003 | Adel et al. | 382/145 |
| 2004/0129900 A1 | 7/2004 | Den Boef et al. | |
| 2005/0012928 A1 | 1/2005 | Sezginer et al. | |
| 2005/0122516 A1 * | 6/2005 | Sezginer et al. | 356/401 |
| 2005/0157297 A1 | 7/2005 | Abdulhalim et al. | |
| 2005/0286051 A1 | 12/2005 | Sezginer et al. | |
| 2006/0193630 A1 * | 8/2006 | Dishon et al. | 396/611 |

FOREIGN PATENT DOCUMENTS

| | | |
|---|---|---|
| JP | 63-248804 | 10/1988 |
| JP | 11-86332 | 3/1999 |
| JP | 60-126881 | 7/2006 |
| WO | WO/85/04266 | 9/1985 |
| WO | WO/95/02200 | 1/1995 |
| WO | WO 99/45340 | 9/1999 |
| WO | WO/9956174 | 11/1999 |
| WO | WO01/84382 | 11/2001 |
| WO | WO 01/97279 | 12/2001 |
| WO | WO/0215238 | 2/2002 |
| WO | WO02/25708 | 3/2002 |
| WO | WO 02/25723 | 3/2002 |
| WO | WO/0218871 | 3/2002 |
| WO | WO 02/35300 | 5/2002 |
| WO | WO 0250509 | 6/2002 |
| WO | WO 02/065545 | 8/2002 |
| WO | WO02/65545 A2 | 8/2002 |
| WO | WO02/069390 A2 | 9/2002 |
| WO | WO 02/084213 | 10/2002 |
| WO | WO02/084213 A1 | 10/2002 |

| | | |
|---|---|---|
| WO | WO 03/001297 | 1/2003 |
| WO | WO03042629 | 5/2003 |
| WO | WO/03054475 | 7/2003 |

OTHER PUBLICATIONS

Kim, Young-Chang et al., "Automatic In-Situ Focus Monitor Using Line Shortening Effect," Journal: Proceedings of the SPIE, vol. 3677, pt. 1-2, pp. 184-193.*

Sherman, Enrique R., "Characterization and Monitoring of Variable NA and Variable Coherence Capable Photo Steppers Utilizing the Phase Shift Focus Monitor Reticle," Journal: Proceedings of the SPIE, vol. 2439, pp. 61-69.*

Bischoff, Jorg et al., "Modeling of Optical Scatterometry with Finite-Number-of-Periods Grating," Journal: Proceedings of the SPIE, vol. 3743, pp. 41-48.*

Uchida, Norio et al., "A Mask to Wafer Alignment and Gap Setting Method for X-Ray Lithography Using Gratings," Journal: Journal of Vacuum Science & Technology B, vol. 9, No. 6, pp. 3202-3206.*

Ina, Hidecki et al., "Alignment Mark Optimization to Reduce Tool and Wafer-induced Shift to XTRA-1000," Japanese Journal of Applied Physics, vol. 38, No. 12B, pp. 7065-7070.*

Baumbach, T. et al., "Grazing Incidence Diffraction by Laterally Patterned Semiconductor Nanostructures," Journal: Journal of Physics, vol. 32, No. 6, pp. 726-740.*

TDB, "Phase-Sensitive Overlay Analysis Spectrometry," IBM Technical Disclosure Bulletin, Mar. 1990. pp. 170-174 www.delphion.com.

TDB, "Interferometric Method of Checking the Overlay Accuracy in Photolitho Graphic Exposure Processes." IBM Technical Disclosure Bulletin, Mar. 1990. pp. 214-217. www.delphion.com.

TDB, "Interferometric Measurement System for Overlay Measurement in Lithographic Processes", Feb. 1994, pp. 535-536.

Sang-Man Bae, et al., "Performance of New Overlay Measurement Mark," 424/SPIE vol. 2725.

V.I. Arkipov, "Kinetics of the Diffraction Efficiency of Light-Induced Dynamic Gratings in Layers of Disordered Semiconductors", Moscow Engineering-Physics Institute Submitted Feb. 14, 1992; Quantum Electron Nov. 1993. 1994 American Institute of Physics.

Joseph C. Pellegrini, et al., "Super Sparse Overlay Sampling Plans: An Evaluation of Methods and Algorithms for Optimizing Overlay Quality Control and Metrology Tool Throughput", SPIE vol. 3677-0277-786X.

V.C. Jaiprakash and C. J. Gould, Comparison Optical, SEM, and AFM Overlay Measurement, SPIE vol. 3677-0277-786X.

Ya V. Fattakhov, "Formation of Periodic Diffraction Structures at Semiconductor Surfaces for Studying the Dynamics of Photoinduced Phase Transitions", 0030-400X/00/8901-0136.

D.G. Papazoglou, et al., "Photorefractive Optical Properties of Volume Phase Gratings Induced in Sillenite Crystals, When the Grating Vector Lies on the 111 plane," Appl. Phys. B 71, 841-848 (2000).

Kenneth W. Tobin, et al. "Automatic Classification of Spatial Signatures on Semiconductor Wafermaps," SEMATECH, Austin, Texas. SPIE vol. 3050.

Bharath Rangarajan, et al., Optimal Sampling Strategies for sub-100 nm Overlay, APD Lithography, Advanced Micro Devices Inc., Sunnyvale, CA, Department of Chemical Engineering, Michigan State Univeristy, East Lansing, MI, SPIE vol. 3332.

R.C. Herbert, "Width and Overlay Narrow Kerf Test Site", IBM TDB, Apr. 1978, vol. 20 No. 11A. IBM Corp.

Auzino, L., "A New Technique for Multiple Overlay Check", Abstract. First Search: Detailed Record, Terms & Conditions 1992-2003. Copyright, 1998, IEE.

H.J. Levinson, et al., "Minimization of Total Overlay Errors on Product Wafers Using an Advanced Optimization Scheme" Abstract. First Search:Detailed Record. Terms & Conditions 1992-2003. Copyright 1998, IEEE.

K. Kodate, et al. "Towards the Optimal Design of Binary Optical Elements with Different Phase Levels Using a Method of Phase Mismatch Correction," Abtract. FirstSearch: Detailed Record. Copyright 2001, IEE.

Klienknecht, H.P., "Diffraction and Interference Optics for Monitoring Fine Dimensions in Device Manufacture", Copyright 1984 The Institute of Physics. Inst. Phys. Conf. Ser. No. 69. Paper presented at ESSDERC/SSSDT 1983, Canterbury Sep. 13-16, 1983.

Office Action dated May 18, 2007, received in U.S. Appl. No. 10/729,838.

European Search Report dated Jul. 26, 2007, from related European Application No. 04713795.5.

Supplemental European Search Report dated Jul. 26, 2007, from related European Application No. 03796723.9.

Office Action mailed on Oct. 30, 2007, from related U.S. Appl. No. 10/785,396.

* cited by examiner

Fig. 2(a) With Offsets F and no Overlay Error

Fig. 2(c) With Offsets F+ f0 and no Overlay Error

Fig. 2(e) With Offsets F+ f0 and Overlay Error E

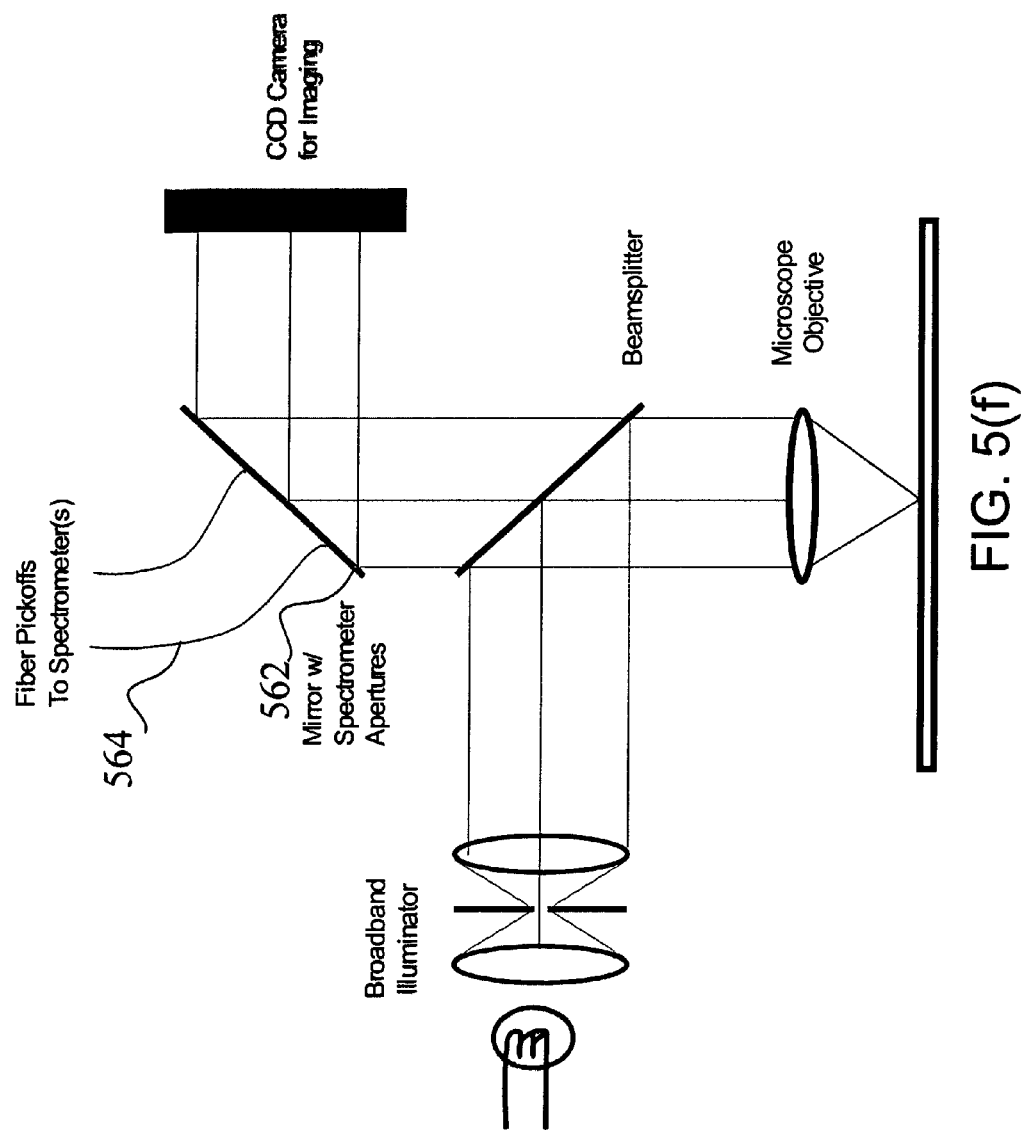

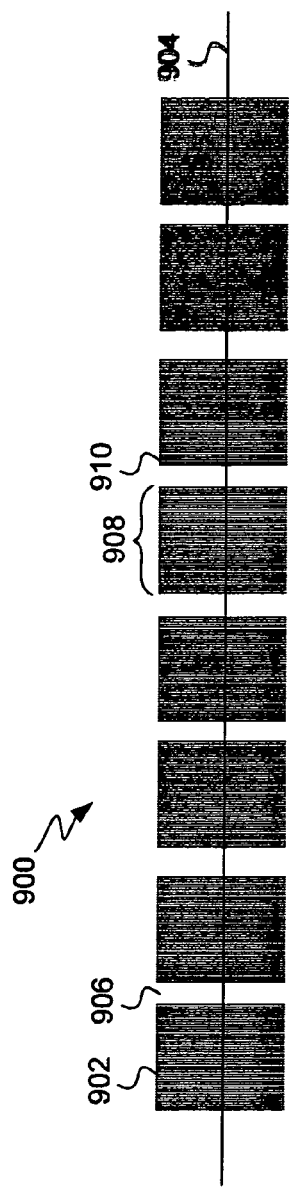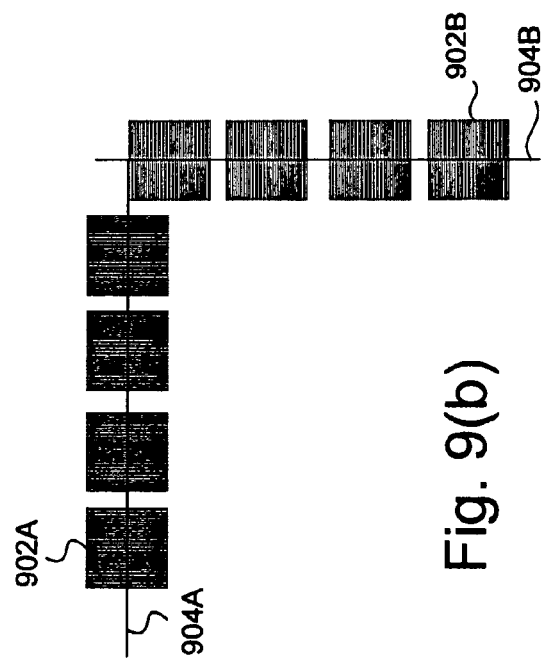
Fig. 9(a)
Fig. 9(b)

APPARATUS AND METHODS FOR DETECTING OVERLAY ERRORS USING SCATTEROMETRY

CROSS REFERENCE TO RELATED PATENT APPLICATION

This application claims priority of the following co-pending U.S. Provisional Patent Applications: (1) Application No. 60/504,093, entitled APPARATUS AND METHODS FOR DETECTING OVERLAY ERRORS USING SCATTEROMETRY, by Walter D. Mieher, filed 19 Sep. 2003, (2) Application No. 60/449,496, entitled METHOD AND SYSTEM FOR DETERMINING OVERLAY ERRORS BASED ON SCATTEROMETRY SIGNALS ACQUIRED FROM MULTIPLE OVERLAY MEASUREMENT PATTERNS, by Walter D. Mieher, filed 22 Feb. 2003, and (3) Application No. 60/498,524, filed 27 Aug. 2003, entitled "METHOD AND APPARATUS COMBINING IMAGING AND SCATTEROMETRY FOR OVERLAY METROLOGY", by Mike Adel.

This application is also a continuation-in-part of U.S. application Ser. No. 10/729,838, by Walter D. Mieher et al. filed 5 Dec. 2003. These applications are herein incorporated by reference in their entirety.

BACKGROUND OF THE INVENTION

The present invention relates to determination of overlay between structures formed in single or multiple layers. More particularly, it relates to determining overlay based on diffraction of radiation interacting with such structures.

In various manufacturing and production environments, there is a need to control alignment between various layers of samples, or within particular layers of such samples. For example, in the semiconductor manufacturing industry, electronic devices may be produced by fabricating a series of layers on a substrate, some or all of the layers including various structures. The relative position of such structures both within particular layers and with respect to structures in other layers is relevant or even critical to the performance of completed electronic devices.

The relative position of structures within such a sample is sometimes called overlay. Various technology and processes for measuring overlay have been developed and employed with varying degrees of success. More recently, various efforts have been focused on utilizing radiation scatterometry as a basis for overlay metrology.

Certain existing approaches to determining overlay from scatterometry measurements concentrate on comparison of the measured spectra to calculated theoretical spectra based on model shape profiles, overlay, and film stack, and material optical properties (n,k dispersion curves), or comparison to a reference signal from a calibration wafer.

Existing approaches have several associated disadvantages. For example, a relatively large number of parameters must be included in the profile, overlay, and film modeling to accurately determine the overlay. For example, in some approaches using simple trapezoidal models for both the upper and lower layer profiles, the minimum number of pattern parameters that must be included is seven, including overlay. If film thicknesses variation is included in the model, the number of parameters increases correspondingly. A large number of parameters could require increased processing resources, may introduce corresponding errors, and may delay the results, thereby possibly decreasing throughput and increasing inefficiencies and costs. For example, comparison of a measured spectrum to calculated reference spectra takes longer with more parameters, whether a library-based approach is used or a regression approach is used.

Another disadvantage of certain existing approaches to determination of overlay based on scatterometry is the detailed knowledge of the film stack, film materials, and pattern element profiles that may be required to determine accurate theoretical spectra to compare to the measured spectra.

Yet another disadvantage of certain existing approaches to determination of overlay based on scatterometry is the accurate knowledge of the scatterometry optical system that may be required to determine accurate theoretical spectra to compare to the measured spectra.

Therefore, in light of the deficiencies of existing approaches to determination of overlay based on scatterometry, there is a need for improved systems and methods for determination of overlay based on scatterometry.

SUMMARY OF THE INVENTION

Accordingly, mechanisms are provided for determining overlay error between two layers of a sample using improved scatterometry overlay techniques. In one embodiment, the scatterometry technique includes linear based techniques for determining overlay which can be performed without utilization of calibration data (e.g., generated from models or from calibration test wafers). In another implementation, a scatterometry technique is accomplished using a phase based approach. The phase based approach may also be practiced without using calibration data. Additionally, several specific improvements for implementing scatterometry techniques (e.g., linear or phase based) are disclosed. These improved scatterometry technique implementations may be performed separately or combined together in any manner. Uses of such overlay error, as well as novel targets from which to determine overlay using scatterometry overlay techniques, are also disclosed.

In one embodiment, a method for determining an overlay error between at least two layers in a multiple layer sample is disclosed. An imaging optical system is used to measure a plurality of measured optical signals from a plurality of periodic targets on the sample. The targets each have a first structure in a first layer and a second structure in a second layer, and there are predefined offsets between the first and second structures. The imaging optical system is configured to have an illumination and/or collection numerical aperture (NA) and/or spectral band selected so that only a $0^{th}$ diffraction order is collected and measured for the plurality of measured optical signals. A scatterometry overlay technique is then used to analyze the measured optical signals of the periodic targets and the predefined offsets of the first and second structures of the periodic targets to thereby determine an overlay error between the first and second structures of the periodic targets.

In another method embodiment for determining an overlay error between at least two layers in a multiple layer sample, a plurality of periodic targets that each have a first structure in a first layer and a second structure in a second layer, wherein there are predefined offsets between the first and second structures, are provided. The method includes (a) using an optical system having a broadband source for generating an optical incident beam having multiple wavelengths, a detector for detecting a measured signal from the sample in response to the incident beam and a filter for selectively passing particular one or more wavelengths of the output signal to the detector, directing at least one radiation beam towards each target to measure a plurality of measured signals from the periodic targets while adjusting the filter so as to pass a particular one or more wavelengths of the measured signals through the filter towards the detector in the form of a plurality filtered signals; and (b) using a scatterometry overlay technique to analyze the filtered signals of the periodic targets and the predefined offsets of the first and second structures of the periodic targets to thereby determine an overlay error between the first and second structures of the periodic targets.

In another method embodiment, a plurality of optical signals are measured at a plurality of incident angles for each of a plurality of periodic targets target that each have a first structure formed from a first layer and a second structure formed from a second layer of the sample. There are predefined offsets between the first and second structures. An overlay error is then determined between the first and second structures by analyzing the measured optical signals at the plurality of incident angles from the periodic targets using a scatterometry overlay technique based on the predefined offsets without using a calibration operation.

In yet another method embodiment, a first optical signal is measured using a first ellipsometer or a first reflectometer and a second optical signal is measured using a second ellipsometer or a second reflectometer for each of a plurality of periodic targets that each have a first structure formed from a first layer and a second structure formed from a second layer of the sample. In this embodiment, there are also predefined offsets between the first and second structures. The overlay error between the first and second structures is then determined by analyzing the measured first and second optical signals from the periodic targets using a scatterometry overlay technique based on the predefined offsets.

In another method approach, for a plurality of periodic targets that each have a first structure formed from a first layer and a second structure formed from a second layer of the sample, an interferometer is imployed to modulate substantially a plurality of wavelengths of a broadband source. One or more images of the periodic targets are then acquired. There are predefined offsets between the first and second structures. An overlay error is then determined between the first and second structures by analyzing the one or more acquired images from the periodic targets using a scatterometry overlay technique based on the predefined offsets.

In another scatterometry overly technique, an optical system having a tunable laser is employed at a plurality of settings for a plurality of periodic targets that each have a first structure formed from a first layer and a second structure formed from a second layer of the sample. A plurality of optical signals are then measured at the plurality of tunable laser settings for each of the periodic targets. There are predefined offsets between the first and second structures. An overlay error is then determined between the first and second structures by analyzing the measured optical signals from the periodic targets using a scatterometry overlay technique based on the predefined offsets.

In another scatterometry overlay embodiment, an optical system having a spatial filter for selectively filtering an optical signal measured is employed to thereby measure an optical signal from each of a plurality of periodic targets that each have a first structure formed from a first layer and a second structure formed from a second layer of a sample while spatially filtering at least a portion of at least one of the measured optical signals. There are predefined offsets between the first and second structures. An overlay error is then determined between the first and second structures by analyzing the measured optical signals from the periodic targets using a scatterometry overlay technique based on the predefined offsets.

In another scatterometry overlay method, a plurality of periodic targets that each have a first structure in a first layer and a second structure in a second layer are provided. There are predefined offsets between the first and second structures. An ellipsometer having a polarization modulator is used to measure a plurality of measured signals from the periodic targets. A scatterometry overlay technique is then used to analyze the measured signals of the periodic targets and the predefined offsets of the first and second structures of the periodic targets to thereby determine an overlay error between the first and second structures of the periodic targets.

In another embodiment, a plurality of theoretical scatterometry signals are generated for a plurality of target configurations and/or process conditions and/or overlay errors configurations using a model or calibrated data. The plurality of theoretical scatterometry signals and their associated target configurations and/or process conditions and/or overlay errors are stored. For each of a plurality of measured periodic targets that each have a first structure formed from a first layer and a second structure formed from a second layer of the sample, an optical signal is measured. There are predefined offsets between the first and second structures. A measured overlay error is measured between the first and second structures by analyzing the measured optical signals at the plurality of incident angles from the periodic targets using a scatterometry overlay technique based on the predefined offsets without using a calibration operation. The measured scatterometry signal is compared with the stored measured scatterometry signals to obtain a characteristic of the measured periodic targets or process condition for such measured periodic targets based on a substantially matching theoretical overlay value.

In one scatterometry overlay embodiment, any combination of the following instruments may be used to measure optical signals for a plurality of periodic targets that each have a first structure formed from a first layer and a second structure formed from a second layer of the sample, wherein there are predefined offsets between the first and second structures:

an imaging reflectometer, an imaging spectroscopic reflectometer, a polarized spectroscopic imaging reflectometer, a scanning reflectometer system, a system with two or more reflectometers capable of parallel data acquisition, a system with two or more spectroscopic reflectometers capable of parallel data acquisition, a system with two or more polarized spectroscopic reflectometers capable of parallel data acquisition, a system with two or more polarized spectroscopic reflectometers capable of serial data acquisition without moving the wafer stage or moving any optical elements or the reflectometer stage, imaging spectrometers, imaging system with wavelength filter, imaging system with long-pass wavelength filter, imaging system with short-pass wavelength filter, imaging system without wavelength filter, interferometric imaging system, imaging ellipsometer, imaging spectroscopic ellipsometer, a scanning ellipsometer system, a system with two or more ellipsometers capable of parallel data acquisition, a system with two or more ellipsometers capable of serial data acquisition without moving the wafer stage or moving any optical elements or the ellipsometer stage, a Michelson interferometer, and a Mach-Zehnder interferometer, a Sagnac interferometer, a scanning angle of incidence system, a scanning azimuth angle system. An overlay error is then determined between the first and second structures by analyzing the measured optical signals from the periodic targets using a scatterometry overlay technique based on the predefined offsets.

In another embodiment, a spectroscopic ellipsometer is employed to thereby measure an optical signal from each of a plurality of periodic targets that each have a first structure formed from a first layer and a second structure formed from a second layer of the sample. There are predefined offsets between the first and second structures. An overlay error between the first and second structures is then determined by analyzing the measured optical signals from the periodic targets using a scatterometry overlay technique based on the predefined offset. In another aspect, a laser ellipsometer having a photoelastic modulator is employed instead to measure the optical signals.

In yet another implementation, an optical system is used to measure a plurality of measured optical signals from a plurality of periodic targets on the sample. The periodic targets each have a first structure in a first layer and a second structure in a second layer, and there are predefined offsets between the first and second structures. The periodic targets are arranged in same x or y direction. A scatterometry overlay technique is then used to analyze the measured optical signals of the periodic targets and the predefined offsets of the first and second structures of the periodic targets to thereby determine an overlay error between the first and second structures of the periodic targets.

In another implementation, the method for determining overlay includes (a) using an optical system to measure a plurality of measured optical signals from a plurality of periodic targets on the sample, wherein the periodic targets each have a first structure in a first layer and a second structure in a second layer, wherein there are predefined offsets between the first and second structures, wherein the optical signals are measured at a same focus setting of the optical system without refocusing; and (b) using a scatterometry overlay technique to analyze the measured optical signals of the periodic targets and the predefined offsets of the first and second structures of the periodic targets to thereby determine an overlay error between the first and second structures of the periodic targets. In another embodiment, the measured optical signals are each in the form of a line image and not necessarily a same focus setting.

In another implementation of a scatterometry overlay technique, an optical system is used to measure a plurality of measured optical signals from a plurality of periodic targets that each have a first structure formed from a first layer and a second structure formed from a second layer on the sample. Each first and second structure of each target are designed to have a predefined offset with respect to each other. A scatterometry overlay technique is used to analyze the measured optical signals of the periodic targets and the predefined offsets of the first and second structures of the periodic targets to thereby determine a first overlay error between the first and second structures of the periodic targets. A model based technique is also used to analyze the measured optical signals of the periodic targets to thereby determine a second overlay error between the first and second structures of the periodic targets.

In another implementation, a sample having a plurality of periodic targets that each have a first structure in a first layer and a second structure in a second layer is provided. There are predefined offsets between the first and second structures. Using scatterometry overlay metrology, scatterometry overlay data is obtained from a first set of the periodic targets based on one or more measured optical signals from the first target set on the sample. Using an imaging overlay metrology, imaging overlay data is obtained from a second set of the periodic targets based on one or more image(s) from the second target set on the sample.

In another embodiment, the invention pertains to a method for aligning an imprint lithography mask with a semiconductor wafer. The method includes (a) aligning a plurality of periodic alignment marks of the mask with a plurality of alignment marks on the wafer; (b) using an optical system to measure a plurality of measured optical signals from a plurality of the periodic alignment marks on the mask and on the wafer, wherein the periodic alignment marks each have a first structure in a first layer and a second structure in a second layer, wherein there are predefined offsets between the first and second structures; (c) using a scatterometry overlay technique to analyze the measured optical signals of the periodic alignment marks and the predefined offsets of the first and second structures of the periodic alignment marks to thereby determine an overlay error or mask registration error between the mask and the wafer; and (d) repeating operations (a) through (c) until the overlay error or mask registration error equals a predetermined offset or is within a predetermined range of mask misregistration values.

In another implementation, a combined scatterometry mark is disclosed. The mark includes a scatterometry critical dimension (CD) or profile target capable of being measured to determine CD or profile information and a scatterometry overlay target disposed over the scatterometry CD or profile target, the scatterometry overlay target cooperating with the scatterometry CD or profile target to form a scatterometry mark capable of being measured to determine overlay. In another aspect, the invention pertains to a single metrology tool that includes a scatterometry overlay measurement system configured to measure overlay; and a CD-SEM system configured to measure critical dimension. In another embodiment, the invention pertains to a method of producing a combined critical dimension and overlay mark. A CD target is formed in a first layer of a sample, and an overlay target is formed in a second layer of the sample, the overlay target being formed over the CD target. In yet another embodiment, the invention pertains to a method for determining CD in one layer and an overlay error between at least two layers in a multiple layer sample. The method includes performing scatterometry measurements on a CD target in order to determine CD, the CD target being formed in a first layer of the sample, and performing scatterometry measurements on an overlay mark in order to determine overlay error, the overlay mark comprising an overlay target formed in a second layer of the sample and the CD target formed in the first layer of the sample, the overlay target being disposed over the CD target.

In yet another implementation, a scatterometry mark configured for determining overlay error is disclosed. The mark includes (a) a plurality of periodic targets that each have structures on a first and second layer, wherein there are predefined offsets between the first and second structures so that overlay error between the first and second structures may be determined by analyzing a plurality of measured optical signals from each target; and (b) a plurality of targets that each have third structures on a third layer that is underneath the first and second layer, wherein the third structures are perpendicular to the first and second structures. In an alternative embodiment, a target structure for measuring overlay between a second periodic structure and a third periodic structure are both disposed above a first line grating where the first grating is oriented in a first direction and the second and third periodic structure are oriented in a second direction, the second direction being substantially orthogonal to the first direction. In another aspect, a method of determining overlay error includes measuring the target structure described above with a scatterometry overlay technique to determine overlay error between the second and third periodic structures.

These and other features and advantages of the present invention will be presented in more detail in the following specification of the invention and the accompanying figures which illustrate by way of example the principles of the invention.

BRIEF DESCRIPTION OF THE DRAWINGS

FIG. 2(a) is a side view illustration of a patterned top layer L2 being offset by an amount +F from a patterned bottom layer L1 in accordance with one embodiment of the present invention.

FIG. 2(c) is a side view illustration of a patterned top layer L2 being offset by an amount +F+f0 from a patterned bottom layer L1 in accordance with one embodiment of the present invention.

FIG. 2(e) is a side view illustration of a patterned top layer L2 being offset by an amount +F+f0+E from a patterned bottom layer L1 in accordance with one embodiment of the present invention.

FIG. 5(f) is a diagrammatic representation of a fixed, discrete channel optical system in accordance with a fifth embodiment of the present invention.

FIG. 9(a) shows a plurality of targets placed substantially-collinearly along either an X-direction or a Y-direction, wherein in this example half of the targets are placed so as to measure overlay in the x direction and half of the targets are placed so as to measure overlay in the y direction, in accordance with a first embodiment of the present invention.

FIG. 9(b) shows four targets disposed collinearly along the X-dimension, and four targets disposed collinearly along the Y-dimension in accordance with a second embodiment of the present invention.

DETAILED DESCRIPTION OF SPECIFIC EMBODIMENTS

Figure 1:
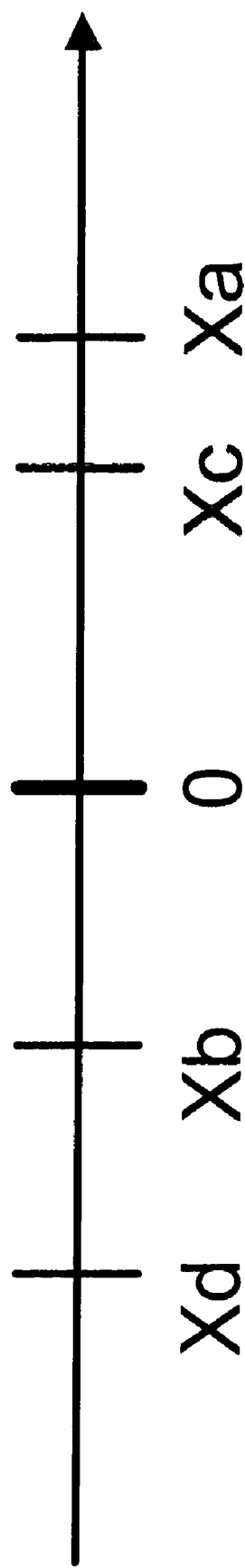
FIG. 1 illustrates the relative distribution of designed overlay offsets Xa, Xb, Xc, and Xd for corresponding interlayer patterns (overlay targets) A, B, C, and D according to an embodiment of the present invention.

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

In general, the present invention provides techniques for determining overlay based on scatterometry measurements of any number of scatterometry overlay (SCOL) targets. One implementation of a scatterometry technique which is referred to herein as the "linear approach" will first be described. Alternative scatterometry approaches, such as a "phase approach" are also described. Finally, a number of scatterometry based improvements will then be described. Although these improvements are mainly described in relation to the linear scatterometry approach, these scatterometry improvements may be implemented using any other suitable scatterometry technique or approach such as the phase approach described herein. Additionally, although only certain specific combinations of improvements are described herein as being implemented together, any number of the improvements described herein may be combined and implemented together.

An aspect of the present invention provides a set of four scatterometry overlay targets (although in other embodiments more or less than four may be used) which have been formed on a sample or workpiece, such as a semiconductor device. A pattern could also be described as a "pattern or interlayer pattern", with the two terms being synonymous under most circumstances. In a particular implementation, the sample has two or more layers of a semiconductor device, and the targets are utilized to provide a measure of the placement accuracy of various structures comprised in the device. Commonly, placement accuracy is characterized by measurement of an overlay error between two different layers of the semiconductor device. More generally, overlay error can be measured between two different patterns generated by different pattern exposure steps.

In a specific embodiment, a set of four targets are provided, and each target includes two sets of structures on two different layers which are offset from each other. In a specific implementation, an offset may be defined as the sum or the difference of two separate distances: a first distance F and a second distance f0, with F being greater than f0. Denoting the four targets as "target A", "target B", "target C" and "target D", the corresponding predetermined offsets for each of these targets may be defined as follows for a specific target design:

$Xa = +F + f0$ (for target $A$), $Xb = -F + f0$ (for target $B$), $Xc = +F - f0$ (for target $C$), and $Xd = -F - f0$ (for target $D$).

The offsets for Xa through Xd may be any suitable value for practicing the techniques of the present invention so as to determine overlay. For example, Xa and Xb may have different values of f0 than Xc and Xd.

FIG. 1 illustrates the distribution of offsets Xa, Xb, Xc and Xd along the x axis in a particular implementation of the invention. As shown, offsets Xa and Xc are both positive with Xa being larger than Xc. In contrast, offsets Xb and Xd are both negative with Xd being more negative than Xb. The offsets may be defined from a position in the unit cell of the first structure. If a symmetry position exists in the unit cell, it may be preferable to define the offsets from the symmetry position. Alternatively, the offsets may be defined from a position in the unit cell of the second structure but care should be taken to agree with the convention of overlay measurements being defined as the position of the L2 pattern (or second exposed pattern) measured with respect to the position of the L1 pattern (or second exposed pattern).

The number of targets and the magnitude and sense of their corresponding offsets may be chosen in any suitable manner so that the techniques of the present invention may be practiced to determine overlay error. A specific set of targets and their corresponding offsets are described below in relation to FIGS. 2(a) through 2(f). It should be readily apparent that there are numerous combinations of targets and offset values which may be utilized to practice the techniques and utilize the systems of the present invention.

FIG. 2(a) is a side view illustration of a patterned top layer L2 being offset by an amount F from a patterned bottom layer L1 in accordance with one embodiment of the present invention. Each layer L1 and L2 is patterned into a set of structures. A structure may include any suitable feature, such as a line, trench or a contact. A structure may be designed to be similar to a semiconductor device feature. A structure may also be formed from a combination of different features. Further, a structure may be located on any layer of the sample, e.g., either above the top layer of the sample, within any layer of the sample, or partially or completely within a layer of the sample. In the illustrated embodiment of FIG. 2(a), layer L1 includes the complete structures 204a-c, while layer L2 includes the complete structures 202a-c. Construction of scatterometry overlay targets structures and methods for producing them are described in U.S. patent application, having application Ser. No. 09/833,084, filed 10 Apr. 2001, entitled "PERIODIC PATTERNS AND TECHNIQUE TO CONTROL MISALIGNMENT", by Abdulhalim, et al., which application is herein incorporated by reference in its entirety.

As shown, the structures of the top layer L2 are offset by an amount F from the structures of the bottom layer L1. The structures of the two offset layers may be located within adjacent layers or have any suitable number and types of layers disposed in between the two offset layers. FIG. 2(a) also shows three films T1, T2, and T3 between patterned layers L1 and L2 and their corresponding structures. To the extent that any other layers exist between the two layers having the structures, these other layers exhibit at least a minimum degree of transmission for electromagnetic radiation to permit propagation of the radiation between the layers having the structures.

Figure 2B:
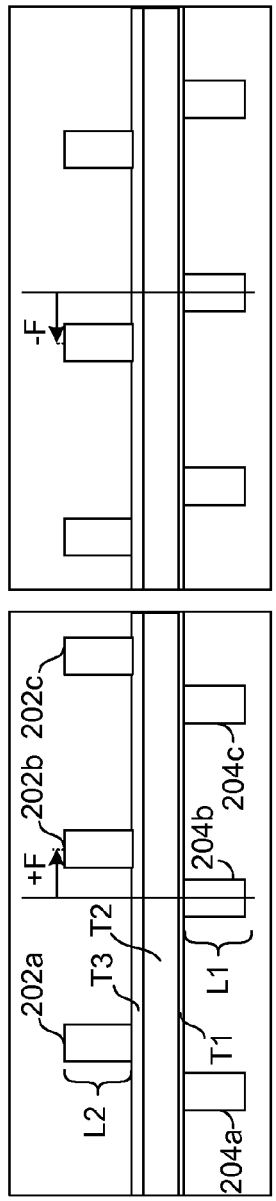
FIG. 2(b) is a side view illustration of a patterned top layer L2 being offset by an amount −F from a patterned bottom layer L1 in accordance with one embodiment of the present invention.
Figure 2D:
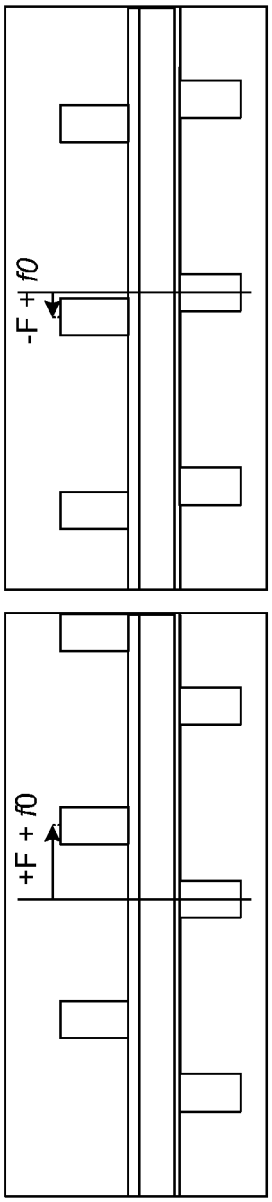
FIG. 2(d) is a side view illustration of a patterned top layer L2 being offset by an amount −F+f0 from a patterned bottom layer L1 in accordance with one embodiment of the present invention.
Figure 2F:
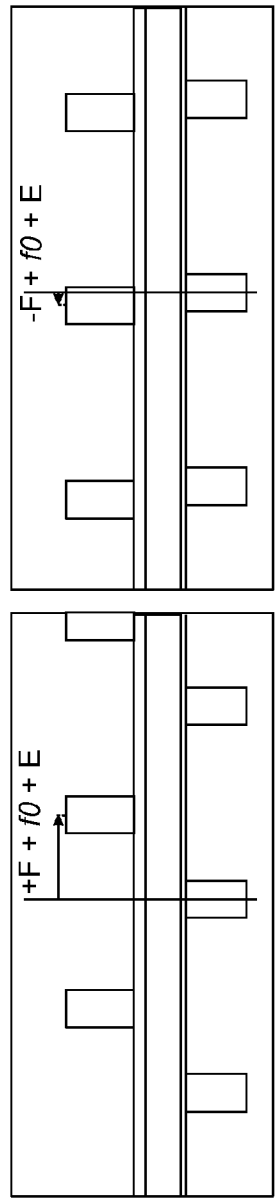
FIG. 2(f) is a side view illustration of a patterned top layer L2 being offset by an amount −F+f0+E from a patterned bottom layer L1 in accordance with one embodiment of the present invention.

FIG. 2(b) is a side view illustration of a patterned top layer L2 being offset by an amount −F from a patterned bottom layer L1 in accordance with one embodiment of the present invention. FIG. 2(c) is a side view illustration of a patterned top layer L2 being offset by an amount +F+f0 from a patterned bottom layer L1 in accordance with one embodiment of the present invention. In one embodiment offset Xa corresponds to +F+f0. FIG. 2(d) is a side view illustration of a patterned top layer L2 being offset by an amount −F+f0 from a patterned bottom layer L1 in accordance with one embodiment of the present invention in one embodiment offset Xb corresponds to −F+f0. FIG. 2(e) is a side view illustration of a patterned top layer L2 being offset by an amount +F+f0+E from a patterned bottom layer L1 in accordance with one embodiment of the present invention. FIG. 2(f) is a side view illustration of a patterned top layer L2 being offset by an amount −F+f0+E from a patterned bottom layer L1 in accordance with one embodiment of the present invention.

In general, an error offset E in one direction, for example along the X-axis, may be determined by analyzing at least the measured spectra (or any type of measured signals) lo obtained from four targets A, B, C, and D each having offsets between two patterned layers, such as offsets Xa through Xd. This analysis is performed without comparing any of the spectra to a known or reference spectra (or signal) from a sample target having a known overlay error. In other words, the error determination techniques of the present invention do not require a calibration operation.

Figure 3A:
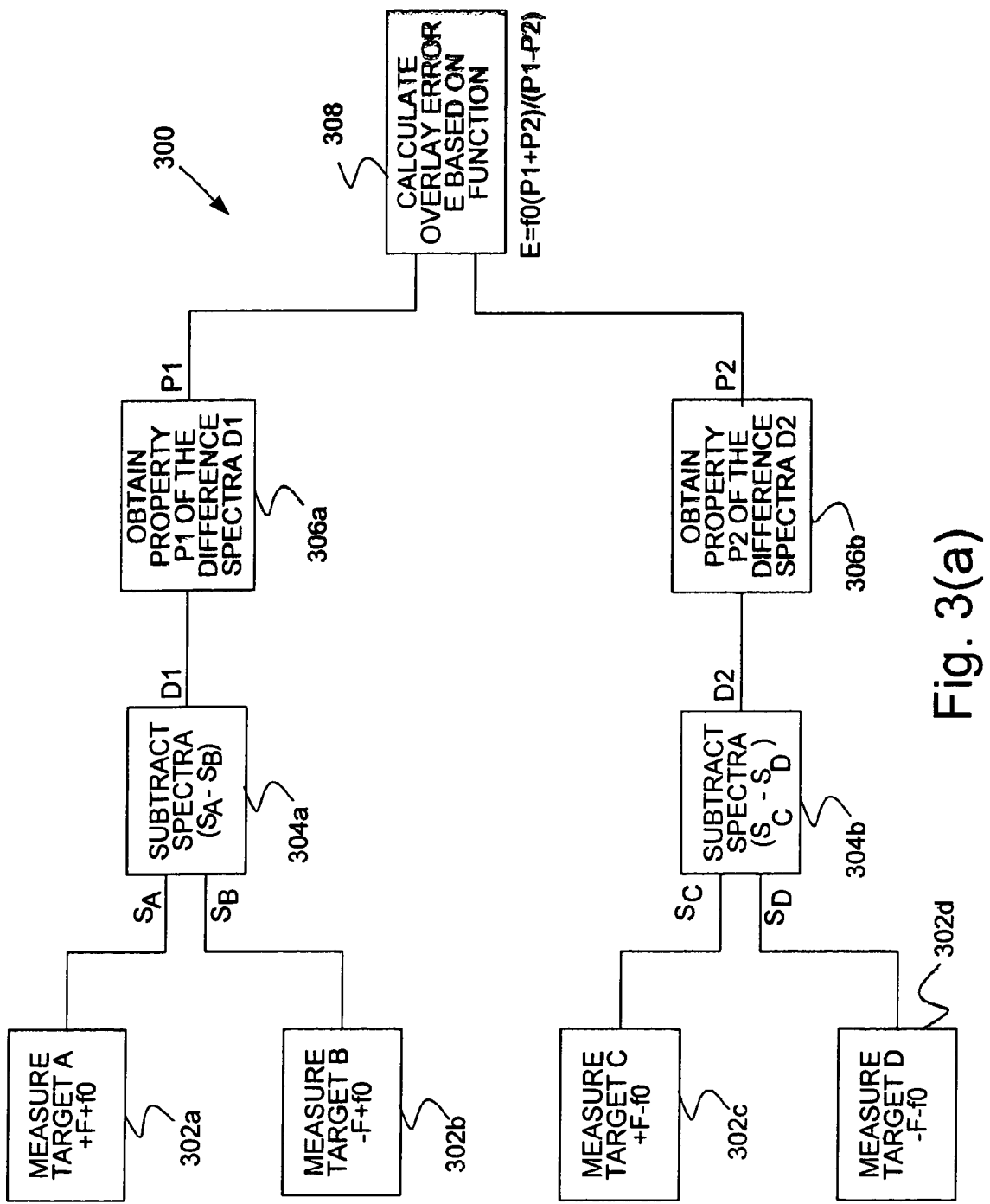
FIG. 3(a) is a flow diagram illustrating a procedure for determining overlay in accordance with one embodiment of the present invention.

FIG. 3(a) is a flow diagram illustrating a procedure 300 for determining overlay in accordance with one embodiment of the present invention. In this example, four targets A, B, C, and D are used which are designed to have offsets Xa through Xd as described above. That is, target A is designed with offset Xa=+F+f0; target B with offset Xb=−F+f0; target C with offset Xc=+F−f0; and target D with offset Xd=−F−f0.

Initially, an incident radiation beam is directed towards each of the four targets A, B, C, and D to measure four spectra $S_A$, $S_B$, $S_C$, and $S_D$ from the four targets in operations 302a through 302d, respectively. Operations 302a through 302d may be carried out sequentially or simultaneously depending on the measurement system's capabilities. The incident beam may be any suitable form of electromagnetic radiation, such as laser, light emitting diode (LED), or broadband radiation.

Although the scatterometry techniques of the present invention are described as utilizing measured spectra from a plurality of targets, any suitable type of measurable signal obtained from an overlay target may be used to practice the techniques of the present invention. Example signals include, but are not limited to, any type of spectroscopic ellipsometry or reflectometry signals, including: Ψ, Δ, Rs (complex reflectivity of the s polarization), Rp (complex reflectivity of the p polarization), Rs ($|r_s|^2$), Rp ($|r_p|^2$), R (unpolarized reflectivity), α (spectroscopic "alpha" signal), β (spectroscopic "beta" signal), and functions of these parameters, such as tan(Ψ), cos(Δ), ((Rs−Rp)/(Rs+Rp)), etc. The signals could alternatively or additionally be measured as a function of incidence angle, detection angle, polarization, azimuthal angle of incidence, detection azimuthal angle, angular distribution, phase, or wavelength or a combination of more than one of these parameters. The signals could also be a characterization of a combination of signals, such as an average value of a plurality of any of the above described ellipsometry and/or reflectometry signal types. The signals may alternatively take the form of a characteristic of one or more image signal(s), such an intensity value(s) or a combination (e.g., average or addition) of intensity values. Other embodiments may use monochromatic or laser light sources where at least one of the signals may be obtained at a single wavelength instead of at multiple wavelengths.

Examples of optical systems and methods for measuring scatterometry signals to determine overlay may be found in (1) U.S. patent application, having patent Ser. No. 09/849,622, filed 4 May 2001, entitled "METHOD AND SYSTEMS FOR LITHOGRAPHY PROCESS CONTROL", by Lakkapragada, Suresh, et al. and (2) U.S. patent application, having application Ser. No. 09/833,084, filed 10 Apr. 2001, entitled "PERIODIC PATTERNS AND TECHNIQUE TO CONTROL MISALIGNMENT", by Abdulhalim, et al. These applications are herein incorporated by reference in their entirety. Further embodiments of suitable measurement systems and their use for determining overlay error are further described below.

After a spectra or signal is obtained from each target, spectrum $S_B$(−F+f0) is then subtracted from spectrum $S_A$(+F+f0), and spectrum $S_D$(−F−f0) is subtracted from spectrum $S_C$(+F−f0) to form two difference spectra D1 and D2 in operations 304a and 304b, respectively. Next, a difference spectrum property P1 is obtained from the difference spectra D1 and a difference spectrum property P2 is obtained from the difference spectrum D2 in operations 306a and 306b, respectively. The difference spectra properties P1 and P2 are generally obtained from any suitable characteristic of the obtained difference spectra D1 and D2. The difference spectra properties P1 and P2 may also each simply be a point on the each difference spectra D1 or D2 at a particular wavelength. By way of other examples, difference spectra properties P1 and P2 may be the result of an integration of averaging of the difference signal, equal an average of the SE alpha signal, equal a weighted average which accounts for instrument sensitivity, noise or signal sensitivity to overlay.

After difference spectra properties P1 and P2 are obtained, the overlay error E may then be calculated directly from the difference spectra properties P1 and P2 in operation 308. In one embodiment, a linear approximation is performed based on the difference spectra properties P1 and P2 to determine the overlay error E, while in another technique the difference spectra properties P1 and P2 are used to approximate a sine wave function or other periodic function which is then used to determine the overlay error E. One linear regression technique is illustrated below with respect to FIG. 3(b). In one example, the overlay result may be obtained by a statistical calculation (e.g. averaging or weighted averaging) of overlay results obtained from properties of multiple wavelengths or multiple wavelength ranges.

In a variation of this implementation, if all four targets have the same characteristics, such as pitch P, thin film characteristics, structure size and composition, except for the offsets, and assuming that Xa and Xb are opposite in sign and have the same order of magnitude and if Xa is the same sign as Xc and Xb is the same sign as Xd, an estimate of the overlay error E present between structures within the interlayer targets can be calculated as follows using a linear approximation based on the difference spectra properties P1 and P2:

$$E'=((S_C-S_D)*(Xa+Xb)/2-(S_A-S_B)*(Xc+Xd)/2)/((S_A-S_B)-(S_C-S_D))$$

or $$E'=(P2*(Xa+Xb)/2+P1(Xc+Xd)/2)/(P1-P2)$$

where the difference spectra properties P1 and P2 are generally opposite in sign for overlay errors E<f0. If (Xa−Xb)=(Xc−Xd) and E=0, then P1=−1*P2.

Alternatively, if the same values for F and f0 are used for designing each target offset Xa, Xb, Xc, and Xd, then $$E'=(f0*P2+f0P1)/(P1-P2).$$

The targets may be used to determine overlay of structures located at least partially in more than one layer, but could also be used to determine overlay of structures located substantially in a single layer. In other embodiments, the offsets may have the same sign.

Figure 3B:
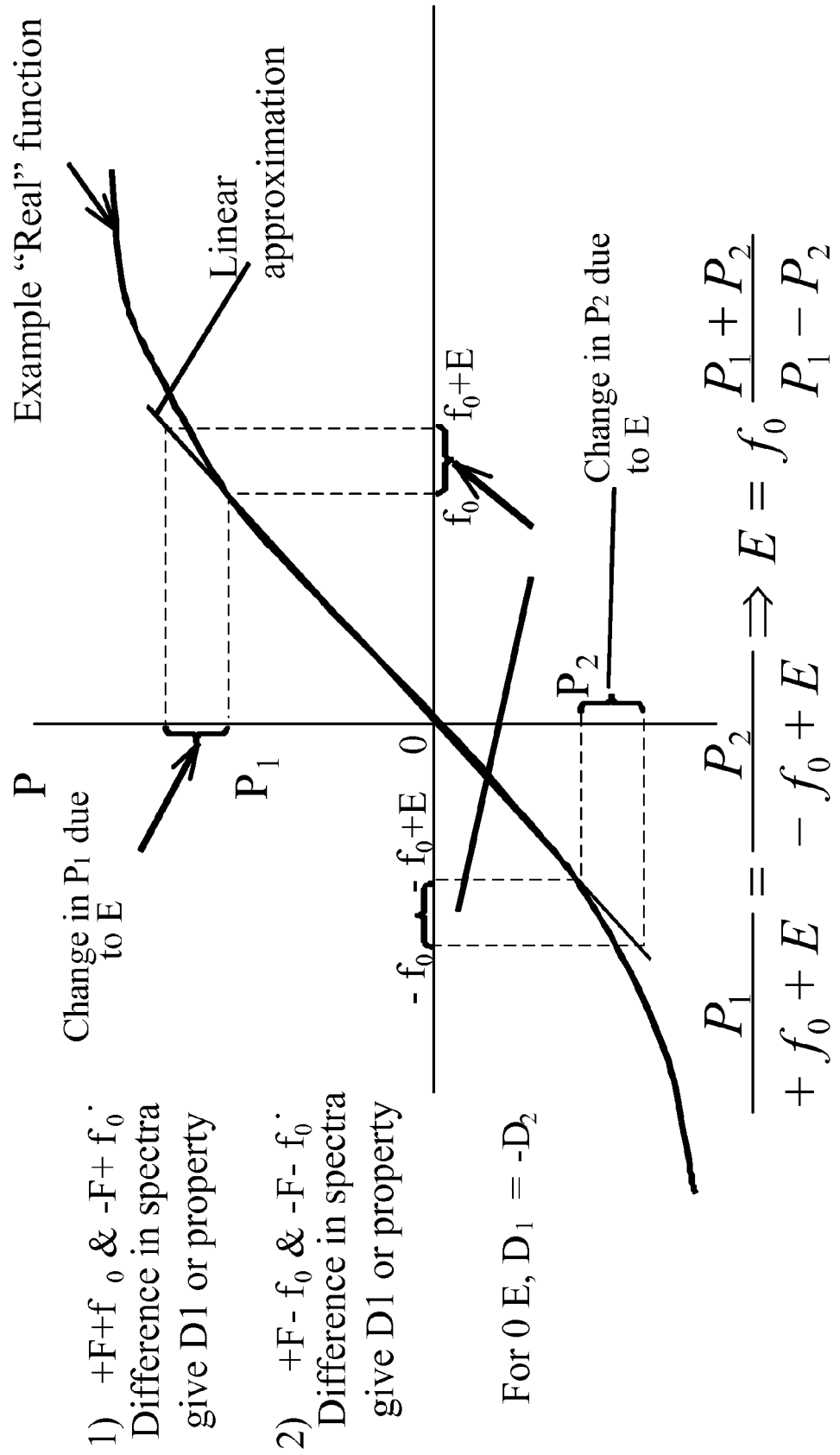
FIG. 3(b) shows a graphical representation of an approach to determination of overlay according to an embodiment of the present invention.

FIG. 3(b) shows a graphical representation of the linear approach for determining the overlay error E in accordance with one embodiment of the present invention. As shown, the positive portion of the y axis shows a change in the difference spectra property P1 as a function of f0+E and the negative portion of the y axis shows a change in the difference spectra as a function of −f0+E. As described above, the difference spectra properties P1 and P2 are obtained from the difference spectra D1 and D2.

The overlay error E may be obtained by analyzing the two points (+f0+E, P1) and (−f0+E, P2). The overlay error E may be determined in one approach by performing a linear approximation with the two obtained difference spectra properties P1 and P2. Note that there are two points on the graph where E is zero, while other portions of the graph are a function of the overlay error E and f0. If the offsets are chosen carefully so as to be in the linear region, then the slope of the positive portion of the graph (P1/(+f0+E)) should equal the slope of the negative portion of the graph (P2/(−f0+E). Thus, the overlay error is given by E=f0*(P1+P2)/(P1−P2).

According to an implementation of the invention, if there are two targets with offsets +F and −F that are equal in magnitude but opposite in sign and no other overlay errors, then the 0th diffraction order scatterometry SE or reflectometry spectra are substantially identical from these two targets (to a good approximation) and the difference signal between the spectra corresponding to +F and −F is zero. Of course, any property of the difference signal is also zero. If one deliberately breaks the symmetry (artificially induces an overlay error) by designing an additional offset +f), then the difference signal D1 is no longer zero and any suitable difference spectra property follows the same relationship as for an overlay error E. Similarly one can design another set of overlay targets with an additional offset −f0. Thus, the overlay error may be determined using a property of the difference signals D1 (+F+f0, −F+f0) and D2 (+F−f0, −F−f0), and accordingly no separate calibration step is required.

It should be understood that when the overlay error E is calculated from the spectra signals, it may be an estimate of actual overlay error. The calculated overlay error E may be denoted as the overlay error (E), or an estimate of the overlay error (E').

If the pitch between structures is relatively large then the above described linear approximation techniques generally work well. However, when the pitch is relatively small then additional targets may be produced on the sample to improve the accuracy of the overlay measurements. The number of targets and corresponding scatterometry techniques which are used depend on the particular materials of the target and the scatterometry signal type implemented, among other factors. The number of targets can be determined experimentally or by well known modeling methods. In one embodiment, two additional interlayer targets (denoted targets "H" and "J") are produced on the sample, with corresponding offsets Xh and Xj. Upon being illuminated by incident radiation, the targets H and J produce corresponding diffracted components, which can serve as a basis for determination of an additional difference signal D3 and difference spectra property P3. This property P3 may be analyzed in connection with the difference spectra properties P1 and P2 to refine the determination of the overlay E to include non-linear corrections or measurements of the errors introduced by using a linear approximation.

In one target implementation, each of the targets A, B, C, and D comprises a grating structure Ga1 having periodic structures with a period Ta1 disposed at least partially within the first layer and a grating structure Ga2 having periodic structures with a period Ta2 disposed at least partially within the second layer (e.g., the target of FIG. 2c or 2d). Generally, a target could be any periodic structure like a particular device pattern repeated a number of times. One or more of the gratings Ga1 and/or Ga2 may be formed from device-like (e.g., design rule based) or process robust (e.g., low variability under variable process conditions). The first layer period Ta1 and the second layer period Ta2 could be identical or different as well (in the simplest case Ta1=n*Ta2 or Ta2=n*Ta1, where n is an integer), and the offsets Xa, Xb, Xc, and Xd are each produced by offsetting the structures with the period Ta1 of the grating structure Ga1 with respect to the structures with the period Ta2 of the grating structure Ga2 by the sum of a first distance F and a second distance f0, wherein the second distance f0 has a smaller absolute value than the first distance F.

In another target embodiment, the composite periodic structure comprising Ga1 and Ga2 is periodic with a period Ta, and it is possible to describe both Ga1 and Ga2 in terms of the period Ta, with Ga1 possibly having a complex structure (complex unit cell with multiple components) and Ga2 also possibly having a different complex structure (complex unit cell with multiple components). For example, a unit cell may include a set of closely spaced line segments adjacent to a large flat area. This unit cell is repeated to form either or both grating Ga1 or Ga2. Gratings Ga1 and Ga2 may have the same or different unit cells. Additionally, the unit cells of Ga1 may be a rational or integer number of the units cells of grating Ga2, or visa versa. Gratings Ga1 and/or Ga2 may also be designed to be similar to the critical device features—i.e. share one or more of the device characteristics such as pitch, line width, etc. Scatterometry overlay targets designed to be similar to the device features may provide advantages by processing more similarly to the device features, including reflecting the pattern-dependent overlay effects such as pattern-placement error.

One alternative embodiment to the linear approximation methods discussed above is to treat the scatterometry overlay signal as a periodic function and use phase detection methods to determine the overlay error (herein referred to as a phase scatterometry approach). This embodiment may be preferred in some circumstances, depending on variables that may include scatterometry overlay target pitch, scatterometry overlay target design, scatterometry overlay (SCOL) target materials, the measured scatterometry signal, and the like.

The overlay error may be extracted from measuring multiple SCOL targets with pre-programmed additional built-in overlay offsets. (One example of the preprogrammed offsets could be Xa, Xb, Xc, and Xd as discussed above and in FIG. 1). The number of targets measured may be two, three, four, or more than four, or may vary between different overlay measurement locations. For the phase methods, it may be advantageous for the offsets to be evenly distributed throughout the period, with differences corresponding to the period divided by the number of targets (e.g. Xa−Xc=Xc−Xb=Xb−Xd=Xd−Xa+P=P/4 for 4 targets for one direction). Alternatively, the offsets could be designed to distributed unevenly throughout the period which may be advantageous when used with some phase-detection algorithms.

A scatterometry signal (as a function of the wavelength or incident angle, for example) is acquired from each of the required SCOL targets. This signal is generally a periodic and even function of overlay error, for the case where the offsets are measured from a symmetry position of one of the L1 or L2 patterns. A phase detection (or phase retrieval, phase extraction, or phase determination) algorithm utilizes these properties of the signals.

The measured signal is represented by a set of even periodic functions with a corresponding number of free parameters (one of these free parameters is the overlay error itself). For example, each measured signal may be represented by a Fourier series expansion having any number of terms consistent with the number of targets measured. The number of terms depends on the number of targets measured, scatterometry signal properties, target properties, and information required. In a Fourier series having three terms, a measured signal may be represented by:

$$k + 1\cos\left(\frac{2\pi}{P}(V_i + E)\right) + m\cos\left(\frac{4\pi}{P}\right)(V_i + E)$$

where k is a constant; l is an amplitude of the first harmonic; m is the amplitude of the second harmonic; Vi represents the predefined offset; P is the period; and E is the overlay error. The number of targets measured is to be greater or equal to the cumulative number of free unknown parameters in the chosen function. In the above three term example, there are four unknowns: k, l, m, and E where the period is 360 degrees or 2Π radians. Therefore, four targets may be used to solve for the four unknowns which include overlay E.

When several (two or more) scatterometry overlay (SCOL) targets (with different pre-programmed offsets) are placed in the immediate vicinity of each other (within 0 to 250 microns, for example), the overlay error may be assumed to be the same for all these targets. Each of the other free parameters can either vary or not vary from one SCOL target location to the other one (within the field and/or across the wafer). (Overlay is assumed to vary between different overlay measurement locations in the stepper field or across the wafer). Alternatively, these free parameters (or some of them) may either vary or not vary between X- and Y-SCOL target orientations. Based on the information required, the measurement accuracy required and on whether some free parameters are not varying location-to-location and/or between X- and Y-orientations, the total number of SCOL targets per overlay measurement location and total number of SCOL targets to be measured per field and/or per wafer is determined.

An example of a phase algorithm approach to determining overlay error from scatterometry signals from multiple targets is to treat the dependence of the scatterometry signals on overlay error as a periodic function. In this case the programmed offsets of the multiple targets are treated as initial phase offsets and the overlay error is treated as an additional phase. The overlay error can then be determined using well-known phase determination or phase retrieval methods. Well known phase retrieval methods that may include quadrature, 3-bucket, and 4-bucket phase retrieval algorithms can be used to determine overlay error. These phase retrieval methods are listed as examples only and are not meant to limit the scope of the invention. Phase detection methods are well known and are commonly used in diverse areas such as communications, interferometry, nuclear magnetic resonance, electronic circuits, to list a few examples. In another embodiment, a combination of linear, non-linear, and phase retrieval algorithms may be employed to determine the overlay error.

Certain conditions are preferably met with implementation of the above described techniques. The measurement areas are substantially identical in all aspects except for the offsets, e.g., +F+f0, −F+f0, +F−f0, and −F−f0. This is likely accomplished by placing the targets within about 100 microns or less of each other and by choosing targets which are relatively-robust to the process (i.e. they have similar or less sensitivity to process variation as the device features). In practice, on production wafers, the profiles may deviate from identical for different offsets if the topography from the lower pattern layer(s) and the upper layer changes in response to interacting with this topography. A difference or error signal between the two targets with different offsets is relatively independent of profile variation of the overlay target segments and to film variation as long as the profiles are common to the different targets. This is the substantial equivalent of common mode rejection of the parts of the signal that are determined by the profile and the films and the optics. The technique is also preferably robust to the range of process variation encountered in a typical manufacturing process. The signal differences due to the overlay error are also preferably larger than the signal differences due to other sources of process variation between the nearby scatterometry overlay targets (including mask errors).

If in a particular implementation the targets include structures grouped to exhibit the characteristics of lines, then a separate set of targets may be required for X and Y overlay measurements. If the overlay targets are composed of 2-dimensional structures (as seen from a top down view), then it may be possible to use one set of targets to get both X and Y overlay information. For oblique scatterometry, according to a specific implementation, it may be advantageous to rotate the orientation of the wafer with respect to the optical scattering plane to measure the different X and Y overlay errors. For true normal incidence, it may be possible to get both X and Y overlay information from the different polarizations without rotating the wafer or the optics.

Cartesian coordinates provide a convenient frame of reference for measuring overlay within a sample, with the x-y plane being located within, or substantially parallel with, a layer of the sample, and with the z axis being substantially perpendicular to the layers of the sample. The Cartesian coordinate system could be fixed with respect to the sample or could be rotated to reduce the complexity of the measurements. For example, overlay occurring diagonally across the sample but within a single layer could be described as two-dimensional x-y overlay in a Cartesian system with the x-y axes substantially parallel with the sides of a rectangular sample or stepper field. That same diagonal overlay could be measured along a single axis, however, by rotating the x-y axes such that the x axis is parallel with the direction of the diagonal overlay.

In one embodiment, targets include more than one predefined offset, possibly between different sets of structures located in two layers, or possibly between different sets of structures located in more than two layers. In a general case, a target may include an indefinite number of layers, with all or some of these layers having structures producing predefined offsets. In a particular implementation, the structures in one or more underlying patterned layers of a target cause changes in the shape or topography of one or more upper layers (disposed above the underlying patterned layer(s)). In this implementation, the one or more upper layers may be substantially or partially opaque or absorbing, and at least part of the diffraction signal may arise from the topography of an upper layer, the topography arising at least in part from the underlying patterned layer.

According to one embodiment, structures included in a target may be organized in various configurations and shapes, including, for example, lines, grids, rectangles, squares, curved lines, curved shapes, circles, cylindrical shapes, conical shapes or combinations of the foregoing. Such configurations of structures may be disposed at various locations within the target, and may describe various angles with respect to the electromagnetic radiation incident on the target. For example, the sets of structures could be organized as a set of parallel lines perpendicular to the direction of propagation of a collimated set of radiation rays or of a beam incident on the target. In another case, the structures organized as a set of parallel lines could be disposed at an acute angle with respect to the incident radiation, possibly at an angle of 45 degrees. Such a configuration could be advantageous by facilitating determination of overlay in both x and y directions, thereby reducing the need for additional overlay patterns or measurements.

Alternatively, the incident radiation could be directed to be substantially parallel to at least some of the parallel lines comprising the structures or defining the structures. This technique allows one to perform x and y overlay measurements without rotating the sample.

1. Scatterometry System Embodiments and Uses of Same

Several of the techniques of the present invention may be implemented using any suitable combination of software and/or hardware system. For example, the techniques may be implemented within an overlay metrology tool. Preferably, such metrology tool is integrated with a computer system which implements many of the operations of this invention. Such composite system preferably includes at least a scatterometry module for obtaining scatterometry signals of the overlay targets, and a processor configured to analyze the obtained scatterometry signals to thereby determine overlay error within such targets. At a minimum, the scatterometry module will usually include (i) a source of illumination oriented to direct radiation onto a specified location of the sample; and (ii) one or more detectors oriented to detect a scatterometry signal which has been scattered by the sample.

At least a portion of the techniques of the present invention may also be implemented in an overlay metrology system as an additional overlay measurement capability which complements an overlay measurement system or sub-system based on image analysis such as one used for conventional box-in-box or frame-in-frame overlay targets or other imaging type overlay measurement structures. Examples of apparatus which combine imaging-based overlay metrology and scatterometry-based overlay are described in the above referenced Provisional Application No. 60/498,524, which is incorporated here by reference. Several embodiments of such a combinational system are described further with respect to FIGS. 11*d* through 11*f.* Overlay data from imaging overlay measurements and scatterometry overlay measurements may be combined for various uses including: calculating the overlay correctables, calculating other overlay corrections, calculating overlay errors at other locations on the wafer. More use cases for combinations of imaging overlay metrology and scatterometry overlay metrology are also described in above referenced Provisional Application No. 60/498,524 and are described further below.

Regardless of the system's configuration, it may employ one or more memories or memory modules configured to store data, program instructions for the general-purpose inspection operations and/or the inventive techniques described herein. The program instructions may control the operation of an operating system and/or one or more applications. The memory or memories may also be configured to store scatterometry data obtained from the targets and overlay error results and optionally other overlay measurement data.

Because such information and program instructions may be employed to implement the systems/methods described herein, embodiments of the present invention relates to machine readable media that include program instructions, state information, etc. for performing various operations described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). The invention may also be embodied in a carrier wave traveling over an appropriate medium such as airwaves, optical lines, electric lines, etc. Examples of program instructions include both machine code, such as produced by a compiler, and files containing higher level code that may be executed by the computer using an interpreter.

Several of the system embodiments described below are mainly described and illustrated with respect to a scatterometry module or components for obtaining spectra (or other measurable signals) from a plurality of targets, while the processor and memory are not shown. Additionally, several of the systems are described herein with respect to the above described linear scatterometry approach. Of course, any suitable scatterometry approach, such as the phase approach may be utilized.

Figure 4:
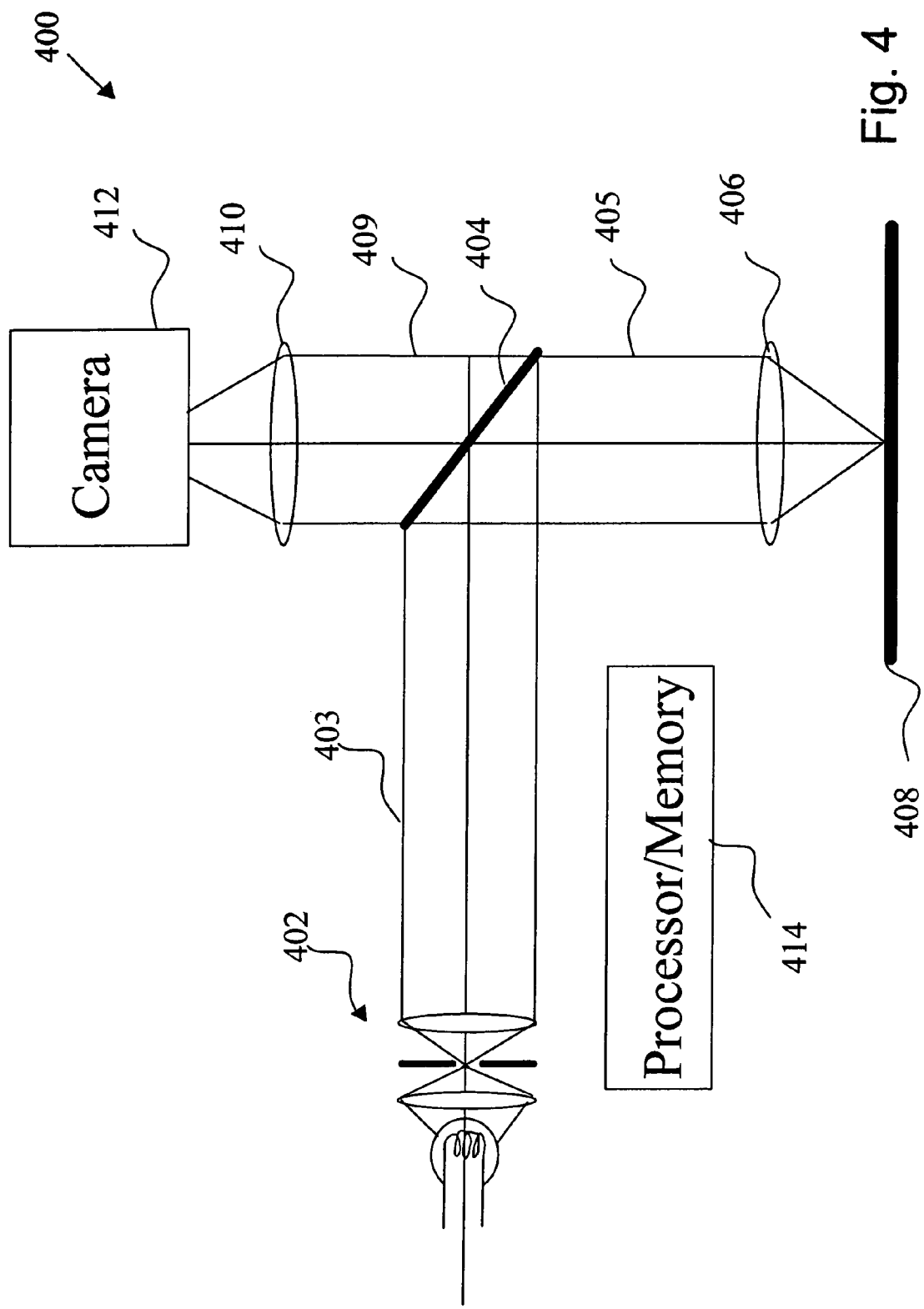
FIG. 4 is a diagrammatic representation of a conventional microscopic imaging system.

Imaging Metrology Systems in which the Numerical Aperture is Optimized for Measurement of Scattering Structures FIG. 4 is a diagrammatic representation of a microscopic imaging system. As shown, the imaging system 400 includes a beam generator 402 for producing an incident beam 403 of electromagnetic radiation, a beam splitter 404 for directing the incident beam 405 towards the sample 408. Typically, the incident beam is focused onto the sample by an objective lens 406. An output beam 409 is then emitted from the sample in response to the incident beam and passed through the beam splitter 404 through relay lens 410 onto imager or camera 412. The camera 412 generates an image of the sample based on the output beam 409.

The system 400 also includes a processor and one or more memory 414 which are configured to control the various components, such as the beam generator 402, objective lens 406, and cameral 412. The processor and memory are also configured to analyze the detected output beam or image implementing the various scatterometry techniques described above.

Traditionally, such imaging systems (such as those used for overlay) have selected numerical apertures (NA's) (e.g., via objective lens 406) to optimize image resolution and to minimize optical aberrations. Selection of NA is typically performed in order to derive the overlay information from the variation in intensity over a single target (such as a box-in-box target) from the geometrical properties of the image.

Conventional imaging systems have relied upon high numerical apertures (NA's), such as 0.7 to 0.9, but doing so results in an expensive optical system which is sensitive to vibration, depth of focus, and optical aberrations. These issues reduce the achievable precision and cause a measurement error referred to as "tool induced shift" or TIS.

Scatterometry systems may take measurements at multiple sites sequentially in order to measure both x and y overlay and to eliminate effects due to variations in other sample parameters, such as film thickness. This type of measurement process results in significantly slower operation of the scatterometry tool relative to conventional overlay techniques.

In one embodiment of the present invention, the illumination and imaging NA's of an imaging optical system are chosen to optimize the performance of the instrument on scattering structures by ensuring that only the zero'th diffraction order is collected. One may take advantage of the fact that there exist performance advantages for certain metrology or inspection tasks pertaining to periodic structures when only the zero order diffraction is collected by the detection system. Under this condition, only the specular reflection is collected. Since the output which is scattered out of the specular is not collected and the nonspecular output may be more sensitive to aberrations, collection of only the specular output tends to minimize effects caused by optics aberrations. This condition also will result in a tool which will be optimized for relative photometric measurements of multiple sites in the field of view as described further below. Very low TIS may also be achieved, as compared to conventional imaging systems. Much higher throughput may also be achieved than with conventional scatterometry systems.

Choosing the illumination and imaging NA's for a particular imaging system is based on the particular configuration of such system. If we now consider the simplest imaging system in which the numerical aperture NA of illumination and collection are the same and the incident beam in normal to the sample surface, then the condition of "zero order diffraction only" can be met if:

$n\lambda > 2dNA$, where $n=1$.

where d is the pitch of the structures of the targets being imaged. This can be restated in terms of the numerical apertures of illumination $NA_i$ and collection $NA_c$ of the imaging system as:

$n\lambda = d(NA_i + NA_c)$

This equation indicates that if we are able to constrain the numerical aperture of the illumination system, we can relax the constraint on the numerical aperture of the collection optics, which may be advantageous under certain conditions. Thus, the spectral range may be restricted to wavelengths greater than twice the product of the pitch and the NA. Under realistic conditions the scattered radiation beam will be wider (more divergent) than the illumination beam. Under realistic circumstances however, infinitely periodic gratings are not imaged and so the above equations become approximations and the diffracted plane waves become somewhat divergent. So it may be preferable to include a margin of safety in the constraint and require that:

$n\lambda \geq 2dNA(1+\epsilon)$, where $n=1$ and $\epsilon$ is small, typically less than 0.5.

As an example, for an NA 0.4 imaging system, wavelengths may be restricted to values greater than 0.8 times the largest pitch, which does not seem to be an unreasonable constraint. For periodic structures having features of design rule 70 nm and below, the densest structures with pitches as low as 200 nm does not constrain the spectral range of imaging systems with operating wavelengths equal to about 200 nm or longer, while more isolated features with pitches as large as 500 nm are preferably measured with wavelengths longer than 400 nm.

It is preferable to account for these constraints when designing an imaging spectrometer for metrology and inspection applications. A limit on the spatial resolution of the imaging system is the numerical aperture of the system. It is advantageous to achieve the highest spatial resolution so as to be able to shrink to a minimum the size of metrology structures and conserve valuable wafer real estate. Restated, this allows minimization of proximity effects or "crosstalk" between adjacent features in the field of view of the imaging spectrometer. Therefore, the highest possible NA is achieved while meeting the constraint that only the zero order diffraction is collected by the detection system.

Another interesting outcome of this constraint is that the highest possible overlay spatial resolution may be achieved without ever resolving the features under test. This may have further advantages as it should ensure that problematic aliasing phenomena are avoided in the imaging system. In a preferred embodiment, an architecture is provided in which the spectral band pass can be easily modified or selected by the measurement system or algorithm based on the largest pitch in the feature under test (e.g., as the systems in FIGS. 5A through 5D described further below). Alternatively, the NA of either illumination or collection could be easily modified, depending on the largest pitch in the feature under test. Alternatively, all of these embodiments may be implemented within a single system.

Figure 5A:
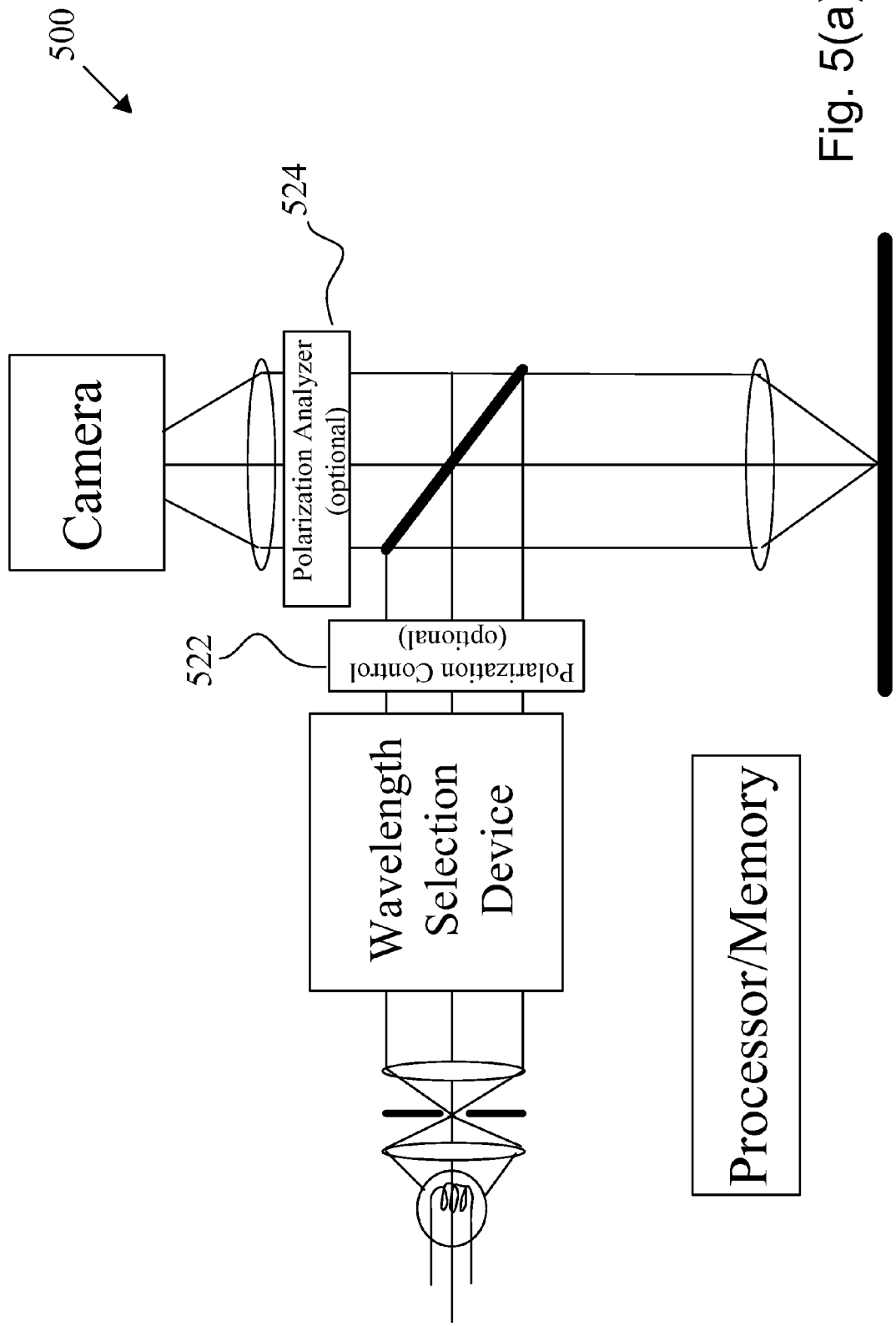
FIG. 5(a) is diagrammatic representation of a microscopic imaging system comprising a wavelength selection device, illumination polarization control, and polarization analyzer in accordance with a first embodiment of the present invention.

FIGS. 5A through 5E illustrate four embodiments of microscopic imaging systems having a numerical aperture (NA) optimized for scattering characteristics. As shown in FIG. 5A, the system 500 may have components which operate like the same named components of the system in FIG. 4. The system 500 further includes a wavelength selection device 520 for selecting a particular wavelength. The wavelength selection device allows light of different wavelengths to be sent selectively to one or more detectors. A wide variety of well known spectroscopic filtering techniques may be employed to modify the spectra band, including selecting from a set of band pass interference filters, continuously varying bandpass interference filters, grating based spectrometers, acousto-optic tunable filters, to name a few. The wavelength selection device 520 is positioned within the incident beam path. The system 500 may also include a polarizer control device 522 for causing the incident beam to be in a particular polarization state and a polarization analyzer 524 for analyzing or separating out the polar components of the collected beam.

Figure 5B:
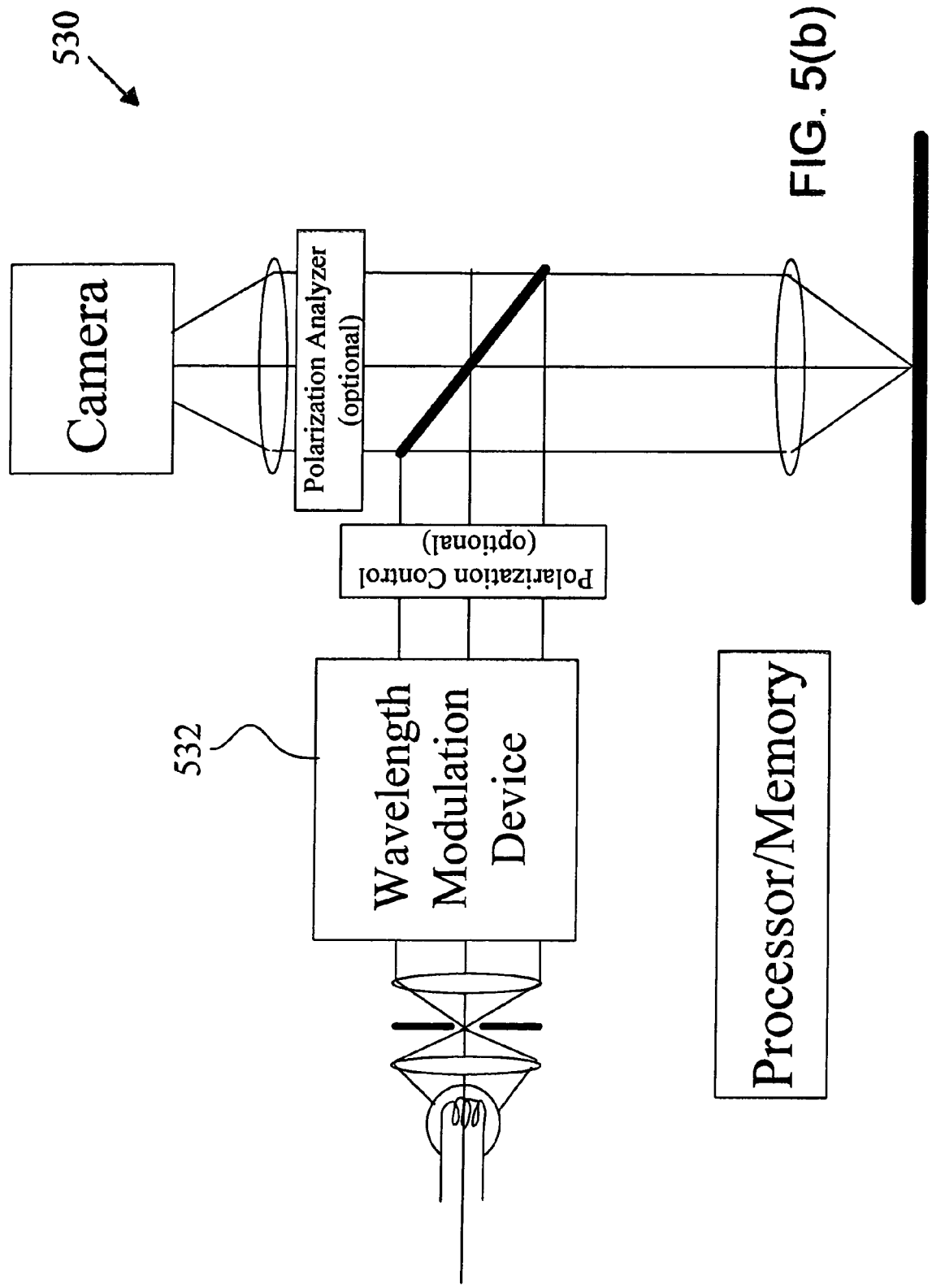
FIG. 5(b) is diagrammatic representation of a microscopic imaging system comprising a wavelength modulation device, illumination polarization control, and polarization analyzer in accordance with a second embodiment of the present invention.
Figure 5C:
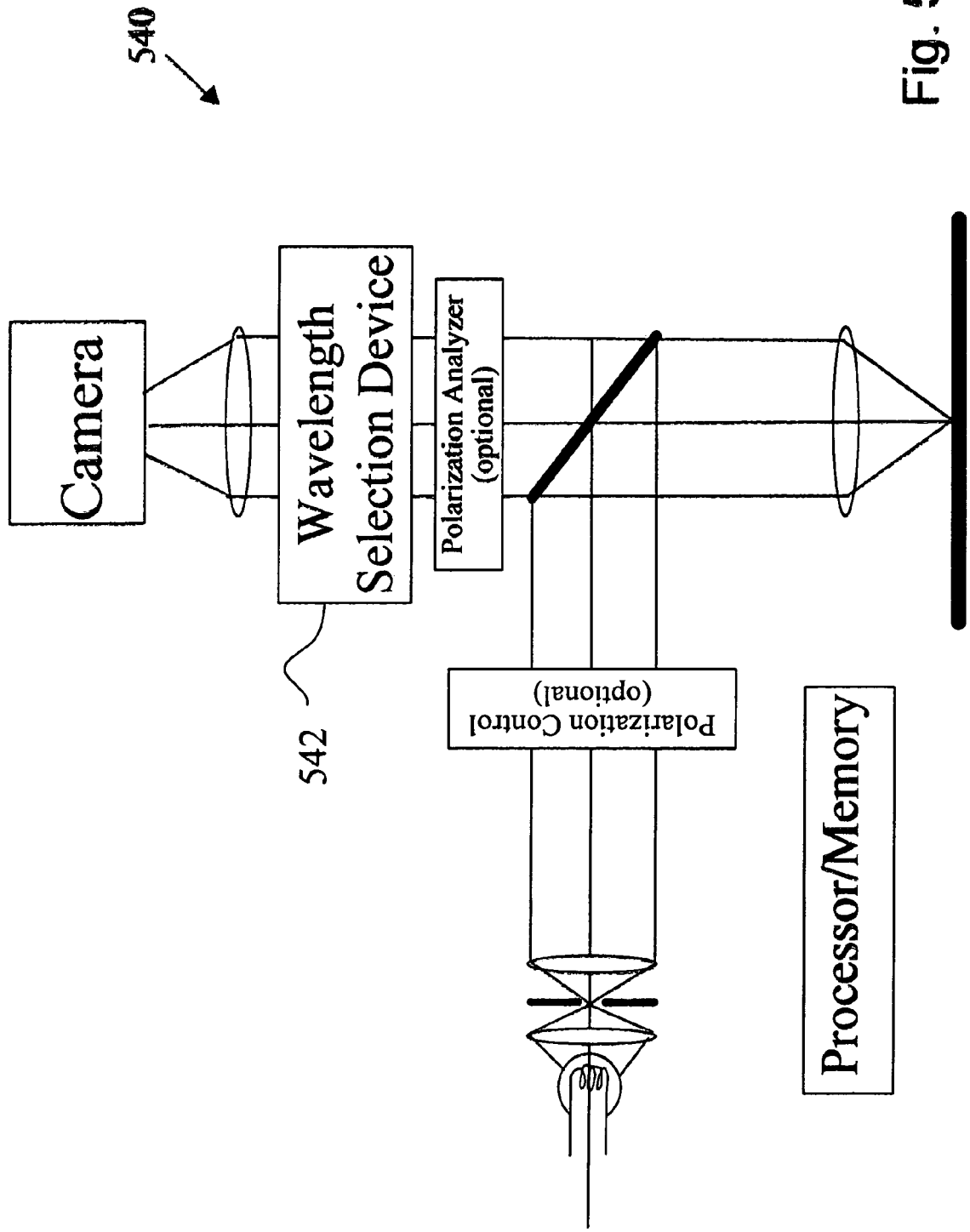
FIG. 5(c) is diagrammatic representation of a microscopic imaging comprising a illumination polarization control, polarization analyzer, and wavelength selection device, in accordance with a third embodiment of the present invention.
Figure 5D:
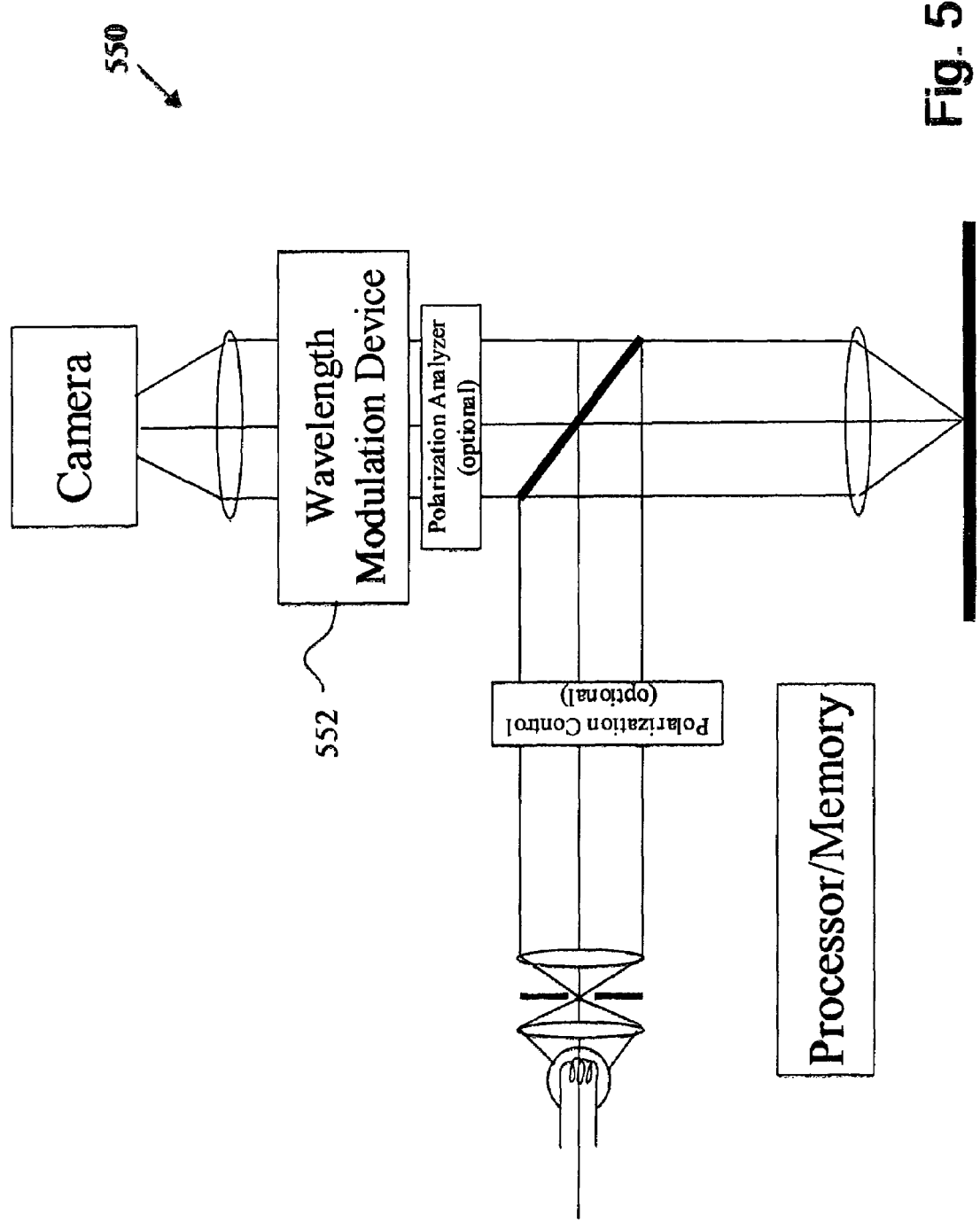
FIG. 5(d) is diagrammatic representation of a microscopic imaging system comprising a illumination polarization control, polarization analyzer, and wavelength modulation device in accordance with a fourth embodiment of the present invention.

The system 530 of FIG. 5B is similar to the system 500 of FIG. 5A, except a wavelength modulation device 532 is used in place of a wavelength selection device. The system 540 of FIG. 5C is similar to the system 500 of FIG. 5A, except the wavelength selection device 542 is positioned in the output beam path. The system 550 of FIG. 5D is similar to the system 500 of FIG. 5C, except a wavelength modulation device 552 is used in place of a wavelength selection device. The wavelength modulation device operates by modulating the intensity of different wavelengths in different temporal patterns such as different sinusoidal frequencies.

The most common examples of such a device are interferometers which can be controlled by changing one or more optical path lengths in the wavelength modulation device 532 itself (e.g., an interferometric system, such as in a Michelson, Fabry-Perot, or Sagnac interferometers). The spectral information may be derived from the resulting signal with a transform analysis like a Fourier transform or Hadamard transform, for example.

Figure 5E:
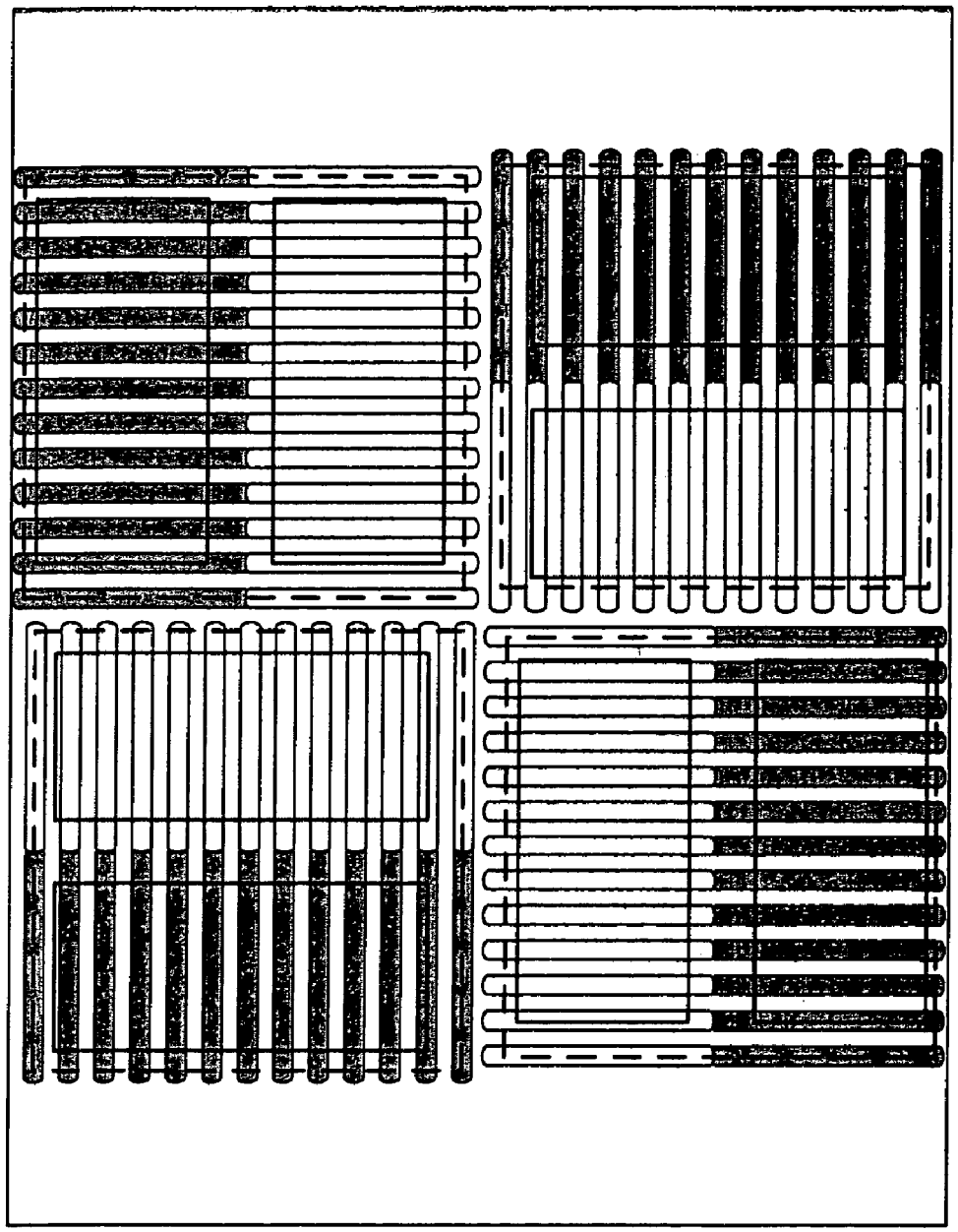
FIG. 5(e) is a top view representation of an imaging spectrometer, multiple site field-of-view example in accordance with one embodiment of the present invention.
Figure 11A:
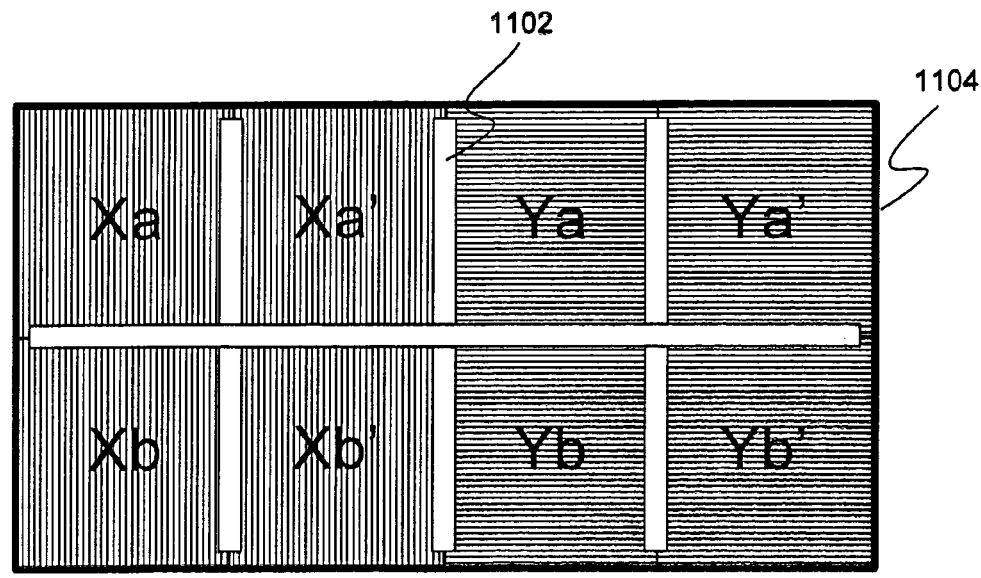
FIG. 11a is a top view representation of a first combination imaging and scatterometry target embodiment.

FIG. 5E is a top view representation of an imaging spectrometer, multiple site field-of-view example in accordance with one embodiment of the present invention. In one implementation, spectra from one or more pixels in each dotted box are averaged to create a spectrum for each of the four measurement targets. Alternatively, spectra from one or more pixels located only in a central region of each dotted box are averaged together. Size and spacing of lines in the illustrated targets are exaggerated for emphasis. There is an area where the lines of layer 2 are disposed above the lines of layer 1 for at least part of the target. The signals for this area are detected as scatterometry overlay signals. Another example of the targets is shown in FIG. 11a.

Figure 5G:
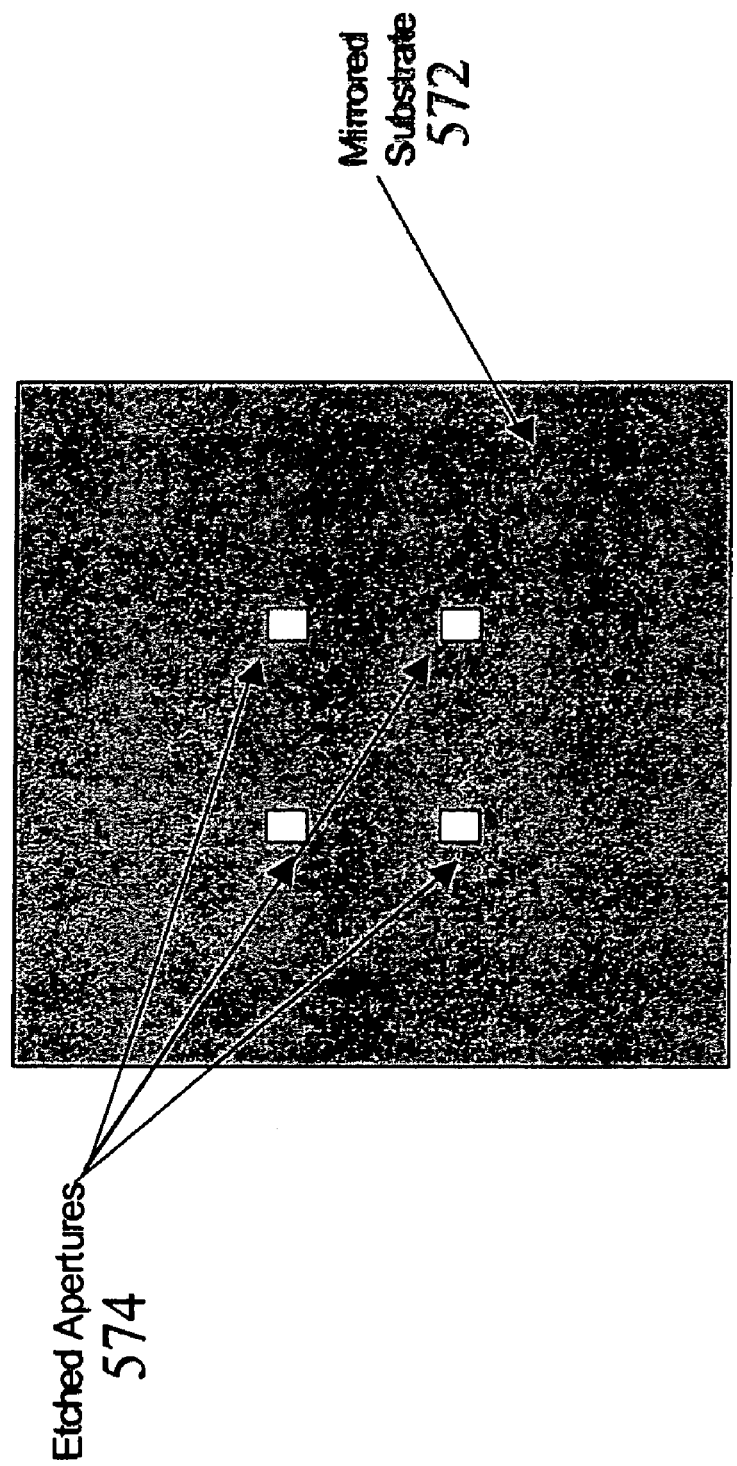
FIG. 5(g) is a diagrammatic representation of the aperture mirror of FIG. 5(f) in accordance with one embodiment of the present invention.
Figure 5H:
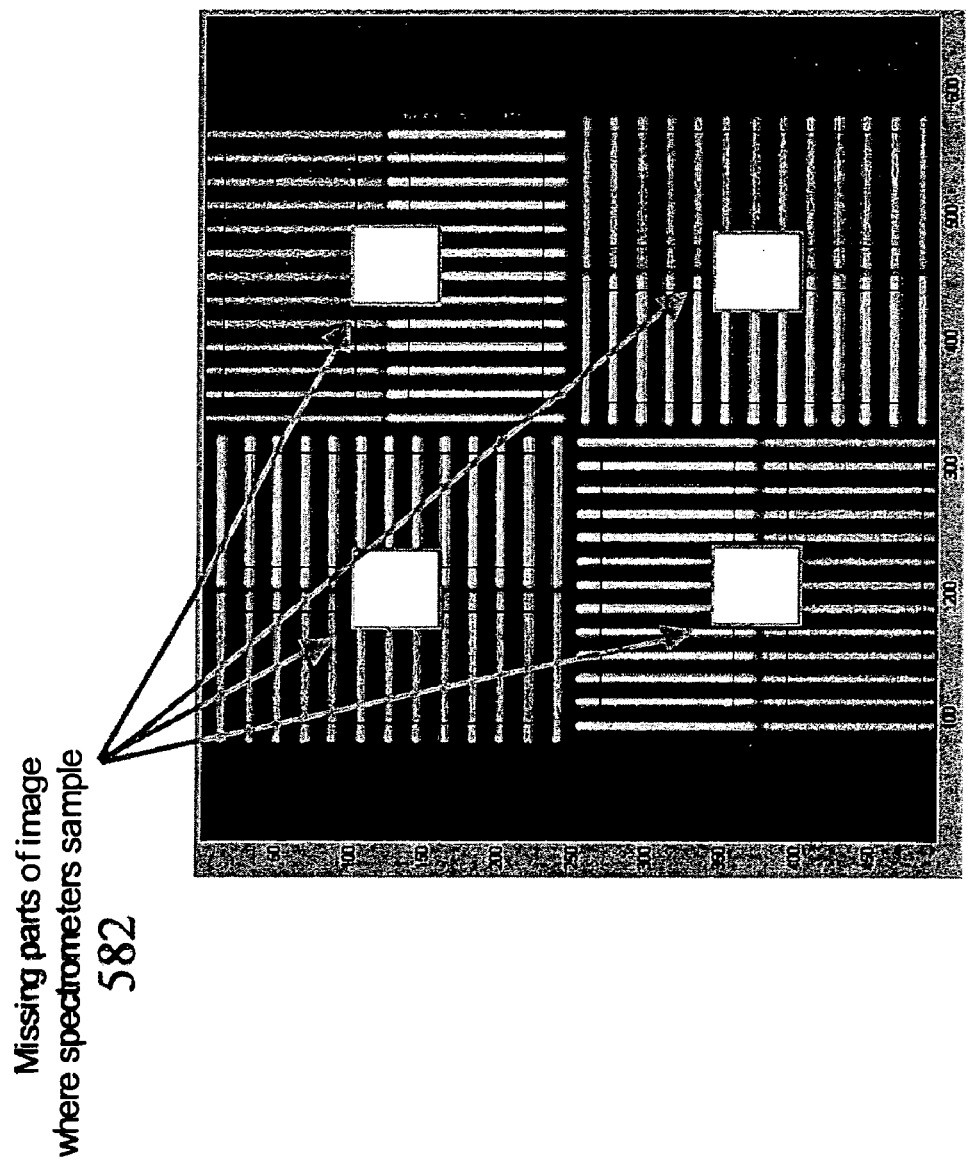
FIG. 5(h) is a top view representation of an imaging spectrometer, multiple site field of view example with aperture components sent to spectrometers in accordance with one embodiment of the present invention.

FIG. 5(f) is a diagrammatic representation of a fixed, discrete channel optical system in accordance with a fifth embodiment of the present invention. In this embodiment, the system includes a mirror having spectroscopic apertures 562. That is, the mirror is reflected, except for a plurality of apertures which let the light from the sample pass through in particular spatial portions. FIG. 5(g) is a diagrammatic representation of the aperture mirror of FIG. 5(f) in accordance with one embodiment of the present invention. As shown, the mirror 572 includes four etched apertures 574. The apertures 574 are etched within a mirror reflective substrate 572. In one implementation, the light which corresponds to each center portion of each target pass through the mirror to separate detectors, e.g., fiber pickoffs to spectrometers 564. The remaining portion of the target image, excluding the central image portions for each target, is reflected by mirror 562 to a camera. FIG. 5(h) is a top view representation of an imaging spectrometer, multiple site field of view example with missing aperture components (that are sent to spectrometers) in accordance with one embodiment of the present invention. As shown, the camera image of the targets contain missing portions 582 which signals are sent to spectrometers, instead of a camera.

The NA of any of the above described systems may be selected to ensure that only the zero'th diffraction order is collected in any suitable manner. In one proposed operational embodiment:

1. Two or more sites of differing characteristics are located in the field of view of the imaging system.
2. Images are captured over one or more spectral ranges.
3. For each measurement site in the field of view, all or some of the pixels determined to be within that site are summed or otherwise combined to characterize the photometric properties of that site in that spectral range.
4. Step 3 is repeated for each spectral range.
5. The results for each site over each spectral range are processed to determine the properties of the sample. For example, the above described spectral analysis techniques (i.e., F+f0) are used on the obtained spectra for each target.
6. Steps 1 though 5 are repeated for the plurality of measurement sites desired across the wafer.

While this example technique describes sequentially capturing images over different spectral regions, this could be accomplished simultaneously using a system of wavelength dependent beam splitters, filters, and/or mirrors. Alternatively, the same could be affected by using a device such as a Sagnac interferometer which captures multiple images at different optical path differences, these being used to derive information equivalent to images taken over different spectral ranges.

Scatterometric Overlay Using Filters

Conventional imaging overlay tools have a high magnification and small field of view. Inspection for gross patterning defects is either done manually on a microscope or automatically on a separate macro inspection tool. A low magnification overlay tool unfortunately requires multiple steps or tools, some of which are manual.

Figure 6:
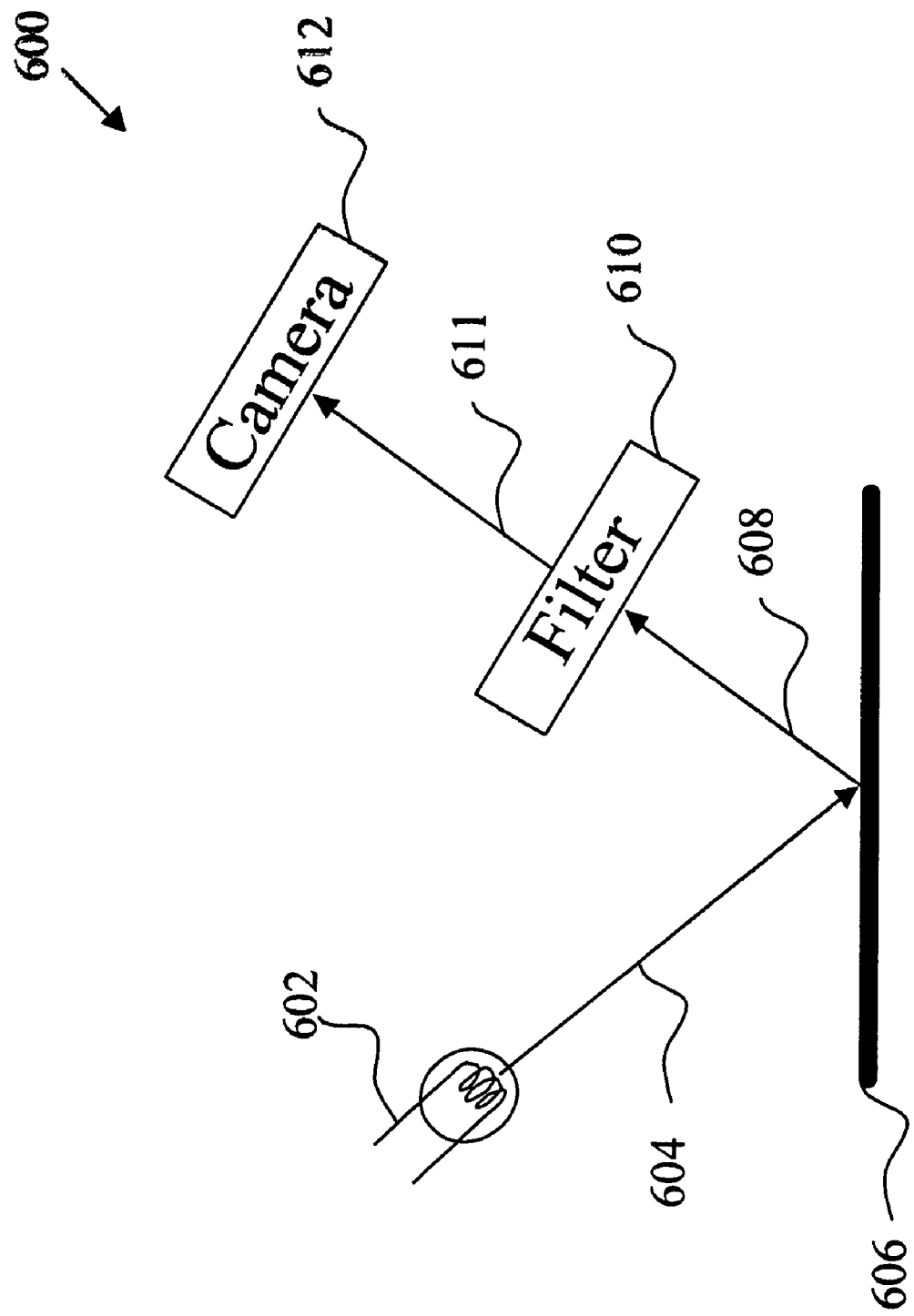
FIG. 6 is a diagrammatic representation of a system for selecting one or more wavelength ranges in accordance with one embodiment of the present invention.

In one embodiment, a low magnification microscope with a mechanism for selecting one or more wavelength ranges is provided. This tool also preferably uses one or more broadband sources with filters, with multiple sources covering different wavelength ranges, variable filters, etc. FIG. 6 is a diagrammatic representation of a system 600 for selecting one or more wavelength ranges in accordance with one embodiment of the present invention. As shown, the system 600 includes a broadband source 602 for generating a multiple wavelength incident light beam 604 towards sample 606. A multiple wavelength output beam 608 is scattered from the sample 606 in response to the incident beam 604. The system 600 also includes a filter 610 for selectively passing a portion of the output beam 611 based on wavelength to camera 612. In one implementation, the filter is configurable to pass particular colors, such as red, green, blue, or yellow. The camera is operable to generate an image based on the filtered output beam 611.

Measurements of overlay are taken by moving to a location on the sample where one or more of the targets in a target set are in the field of view of the microscope. An image is acquired and the intensity from some or all of the pixels in the image, which includes each individual target, are averaged or summed to give an intensity value for the target at a particular setting of the filter. In one embodiment, the filter is adjusted so as to give a maximum difference between targets. This may subsequently be normalized with respect to a reference surface, to the number of pixels summed, or corrected by a map of the illumination uniformity within the field of view. The sample or optics may then be moved until all of the necessary targets in a target set are measured. The overlay value is then determined using the intensity values in any of the above described scatterometry techniques, such as the linear approach by:

$$P1=(Ia-Ib) \text{ and } P2=(Ic-Id)$$

And:

$$\text{Overlay}=f0*(P2+P1)/(P2-P1)$$

This process could be repeated over multiple wavelength ranges to improve accuracy, precision, and robustness, wherein the wavelengths which result in the best contrast are used for the scatterometry analysis.

Because the magnification is low and the field of view is large compared to a typical imaging overlay tool and because an image of the area of the sample is collected, unlike a conventional reflectometer or ellipsometer, analysis of the image may be used to detect other types of processing problems by analyzing the image. For example, if the wrong reticle has been used for one or more processing steps, the image would be materially different. If the resist thickness were incorrect, the brightness or contrast of the image may be effected. If resist streaking were present, variation of brightness or contrast over the image may be detected. In CMP (chemical mechanical polishing) processes, processing errors such as over-polish, under-polish, etc. could be similarly detected.

In this embodiment, multiple scatterometry targets can be measured simultaneously, increasing the measurement speed. Additionally, processing errors or changes in processing conditions other than overlay can be detected without the need for a separate inspection tool.

Simultaneous, Multi-Angle Scatterometry

Techniques of obtaining scatterometric measurements may include the theta or 2-theta approach, in which scattering intensity from a grating or other repeating structure is measured at a plurality of angles by making multiple, sequential measurements. As the sample rotates through an angle of theta, the detector is generally rotated through 2-theta. Alternatively, the angles of the incident beam and detector system may be changed simultaneously. Use of the 2-theta approach is very slow, since multiple measurements are typically made. Use of multiple angle scanning scatterometry, such as a scanning angle of incidence system, requires mechanics which can accurately scan through a precise range of angles.

In a specific embodiment of the present invention, techniques and apparatus for simultaneous, multi-angle scatterometry are provided. Unlike the 2-theta approach, measurements are made with an apparatus which permits scattering intensity to be simultaneously determined for many angles. This technique is far faster than the 2-theta approach.

Figure 7:
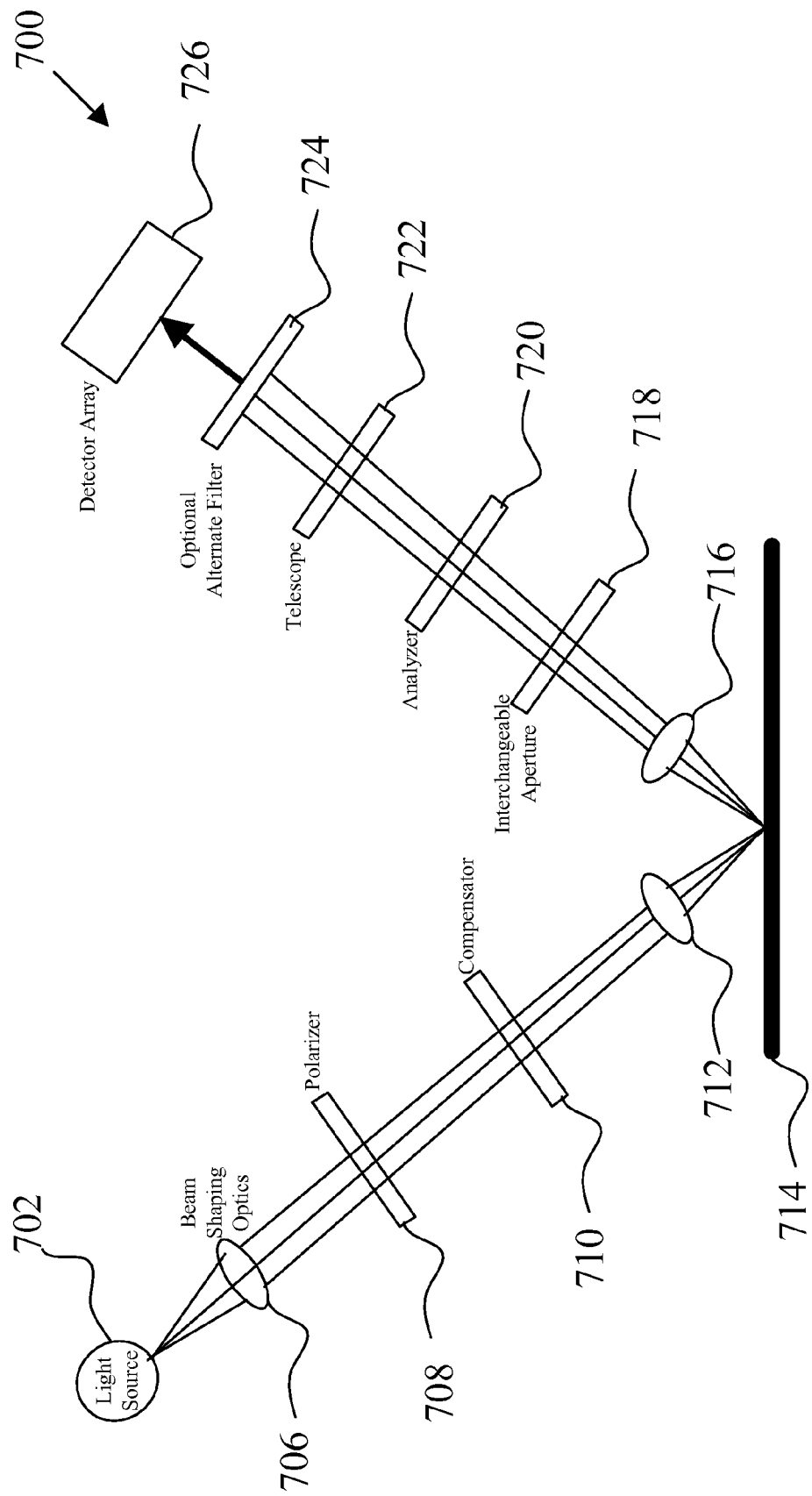
FIG. 7 is a diagrammatic representation of a simultaneous, multiple angle of incidence ellipsometer.

In order to implement this approach, an optical apparatus such as that shown in U.S. Pat. No. 5,166,752 by Spanier et al could be used. This patent is herein incorporated by reference in its entirety. In this patent, a multi-angle ellipsometer is shown in, for example, FIGS. 3 and 4 of the Spanier et al. patent. FIG. 7 is a diagrammatic representation of a simultaneous, multiple angle of incidence ellipsometer 700. As shown, the ellipsometer includes a source generator (e.g., components 702, 706, 708, 710, and 712) for directing polarized light onto the surface of sample 714, detection optics (e.g., components 718 through 724) for handling and detecting the output beam emitted from the sample, and a detector 726 for generating a signal related to the polarization state of the light reflected from the sample. The source generator includes a light source 702, a polarizer 708, a compensator 710 with a variable aperture, and a focusing lens system 712 simultaneously directing polarized light from a single beam of light from the light source onto the sample's surface at different angles of incidence. The source generator may also include an optional optical narrow band filter.

The lens system 712 has an effective aperture to focal length ratio for focusing the light on the sample 714 with angles of incidence which vary over a range of angles of at least one or two degrees. In a particular embodiment, the range of angles of incidence is about 30 degrees. Larger angles could be employed for directing rays at the sample 714.

The focusing lens system 712 focuses the polarized light which may be from a He—Ne laser for example, down to a single small spot or point on the sample 714. The different incident rays may have widely varying angles of incidence which are focused on a single, small spot on the sample 714. Thus, the light directed on the small spot on sample 714 contains rays at many angles of incidence above and below the angle of incidence of the central ray through the focusing lens. Each one of the incoming rays is reflected at an angle equal to its angle of incidence with the polarization state of each of the rays being altered by that reflection. A detector array 726 is employed to detect a plurality of rays reflected from the sample 714 individually over different, narrow ranges of angles of incidence to simply and quickly obtain data at a plurality of angles of incidence.

The output beam emitted from the sample 714 is directed through output lens 716, interchangeable aperture 718, polarization analyzer 720, and an optional alternate filter 724 onto detector array 726. The diameter d of the lenses 712 and 716 corresponds to their effective diameter. In the illustrated embodiment the lenses 712 and 716 each have a diameter d of 18 mm and a focal length 1 of 34 mm. Other effective lens diameters and focal lengths could be employed so long as a range of angles of incidence, preferably at least 30 degrees, is provided. The lens diameter and focal length are chosen with a view toward maximizing the number of angles of incidence of the light beams which strike the sample 714. In an alternative embodiment, light is transmitted through the sample rather than reflected from a surface of the sample.

The refocusing lens or lenses 716 directs the reflected (transmitted) light toward the detector array 726. However, a refocusing lens need not be employed as the reflected (transmitted) light could be made to directly impinge upon an array of detectors. It is preferable that the lenses 712 and 716 do not themselves alter the polarization state of the light.

The detector array 726 may be a linear, multiple element detector wherein each of the detector elements can detect a narrow range of angles of incidence of the rays that illuminate the sample. In the disclosed embodiment, the array 726 is a solid-state photosensitive detector array wherein the separate detector elements are all integrated on one circuit chip. Particularly, the detector elements comprise a linear array of photodiodes. While integrated on a single circuit chip, the individual photodiodes can function as separate detectors. The linear array of the disclosed embodiment comprises 128 detector elements arranged in a row to provide data for 128 different angles of incidence where the full array is illuminated by the reflected (transmitted) light. The number of individual detector elements could be more or less than that in the disclosed embodiment and the detector elements need not be integrated on a single chip but could be discrete detectors. By using a plurality of detector elements, it is possible to simultaneously detect the light reflected from the surface (or transmitted through the sample) for each of a plurality of different angles of incidence. It is also possible with the invention to employ a smaller number of detector elements which could be sequentially moved to mechanically scan the reflected (transmitted) rays for detection but this technique would require more time and could be less accurate, depending upon positioning accuracy.

The physical size of each of the detector elements is preferably less than the expanse of the reflected rays so that each element detects only a certain narrow range of angles of incidence on the illuminating side. The output of each of the detectors is used in a conventional manner as with real time computer techniques (e.g., via analyzer 720) to generate data in terms of $\Delta$ and $\Psi$ for each of those narrow ranges of angles of incidence. The data may then be used in any of the above described scatterometry approaches, as well as interpreted in a conventional manner. The linear array preferably runs in the plane of the optical system. In the disclosed embodiment, the long axis of the linear detector array 726 lies in the plane of incidence of the central ray and perpendicular to the central ray for detecting the maximum number of incidence angles. Alternatively, the compensator 710 could be placed after the sample 714 before analyzer 720 instead of, or in addition to, being located before the sample 714.

Such an ellipsometer could be used to illuminate a scatterometry target simultaneously over a range of angles, and an intensity of the scattered light is measured over a range of angles simultaneously with an array detector or the like. The signals acquired with a simultaneous, multi-angle system may be analyzed with a self-calibrating multi-target method such as the linear or phase-based methods described above.

By collecting data from the intensities measured at those angles, the parameters of the grating or other target can also be determined. For example, the data can be compared against theoretical models of data derived from techniques such as those mentioned by U.S. Pat. No. 6,590,656, issued Jul. 8, 2003, entitled "SPECTROSCOPIC SCATTEROMETER SYSTEM" by Xu et al, which patent is herein incorporated by reference in its entirety. The data can also be compared to theoretical models derived from techniques such as those mentioned by U.S. patent application, having application Ser. No. 09/833,084, filed 10 Apr. 2001, entitled "PERIODIC PATTERNS AND TECHNIQUE TO CONTROL MISALIGNMENT", by Abdulhalim, et al., which application is herein incorporated by reference in its entirety. This comparison can then be used to extract structure or target parameters from a database based on such comparison.

The model can also be adjusted based on such comparison. For instance, when the measured data significantly differs from the theoretical data, the model which was used to generate the theoretical data may then be adjusted so as to generate a more accurate value.

The data can be pre-generated and stored in libraries, or generated in real time during analysis. It is also possible, for techniques like scatterometric overlay, to directly compare measured spectra associated with various targets. Such differential measurements can then be used to determine overlay misregistration.

It would also be possible to perform this technique with a beam profile reflectometer such as that described in U.S. Pat. No. 4,999,014, issued 12 Mar. 1991, entitled "METHOD AND APPARATUS FOR MEASURING THICKNESS OF THIN FILMS" by Gold et al., which patent is incorporated herein by reference in its entirety.

An alternative embodiment of a simultaneous, multi-angle optical apparatus suitable for measuring scatterometry signals for overlay is an Optical Fourier Transform instrument described in SPIE Vol. 4299, pp279-290, (2001) by Obein, et al, which is incorporated herein by reference in its entirety. An implementation of this optical concept is the EZ-Contrast by ELDIM of Hérouville Saint Clair, France. A polarizer may be used to control the polarization of the incident beam. A polarizing element may be used to analyze the polarization of the scattered radiation before it reaches the detector or CCD. The resulting scatterometry signals may be analyzed with the linear algorithm or a phase detection algorithm described herein. The Optical Fourier Transform instrument may be configured to operate with a single wavelength, multiple wavelengths operating in parallel or in series, or with a Fourier transform modulation on the incident radiation.

Simultaneous Ellipsometry and Reflectometry

A system for employing a combination of ellipsometers and reflectometers may be employed to improve the accuracy of scatterometric measurements of overlay. In one embodiment, two or more ellipsometers are utilized as scatterometers to measure overlay. One of more of these ellipsometers could be spectroscopic ellipsometers. In another embodiment, two or more reflectometers are utilized as scatterometers to measure overlay. One of more of these reflectometers could be polarized reflectometers. Alternatively, a combination of one or more ellipsometers and one or more reflectometers are utilized as scatterometers to measure overlay.

Measurements can be performed serially (with each tool performing measurements at different times), in parallel (with all tools performing measurements substantially-simultaneously, or in any other arrangement (e.g., at least two but less than all of the tools performing measurements substantially-simultaneously).

In any of the implementations described herein, various tools may perform measurements at different angles of incidence, including near normally and obliquely, or both normal and oblique. That is, two or more of the following systems may be used together to achieve both a near normal incidence and one or more oblique angles: a spectroscopic near normal incidence reflectometer, a spectroscopic near normal incidence polarized reflectometer, a spectroscopic near normal incidence polarized differential reflectometer, an oblique incidence spectroscopic ellipsometer, and a spectroscopic oblique incidence polarized differential reflectometer.

In a specific implementation, at least two tools perform scatterometric measurements at substantially the same angle of incidence but from different directions. For instance, a first tool would be used for scatterometric measurements in the x direction, and a second tool would be used for scatterometric measurements in the y direction. Such a system could eliminate certain common scattered signals, with a corresponding increase in accuracy of measurements, and provide a symmetric configuration.

An advantage of employing a combination of such tools in scatterometric determination of overlay is that the accuracy of the measurements could be increased. Another advantage in using more than one tool and performing measurements at more than one angle (or point) of incidence is to help separate effects affecting the medium of interest (e.g., film effects) from overlay. For example, ellipsometer signals or polarization dependent signals from optical systems operating at normal or near-normal incidence have lower sensitivity to film thickness than at more oblique angles of incidence but have significant sensitivity to the overlay of scatterometry overlay targets. A further advantage is that combinations of ellipsometers and reflectometers already exist in current inspection tools. Another advantage of employing a combination of scatterometers configured to perform scatterometry measurements substantially in parallel on different targets or different target sections could be to reduce the total time required for measurement. Another advantage of a parallel measurement system could be to increase the signal acquisition time for each scatterometry overlay target and improve the measurement precision.

Scatterometric Overlay Determination Using FT Processing

A system for scatterometric measurement of overlay using fourier transform (FT) processing may also be utilized. In one embodiment, an interferometer is employed to modulate substantially all wavelengths of a broadband source, and the scattered radiation is detected with a CCD camera. Substantially all wavelengths of the modulation band are recorded for each pixel, or for groups of pixels. As the interferometer steps through the modulation band, a spectroscopic image of the scattered signal is produced.

The resulting spectroscopic image may have a relatively large field of view. For example, the image may include several multiple targets. The spectroscopic image could be processed on a pixel-by-pixel basis to accurately determine overlay while eliminating extraneous effects (e.g., film effects). Alternatively, processing could be performed using groups of pixels to improve speed and decrease processing resources. For example, a group of pixels from each target may be analyzed using any of the above described scatterometry processes. In a linear scatterometry approach, the images for each corresponding pair of targets is subtracted to obtain difference images D1 and D2. A characteristic, such as average intensity, of each difference signal is then obtained to result in P1 and P2, which are then used to determine the overlay error.

In a specific implementation, a Michelson interferometer is used to step through a wavelength modulation band. Alternatively, a Linnik interferometer, or any other interferometer, could be employed. For each position of the mirror, a CCD camera records the scattered signal intercepted in the field of view of the camera. The detected signals may then be digitized and stored on a pixel-by-pixel basis, or as groups of pixels. The magnitude of the steps is generally proportional with the accuracy of the overlay measurement. The speed of the camera (e.g., the number of fields per second that the camera can capture) is typically proportional with the speed of the measurement. Once the modulation band is spanned, the signal recorded for each pixel (or group of pixels) may be used as a basis for a discrete fourier transformation (or DFT). The DFT provides a spectral profile for each pixel (or group of pixels). Alternatively, the Fast Fourier Transform (FFT), Hadamard transform, or other known transform methods could be applied. Similarly, convolution or other mathematical methods could be used to determine the spectral profile. This spectral profile for each target may then be used in any of the scatterometry overlay techniques described above. Overlay determination can then be performed with increased accuracy.

Multiple Tunable Lasers

A system which has a combination of tunable lasers may be utilized to improve the accuracy of scatterometric measurements of overlay in combination with measurements performed by various configurations of ellipsometers and reflectometers. The tunable lasers provide radiation incident on the surface of interest. In one embodiment, scatterometric overlay measurements are performed using targets disposed in at least one layer of the design under consideration, and the tunable lasers provide radiation beams incident on the targets at multiple laser settings (e.g., at multiple wavelengths).

The measured signals may then be averaged together before or after processing. In one example linear scatterometry approach, measured radiation beams are obtained from targets A, B, C, and D. Two difference signals D1 and D2 from each pair of targets may then be obtained at multiple tunable laser settings. The signals measured from each target for each tunable laser setting may be averaged together prior to obtaining the difference signals D1 and D2. Alternatively, each set of differences signals for D1 and D2 may be averaged together to obtain a single average difference signal D1 and D2. Properties P1 and P2 of the difference signals D1 and D2 (e.g., integration) may then be obtained. In an alternative embodiment, multiple properties P1 and P2 are obtained for the different configurations of the tunable laser (without averaging the measured signals or the difference signals D1 and D2) and the results are averaged for each signal P1 and P2. The overlay error may then be obtained based on the signals P1 and P2 as described above. Alternatively, a phase scatterometry approach may be used by obtaining measured signals at multiple wavelengths from a plurality of targets.

Similarly, one ore more light emitting diodes covering one or more wavelength ranges might be used.

Scatterometric Overlay Determination Using Spatial Filtering

One embodiment expands on the above described embodiment for Scatterometric Overlay Determination using FT Processing.

A system for scatterometric measurement of overlay using FT processing in connection with spatial filtering is provided. More particularly, the signal reflected by at least one scatterometry target is selectively filtered spatially to only process particular signal components.

In the above described embodiment for Scatterometric Overlay Determination using FT Processing, an interferometer is employed to modulate substantially all wavelengths of a broadband source, and the scattered radiation is detected with a detector, such as a CCD camera. Substantially all wavelengths may then be recorded for each pixel, or for groups of pixels. As the interferometer steps through the modulation band, a spectroscopic image of any spatial portion of the scattered signal is produced. In the present example, where the scattered signal corresponding to a complete image (or a portion of an image) is collected, only a portion of the signal corresponding to a single line of pixels is retained. Alternatively, a portion of the signal corresponding to a plurality of pixel lines, but less than the whole image, is collected. Such a selective collection of the scattered signal can be achieved by spatially filtering the signal to only retain horizontal, vertical or oblique stripes of the signal corresponding to rows of pixels in the detector or CCD camera. Alternatively, a larger, more complete portion of the scattered signal could be collected at the CCD camera, but the information corresponding to undesirable rows of pixels (e.g., an edge of a target or a border between two targets) may be discarded subsequent to the collection.

The spectroscopic image corresponding to the retained signal may then be processed on a pixel-by-pixel basis to accurately determine overlay while eliminating extraneous effects (e.g., film effects). For instance, particular spatial portions of the scattered radiation may be blocked to remove particular frequency and/or phase information. Alternatively, processing could be performed using groups of pixels to improve speed and decrease processing resources. This embodiment provides higher SNR (signal to noise) over conventional processing methods.

In one implementation of the invention, any of the above described techniques to determine overlay in reference to the Scatterometric Overlay Determination using FT Processing embodiment may be used.

Compared to the embodiment for Scatterometric Overlay Determination using FT Processing, aspects of the embodiment for Scatterometric Overlay Determination Using Spatial Filtering may improve the processing speed and the throughput, while decreasing processing resources.

Examples of Spectroscopic Ellipsometers and Spectroscopic Reflectometers

Figure 8:
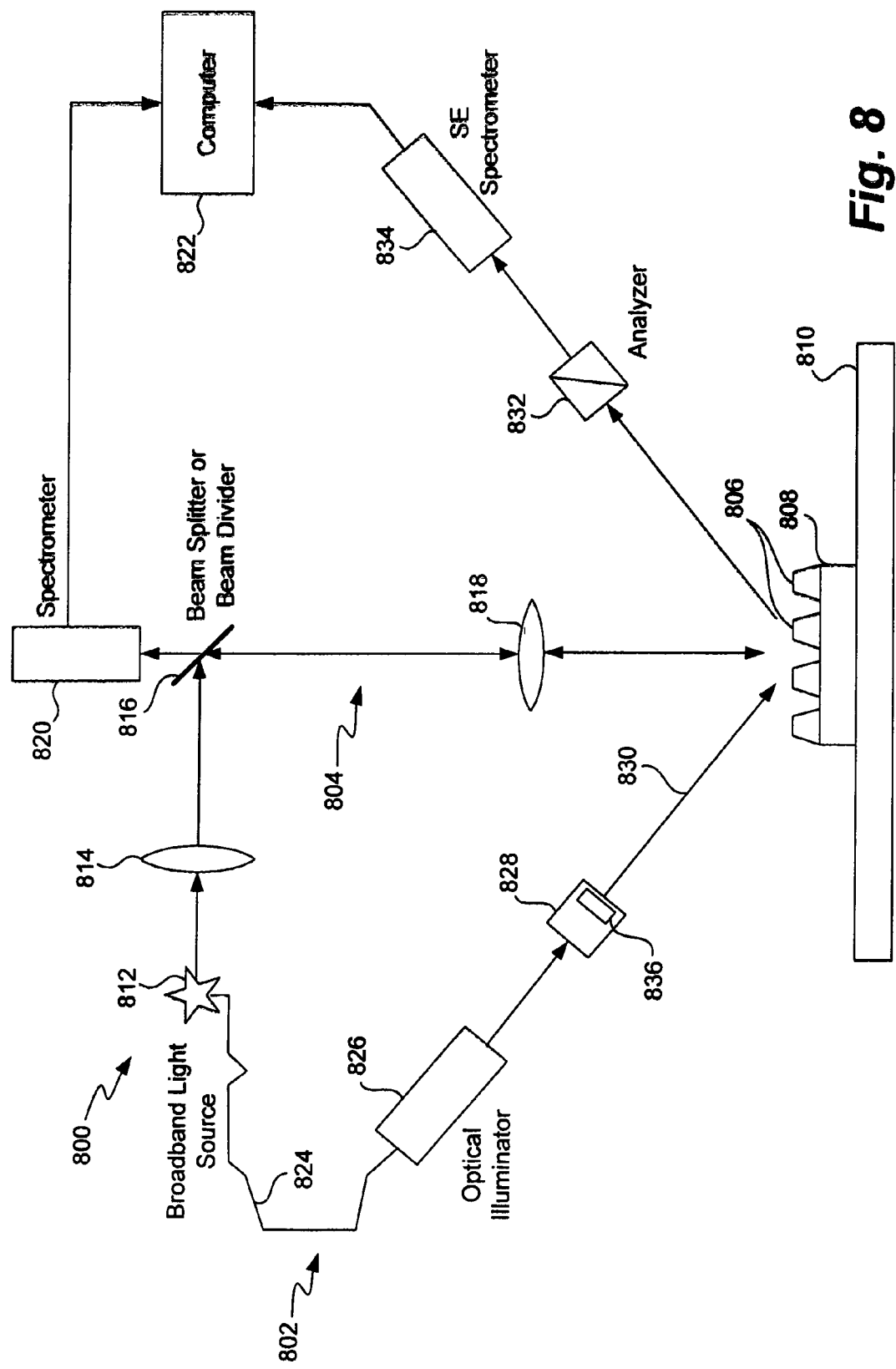
FIG. 8 is a schematic view of a spectroscopic scatterometer system in accordance with one embodiment of the present invention.

FIG. 8 is a schematic view of a spectroscopic scatterometer system 800, in accordance with one embodiment of the present invention. The system 800 combines the features of a spectroscopic ellipsometer 802 and spectroscopic reflectometer 804, each of which may be used for measuring overlay of a grating structure 806 disposed on a substrate or wafer 808. The grating structure 806, which is shown in a somewhat simplified format in the Figure, may be widely varied. The grating structure 806 may, for example, correspond to any of those grating structures described herein. Both the spectroscopic ellipsometer 802 and spectroscopic reflectometer 804 may utilize a stage 810, which is used for moving the substrate 808 in the horizontal xy directions as well as the vertical z direction. The stage may also rotate or tilt the substrate. In operation, the stage 810 moves the substrate 808 so that the grating structure 806 can be measured by the spectroscopic ellipsometer 802 and/or the spectroscopic reflectometer 804.

The spectroscopic ellipsometer 802 and spectroscopic reflectometer 804 also utilize one or more broadband radiation sources 812. By way of example, the light source 812 may supply electromagnetic radiation having wavelengths in the range of at least 230 to 800 nm. Examples of broadband light sources include deuterium discharge lamps, xenon arc lamps, tungsten filament lamps, quartz halogen lamps, and light emitting diodes (LEDs). Alternatively, one or more laser radiation sources may be used instead of or in combination with the broadband light source. In the case where the signal is collected at only one or a few wavelengths, the system may not be considered a spectroscopic ellipsometer but may be referred to as a single wavelength (or multi-wavelength) ellipsometer.

In the spectroscopic reflectometer 804, a lens 814 collects and directs radiation from source 812 to a beam splitter 816, which reflects part of the incoming beam towards the focus lens 818, which focuses the radiation onto the substrate 808 in the vicinity of the grating structure 806. The light reflected by the substrate 808 is collected by the lens 818, passes through the beam splitter 816 to a spectrometer 820.

The spectral components are detected and signals representing such components are supplied to the computer 822, which computes the overlay in any of the manners described above.

In the spectroscopic ellipsometer 802, the light source 812 supplies light through a fiber optic cable 824, which randomizes the polarization and creates a uniform light source for illuminating the substrate 808. Upon emerging from the fiber 824, the radiation passes through an optical illuminator 826 that may include a slit aperture and a focus lens (not shown). The light emerging from the illuminator 826 is polarized by a polarizer 828 to produce a polarized sampling beam 830 illuminating the substrate 808. The radiation emerging from the sampling beam 830 reflects off of the substrate 808 and passes through an analyzer 832 to a spectrometer 834. The spectral components of the reflected radiation are detected and signals representing such components are supplied to the computer 822, which computes the overlay in any of the manners described above.

In the spectroscopic ellipsometer 802, either the polarizer 828 or the analyzer 832 or both may include a waveplate, also known as compensator or retarder (not shown). The waveplate changes the relative phase between two polarizations so as to change linearly polarized light to elliptically polarized light or vice versa.

In order to collect more information about the interaction of the incident polarized light 830 with the sample, it may be desirable to modulate the polarization state of the light or modulate the polarization sensitivity of the analyzer or both. Typically this is done by rotating an optical element within the polarizer and/or analyzer. A polarizing element within the polarizer or analyzer may be rotated, or, if at least one of those assemblies contains a waveplate, the waveplate may be rotated. The rotation may be controlled by the computer 822 in a manner known to those skilled in the art. Although the use of a rotating element may work well, it may limit the system 802. As should be appreciated, the use of rotating elements may be slow, and because there are moving parts they tend to be less reliable.

In accordance with one embodiment, therefore, the polarizer 828 is configured to include a polarization modulator 836, such as photoelastic modulator (PEM), in order to produce a fast and reliable spectroscopic ellipsometer. The polarization modulator replaces the rotating waveplate. The polarization modulator 836 is an optical element that performs the same function as a rotating waveplate, but without the costly speed and reliability problems. The polarization modulator 836 allows electrical modulation of the phase of the light without mechanically rotating any optical components. Modulation frequencies as high as 100 kHz are readily attainable.

In an alternative embodiment, the analyzer 832 is configured to include a polarization modulator such as a PEM (Photoelastic Modulator) that can be modulated electrically. In yet another embodiment, both the polarizer and analyzer contain polarization modulators, such as PEMs, that are modulated at different frequencies.

Because the polarization modulator 836 can modulate at such a high frequency, the polarization modulator 836 may be used to perform various techniques, which would otherwise be too slow. For example, the difference between the polarized reflectivity of two structures may be obtained. To do this, a PEM may be combined with an acoustic optical modulator (AOM), where the AOM rapidly moves between the two structures while modulating the polarization state at a different (but related, such as multiple or submultiple) frequency. Signals at the sum and the difference of the PEM and AOM modulation frequencies contain useful information and can be detected with high signal-to-noise by synchronous detection. Alternatively the AOM on the incident beam could be used in combination with a PEM in the analyzer.

Although not shown, the rotating waveplate may also be replaced by a polarization modulator in other types of scatterometric systems as for example a polarization sensitive reflectometer.

Another optical system that may be used for scatterometry overlay measurements is a differential reflectometer or differential ellipsometer for detecting the +/−1 diffraction orders as described in the above referenced U.S. patent application Ser. No. 09/833,084 by Abdulhalim et al. which is incorporated herein by reference. One of the signals that may be analyzed is differential intensity $DS=(R_{+1}-R_{-1})/(R_{+1}+R_{-1})$. The signals may be measured from multiple scatterometry overlay targets with various offsets as described above. The resulting scatterometry signals may be analyzed with the linear algorithm or a phase detection algorithm described herein to determine the overlay.

Scatterometric Overlay Database

One aspect of the present invention provides a database of scatterometric overlay information that may be utilized for scatterometic overlay determination.

In one implementation, one or more database are provided which include one or more libraries of overlay information. The database information is then used in overlay measurements.

In one implementation, the libraries are compiled using predetermined test patterns with artificially-induced overlay. Alternatively, the libraries are produced using layer misregistrations programmed into the stepper. In another embodiment, the overlay that is induced or programmed has a progressive characteristic, varying within a particular range.

The information stored into the database may include overlay data regarding the actual overlay printed on the wafer, as induced via the test pattern or by the stepper. Alternatively or additionally, this information is obtained from overlay actually measured on samples. The database may further store scatterometry measurement records associated with the overlay data. Such scatterometry measurement records may be obtained by performing actual scatterometric measurements of the overlay data. The database may also include information regarding materials, process conditions, optical parameters, and other relevant data. The database information may be further enhanced by interpolation and other preprocessing.

The scatterometry database information may be utilized to improve the accuracy and speed of overlay measurements by retrieving scatterometry data associated with particular scatterometric measurements and process conditions recorded during actual measurements. In one implementation, theoretical overlay data which is generated using models and various target and optics configurations is recorded in a database. When overlay is measured on a particular set of targets, the measured overlay may then be matched to a particular theoretical overlay value. Target characteristics, for example, associated with the matching theoretical value may then be obtained.

Dynamic selection of a measurement algorithm or methods may also be provided based on database lookups. A further implementation utilizes the database to calibrate scatterometric overlay measurement tools before or during production line measurements.

Alternative Systems for Performing Scatterometry

According to various embodiments of the invention, acquisition of the spectra A through D (and of additional spectra if present) is performed using an optical apparatus that may comprise any of the following or any combination of the following apparatus: an imaging reflectometer, an imaging spectroscopic reflectometer, a polarized spectroscopic imaging reflectometer, a scanning reflectometer system, a system with two or more reflectometers capable of parallel data acquisition, a system with two or more spectroscopic reflectometers capable of parallel data acquisition, a system with two or more polarized spectroscopic reflectometers capable of parallel data acquisition, a system with two or more polarized spectroscopic reflectometers capable of serial data acquisition without moving the wafer stage or moving any optical elements or the reflectometer stage, imaging spectrometers, imaging system with wavelength filter, imaging system with long-pass wavelength filter, imaging system with short-pass wavelength filter, imaging system without wavelength filter, interferometric imaging system (e.g. Linnik microscope, e.g. Linnik microscope as implemented in the KLA-Tencor overlay measurements tools models 5100, 5200, 5300, Archer10, etc. available from KLA-Tencor of San Jose, Calif.), imaging ellipsometer, imaging spectroscopic ellipsometer, a scanning ellipsometer system, a system with two or more ellipsometers capable of parallel data acquisition, a system with two or more ellipsometers capable of serial data acquisition without moving the wafer stage or moving any optical elements or the ellipsometer stage, a Michelson interfereometer, a Mach-Zehnder interferometer, a Sagnac interferometer, a scanning angle of incidence system, a scanning azimuth angle system.

Additionally, the optical modules of any of the above described multiple optical module systems may one or more optical elements in common. For instance, a system with two or more polarized spectroscopic reflectometers capable of parallel data acquisition which share at least one optical element, with separate spectrometers or detectors for the radiation scattered from different targets (targets Ax and Cx, or Ax and Ay for example). Likewise, a system with two or more spectroscopic ellipsometers capable of parallel data acquisition may have at least one optical element in common, with separate spectrometers or detectors for the radiation scattered from different targets (targets Ax and Cx, or Ax and Ay for example). By way of another example, a system with two or more ellipsometers capable of parallel data acquisition may have at least one optical element in common, with separate spectrometers or detectors for the radiation scattered from different targets (targets Ax and Cx, or Ax and Ay for example).

Several embodiments of an interferometer based imaging spectrometer, as well as other types of imaging spectrometers such as filter based or the "push broom" approach, are described in U.S. Patent, having U.S. Pat. No. 5,835,214, issued 10 Nov. 1998, entitled "METHOD AND APPARATUS FOR SPECTRAL ANALYSIS OF IMAGES", by Cabib et al. System and Method embodiments for film thickness mapping with spectral imaging are described in U.S. Patent, having U.S. Pat. No. 5,856,871, issued 5 Jan. 1999, entitled "FILM THICKNESS MAPPING USING INTERFEROMETRIC SPECTRAL IMAGING", by Cabib et al. An alternative architecture for spectral imaging based on LED illumination is described in U.S. Patent, having U.S. Pat. No. 6,142,629, issued 7 Nov. 2000, entitled "SPECTRAL IMAGING USING ILLUMINATION OF PRESELECTED SPECTRAL CONTENT", by Adel et al. These patents are incorporated herein by reference in their entirety for all purposes.

The imaging spectrometer or reflectometer used for acquisition of the spectra A through D from the four targets (and of additional spectra if present) according to an embodiment of the invention may be of the Fourier transform imaging spectrometer type as is well understood by those skilled in the art. The imaging system of the Fourier transform imaging spectrometer should be capable of separating (resolving) the reflected or scattered light signals from the different targets (or sections of a compound scatterometry overlay target). Alternatively the imaging spectrometer or reflectometer used for acquisition of scatterometry overlay signals may use a two-dimension detector where one axis contains the spatial information from the different scatterometry overlay targets (or sections of a compound scatterometry overlay target) and the other detector axis contains spectrally resolved information from light spectroscopically separated with a prism system or diffraction grating system, for example or a system that is a combination of a prism and a grating. The illumination radiation may be wavelength selected prior to incidence on the target.

The spectra A through D obtained from the four targets (and additional spectra if present) detected in the imaging spectrometers, imaging reflectometers, or any of the other optical systems identified above in connection with various embodiments of the present invention may be unpolarized or selectively polarized. One or more of the unpolarized light or one or more of the polarization components of the reflected or scattered light from the targets may be detected with the imaging spectrometer or the imaging reflectometer.

In various implementations, separate detection systems may be used to separately or simultaneously record one or more of the following light signals: unpolarized reflected light, polarized light with the electric field substantially parallel to one major symmetry axis of one layer of the scatterometry overlay targets, polarized light with the electric field substantially perpendicular to one major symmetry axis of one layer of the scatterometry overlay targets, polarized light with the electric field at an angle to one major symmetry axis of one layer of the scatterometry overlay targets, right-hand circularly polarized radiation, left-hand circularly polarized radiation, and/or a combination of two or more of the previously listed polarization states. A separate detector system may be used to simultaneously record the signal from part of the light source for the purposes of light noise monitoring, and/or light level control, and/or light noise subtraction or normalization.

Various possible implementations of various embodiments of the present invention are illustrated in co-pending U.S. Provisional Application No. 60/449,496, filed 22 Feb. 2003, entitled METHOD AND SYSTEM FOR DETERMINING OVERLAY ERROR BASED ON SCATTEROMETRY SIGNALS ACQUIRED FROM MULTIPLE OVERLAY MEASUREMENT PATTERNS, by Walter D. Mieher et al. This provisional application is herein incorporated by reference in its entirety.

In one embodiment, each of the four targets (and additional targets if present) is illuminated by radiation produced by an optical system. The optical system may take the form of, among others, an optical source, a lensing system, a focusing system, a beam shaping system, and/or a directing system. In one embodiment, the radiation illuminating at least one of the targets is shaped as a radiation beam, with a relatively narrow beam cross section. In a particular implementation, the beam is a laser beam. The radiation illuminating the targets interacts with structures comprised within the targets and produces diffracted radiation components corresponding to each target and denoted as $S_A$, $S_B$, $S_C$, and $S_D$ (and additional signals if present). In one embodiment, the illuminating beam is a broadband polarized beam having a broad spectral range as is commonly used in spectroscopic ellipsometry. In one implementation, a focusing system may include one or more focusing mirrors.

2. Scatterometry Overlay Technique Alternatives:

Several related techniques are described in the above related co-pending U.S. Provisional Applications. These related techniques may be easily integrated with the techniques described herein.

In one embodiment of the invention, the targets (or compound scatterometry target sections) with different programmed offsets +/−F and +/−f0 as described above, or +/−F or other similar target combinations, are grouped together to enable simultaneous signal acquisition. In one implementation targets are arranged in a line to enable data acquisition while scanning the wafer or some or all of the optics in one direction along the array of scatterometry overlay targets. Arranging the targets in a linear array may also enable use of an imaging spectrometer or reflectometer, where one detector axis separates the signals from the different targets (or target sections) and the other detector axis detects the spectral information. In this case the imaging system images a linear or cylindrical image of the linear target array into the prism or grating system. The imaging spectrometer or imaging reflectometer may contain an array of two or more lenses (known to those skilled in the art as a lenslet array) to separate and direct the reflected or scattered light from different targets or target sections.

In one embodiment, the primary offset F is optimized to provide larger or maximum sensitivity to overlay errors. For instance, an offset F equal to ¼ of the pitch of the target provides high overlay sensitivity since it is half-way in-between the two symmetry points where overlay error sensitivity is minimum. The secondary offset f0 may be chosen such that the f0 is outside the region of interest for overlay measurements, such as equal to or beyond the specification limits, but it should not cause the uncertainty of the overlay measurement to allow the error that an out-of-spec measurement can be interpreted as within specifications. Nevertheless, this is not a limitation on the range of f0. A large f0 may decrease the accuracy of the overlay measurements for overlay errors E between −f0 and +f0. For overlay errors E larger than |f0|, the accuracy of the overlay measurement may be reduced due to extrapolation beyond the region −f0 to +f0 and the accuracy of the linear approximation may also be reduced.

Overlay measurements are most commonly done at or near the four corners of the stepper field (sometimes with an additional measurement near the center of the field) in 5 to 25 fields per wafer in semiconductor manufacturing processes. For a system of four targets used to determine overlay in the x direction and four targets used to determine overlay in the y direction, according to an embodiment of the present invention, a total of 8*4*5=160 measurements of scatterometry overlay targets may be used to determine the two dimensional overlay for a common overlay measurement sampling plan. More measurements may be conducted for more detailed sampling plans.

According to another embodiment of the invention, a total of six targets (three for x and three for y, for example) can be used to determine two dimensional overlay for the sample. This may facilitate further simplification of the overlay metrology process, reduction in processing resources, and decrease of the time used in the metrology process. In yet other implementations, additional targets or additional pairs of targets may be produced on the sample and used in a substantially similar manner with that described herein for determination of overlay based on scatterometry, but adjusted for the increased number of targets and corresponding number of diffracted radiation components. The mathematical methods for determination of the overlay error E can be similarly adjusted to exploit the availability of increased information provided by such additional targets or additional pairs, including by possibly accounting for higher order approximation terms in the formula for the overlay error E.

Scatterometric Overlay Determination with Limited Refocusing

To improve the accuracy of scatterometry overlay determination, more than one measurement is preferably carried out. One implementation utilizes a plurality of scatterometry overlay targets, and for each target, the system makes one scatterometric measurement of overlay. Another implementation utilizes a single scatterometric target, or a single scatterometric target area that comprises multiple target sub-regions, and more than one scatterometric overlay measurement is performed for that target or target area. In yet another embodiment, a plurality of targets or target regions are used, and more than one measurement is performed for some or all of the targets or target regions.

Conventionally, the optical system is refocused for each individual measurement. This, however, can consume a lot of time thus decreasing the processing speed of the system. For example, each focus sequence may take between 0.01 and 1 seconds, and each wafer may include between 30 to 70 sites with each site consisting of 8 targets. Using these numbers, refocusing may take up to as much as 560 seconds for each wafer. Considering there are typically 100 s and 1000 s of wafers to be inspected this number may be further increased to a completely unacceptable level.

In accordance with one embodiment of the present invention, therefore, multiple scatterometry overlay measurements are performed with limited optical refocusing in order to increase the processing speed and throughput of the system. By limited optical refocusing, it is generally meant that at least some new measurements are performed without refocusing the optical system, i.e., multiple measurements are made with the same focus setting. For instance, the optical system may be initialized with a focus setting that is optimized for a plurality of scatterometric measurements that will be performed, and no further refocusing takes place during these individual scatterometric measurements. The optimized focus setting may be found once for the entire wafer, or it may be found periodically. When periodic, the focus setting may be established at preset increments of time during inspection (e.g., every 30 seconds), for a particular location on the wafer (e.g., every 2×2 cm2 of wafer), for a particular characteristic of the target (e.g., similar line widths and spacing) and the like.

In one embodiment, the wafer includes a plurality of focus zones. Each of the focus zones is initialized with a focus setting that is optimized for all of scatterometric measurements that will be performed within the focus zone. Refocusing does not occur between individual scatterometric measurements inside the focus zone. As such, each target within the focus zone is measured with the same optimized focus setting. Any number of focus zones may be used.

The configuration of the focus zones may be widely varied. In one implementation, the focus zones correspond to a portion of the wafer. By way of example, the wafer may be broken up into plurality of radial focus zones emanating at the center of the wafer and working outwards, or into a plurality of angular focus zones, which separate the wafer into multiple quadrants. In another implementation, the focus zones correspond to a particular set of targets as for example, the targets at the corners of each semiconductor device. In another implementation, the focus zone corresponds to a particular target area that includes a plurality of targets (see for example 9A). In another implementation, the focus zones correspond to a particular target sub-region within the target areas (as for example the x or y directed group of targets shown in FIG. 9B). In yet another implementation, the focus zone corresponds to a particular sub region within the target itself.

A method of determining overlay will now be described. The method generally includes optimizing the focus setting of a first zone. The method also includes performing a first set of measurements on a plurality of targets within the first zone. Each of the targets within the first zone is measured using the optimized focus setting of the first zone. That is, a first target is measured, and thereafter a second target is measured without refocusing the optical system. Any number of targets can be measured in this manner. The method further includes optimizing the focus setting of a second zone. The method additionally includes performing a second set of measurements on a plurality of targets within the second zone. Each of the targets within the second zone is measured using the optimized focus setting of the second zone. That is, a first target is measured, and thereafter a second target is measured without refocusing the optical system. Any number of targets can be measured in this manner.

In one example of this method, the first and second zones may represent different target areas that include a plurality of targets (See FIG. 9A). In this example, each of the targets are located in close proximity to one another and therefore it can be assumed that variations in focus from one target to the next are minimal. The method generally includes optimizing the focus setting in the target area, and thereafter measuring each of the targets in the target area with the optimized focus setting. For example, the first target is measured, thereafter the adjacent target is measured, and so on without ever refocusing the optical system. When a first target area is measured, the system may repeat these steps on a second target area, as for example, a target area located at a different corner of the device.

In another example of this method, the first and second zones may represent sub regions with a target area that includes a plurality of targets. The sub regions may for example represent different target orientations (See FIG. 9B). The method generally includes optimizing the focus setting in the first sub regions (e.g., targets along the x axis), and thereafter measuring each of the targets in the sub region with the optimized focus setting. For example, the first target is measured, thereafter the adjacent target is measured, and so on without ever refocusing the optical system. When the first sub region is measured, the method continues by optimizing the focus setting in the second sub regions (e.g., targets along the y axis), and thereafter measuring each of the targets in the sub region with the optimized focus setting. For example, the first target is measured, thereafter the adjacent target is measured, and so on without ever refocusing the optical system. In another example the system is refocused prior to the measurement on the first scatterometry overlay target in an xy scatterometry overlay target group. After the scatterometry signal is measured for the first target in the xy overlay target group, the rest of the targets may be measured without refocusing. For example, an xy overlay target group comprises four scatterometry overlay targets for an overlay error determination in the x direction and four scatterometry overlay targets for an overlay error determination in the y direction.

Scatterometric Overlay Determination Using a Line Image

A system for scatterometric measurement of overlay using a one-dimensional line image may also be implemented. This embodiment allows a more efficient collection of light than techniques which utilize a two dimensional field of view which encompasses an area larger than the target areas. Additionally, optics may be used in the incident beam's path to provide a one dimensional profile for the light incident on the sample.

Figure 10:
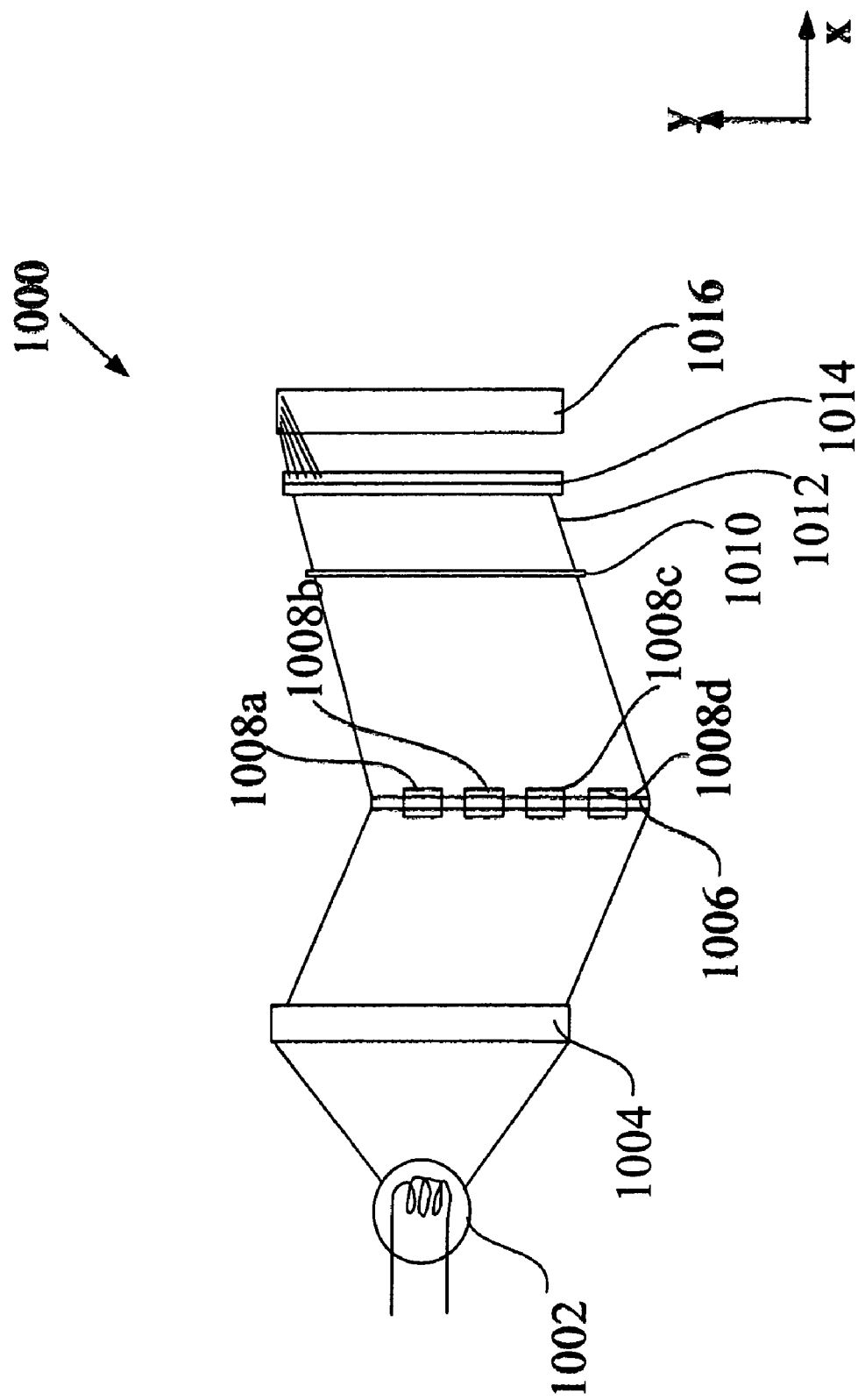
FIG. 10 is a diagrammatic top view representation of a system for obtaining a line image of a plurality of targets in accordance with one embodiment of the present invention.

FIG. 10 is a diagrammatic top view representation of a system 1000 for obtaining a line image of a plurality of targets 1008a-1008d in accordance with one embodiment of the present invention. As shown, a light source 1002 directs a beam towards cylindrical optics 1004 configured to illuminate a one-dimensional (1D) incident line 1006 of the targets 1008a-1008d. The light source and the incident optics are arranged so that the 1D incident line strikes at least a portion of all of the four targets. For example, the 1D line is incident on a line through the center of the four targets.

Light is then scattered or reflected from the targets in response to the incident line 1006 and some of the reflected light may pass through an optional slit 1010 to thereby form a 1D output beam having a 1D line profile 1012. The 1D output line then may be received by a dispersive element 1014, such as a prism or diffraction grating, which spreads or separates the output beam. In other words, the dispersive element 1014 acts to spatially resolve the output beam onto separate detector elements corresponding to different wavelength ranges or values. The separated output beams are then each received by a detector element of 2D detector array

1016. This implementation represents an efficient light delivery and collection mechanism since light is only directed to a narrow band of interest and the light collected is analyzed from this same narrow band of interest.

In one implementation, the detector array is formed from a plurality of detector elements arranged in a 2D array, such as a CCD camera. One dimension of the detector (e.g., the x direction) may receive separated output beams having different wavelengths, while the second dimension (e.g., the y direction) may receive dispersed output beams having different positions on the targets. For example, each element of a particular y direction column of the array 1016 receives a separated output beam having a particular wavelength and corresponding to a different position on the targets being imaged, while each element of a particular x direction row received a separated output beam having a different wavelength and a same target position.

Alternatively, the dispersive element 1014 may be omitted and a 1D detector may then be used to receive output beams at a plurality of 1D detector elements that each correspond to a different target position. In this embodiment, each detector element may average or integrate over different wavelengths and a same target position. In either case, different sets of detector elements may be grouped together as corresponding to a particular targets. For example, the elements in the y direction may be divided into four groups and each group corresponding to a particular one of four targets. An alternative to illuminating a single incident line is illuminating a larger area but only capturing scattered radiation along a detection line. In another implementation, the cylindrical optics 1004 may be removed from the incident path so that the incident image is two dimensional. The output beams are then passed through cylindrical optics to thereby form a 1D line image for the detector. A dispersive element with a 2D detector array may also be used as described above. Of course, a 1D detector array may also be implemented in this implementation.

The image captured by the detectors or camera can be processed at pixel level to determine overlay, possibly using the FT approach disclosed herein. Once overlay is measured along a particular incidence line, the wafer could be rotated by 90 degrees (or by any arbitrary angle) to measure overlay in a different direction. An advantage of the present invention is that overlay may be measured in more than one direction using a single optical system.

Algorithms

Various algorithms and methods for determining overlay may be combined for the purposes of refining and cross checking results. Also, pre-existing information (like CD or profile data) may be usefully integrated within these techniques:

In one example implementation of a combinational approach, a first calculation of overlay is performed according to a first technique (such as the differential method). A second calculation of overlay is then performed according to a second technique (such as a model-based regression). The results are then combined from the two calculations. The results may be combined in various ways. For example, one calculation may be used to cross check another. Or one calculation may be used to provide initial values to speed up the other calculation. Other combinations may also be used.

In a second combinational example, the speed and/or accuracy of an overlay measurement may be enhanced by making use of other measured data. For example, film thickness data from the layers making up the target may be fed into the algorithm. Providing film thickness or CD data as an input to the model-based regression program for overlay reduces the number of free parameters or provides better initial guesses for one or more of the free parameters in the regression thus speeding up the time to result. Such film thickness data could be measured using an appropriate tool, such as an ellipsometer or reflectometer. Alternatively (or additionally), CD data could be provided from an SCD measurement (scatterometry critical dimension or scatterometry profile measurement) and used to speed up or improve the accuracy of the scatterometry calculations. Other data from a scatterometry profile measurement could be similarly used, such as height or three dimensional profile information. Other sources of CD data, like a CD SEM, could be used.

In a specific implementation, a calculation of overlay is performed according to a first technique (such as the differential linear method or phase detection method). A second calculation of the structure of the target is then performed according to a second technique (such as a model-based regression) using the overlay result of the first method. For example, the overlay result of a differential or phase detection method may be used to adjust the model used in the second model-based regression technique so as to improve model accuracy. For instance, if a difference between the overlay error from the model-based regression technique and the overlay from the differential or phase detection technique is significant (e.g., greater than a predetermined value), then the model is adjusted. This method may speed up or improve the quality of the target structure calculation, for example, and may be advantageous for determining useful target structure information such as line width of the layer 2 structures, for example. Other combinations may also be used.

In yet another embodiment, the difference signal(s) may be calculated first and then the calculation of overlay is performed according to a second technique (such as a model-based regression). The difference signal(s) may be used in the second technique, e.g., the model includes difference signal(s) parameters. The difference signal is generally more sensitive to overlay and less sensitive to other non-overlay properties of the targets such as film thickness or feature profiles.

Combined Scatterometry and Imaging Targets and Uses of Combined Scatterometry and Imaging Data In an alternative implementation, the targets are designed for an imaging based overlay metrology application, as well as for the above described scatterometry analysis. In other words, the scatterometry and imaging target structures are tightly integrated so that scatterometry may be performed in conjunction with an image based overlay measurement. Preferably, the scatterometry target pairs are symmetrically positioned about the center of the field of view. If symmetry is preserved in the illumination and collection channels of the imaging system, tool induced shift will be minimized. By example, Xa and Xa' are twin (have similar magnitude but opposite sign offset) targets in the x direction. (Here Xa and Xa' may correspond to the targets Xa and Xd in FIG. 1). Likewise, Xb and Xb' are opposites. (Here Xb and Xb' may correspond to the targets Xb and Xc in FIG. 1). In the y direction, targets Ya and Ya' are opposites, while Yb and Yb' are opposites.

FIG. 11*a* is a top view representation of a first combination imaging and scatterometry target embodiment. In this example, the target arrangement includes a set of four x direction targets for determining overlay using scatterometry and a set of four y direction targets for determining overlay using scatterometry. The targets are laid out so that adjacent targets (with respect to the overlay measurement direction)

have an opposite offset. In the illustrated example, target Xa has an opposite offset than target Xa', and target Xb has an opposite offset than target Xb'. Likewise, targets Ya and Ya' have opposite offsets, and targets Yb and Yb' have opposite offsets. In this example, the targets also include structures which can be used for imaged based overlay determination.

In the illustrated example, the target arrangement includes a black border structure 1104 on a first layer and a gray cross-shaped structure 1102 on a second layer. Using image analysis methods, the center of the black structure 1104 may then be compared with the center of the gray structure 1102 to determine an overlay error (if any).

Although this set of targets have an overall rectangular shape which extends longer in the x direction than the y direction, of course, the targets could have other shapes (e.g., square or any symmetrical polygon) and/or extend longer in a direction other than x.

Figures 11B, 11C:
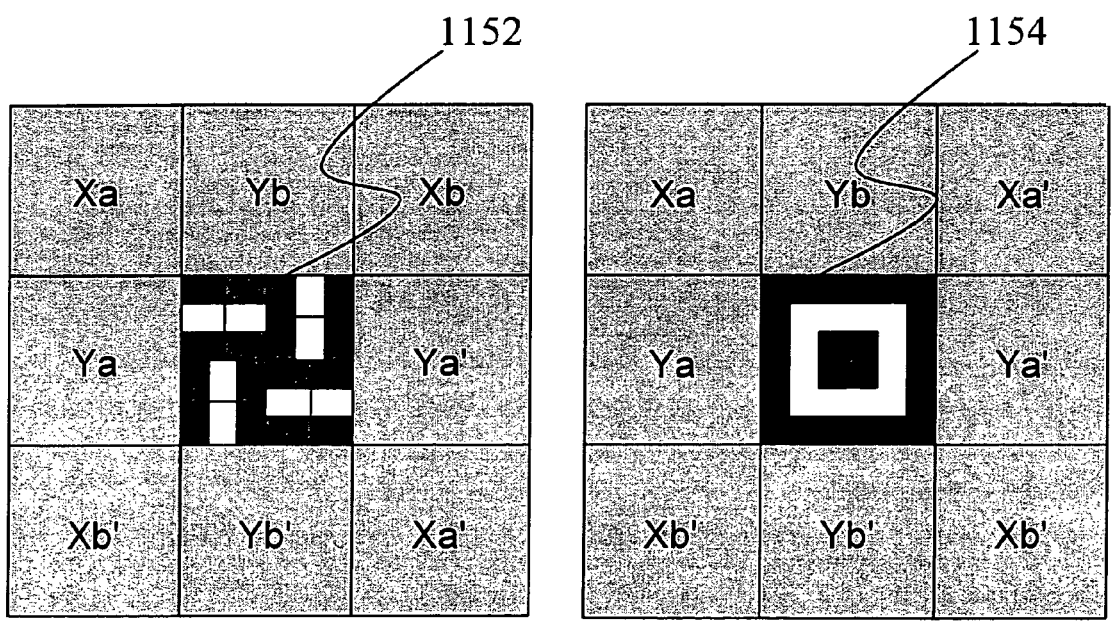
FIG. 11b is a top view representation of a second combination imaging and scatterometry target embodiment.
FIG. 11c is a top view representation of a third combination imaging and scatterometry target embodiment.

In other combinational target arrangements, the imaging structures are laid out in the center of a symmetrically arranged set of scatterometry targets. FIG. 11*b* is a top view representation of a second combination imaging and scatterometry target embodiment. As shown, scatterometry targets are symmetrically arranged around a central image type target 1152. In this example, the image type target 1152 is formed from quadrants of line segments, where each quadrant is either in the x or y direction. Suitable image type targets and techniques for determining overlay with same are described in the following U.S. patents and applications: (1) U.S. Pat. No. 6,462,818, issued 8 Oct. 2002, entitled "OVERLAY ALIGNMENT MARK DESIGN", by Bareket, (2) U.S. Pat. No. 6,023,338, issued 8 Feb. 2000, entitled "OVERLAY ALIGNMENT MEASUREMENT OF WAFER", by Bareket, (3) application Ser. No. 09/894,987, filed 27 Jun. 2001, entitled "OVERLAY MARKS, METHODS OF OVERLAY MARK DESIGN AND METHODS OF OVERLAY MEASUREMENTS", by Ghinovker et al., and (4) U.S. Pat. No. 6,486,954, issued 26 Nov. 2002, entitled "OVERLAY ALIGNMENT MEASUREMENT MARK" by Levy et al. These patents and applications are all incorporated herein by reference in their entirety.

FIG. 11*c* is a top view representation of a third combination imaging and scatterometry target embodiment. This target arrangement has scatterometry target symmetrically arranged around a box-in-box type target 1154. A box-in-box target generally includes a first inner box formed from a first layer surrounded by a second outer box structure formed in a second layer. The centers of the inner box structures may be compared to the center of the outer box structures to determine overlay error (if present).

The above targets may be imaged in any suitable manner (e.g., as described in the above referenced patents and applications by Bareket, Ghinovker et al., and Levy et al.) to determine overlay. The target arrangements may also be simultaneously or sequentially measured with any suitable optical tool as described herein to determine overlay using scatterometry techniques. In an alternative embodiment, the scatterometry targets may be simultaneously imaged along with the imaging type target structures. The resulting image may be subdivided into the separate scatterometry targets and then the scatterometry techniques applied to the image signals for each target (e.g., intensity).

The image may be obtained at the same time as, or before or after the scatterometry overlay measurements. Imaging overlay techniques may be used on the image. The imaging system may be a high-resolution microscope such as the system in the KLA-Tencor 5300 or Archer overlay measurement systems available from KLA-Tencor of San Jose, Calif. Alternatively, the imaging system may be a lower resolution imaging system used for other purposes that may include wafer alignment or pattern recognition.

Another use case analyzes overlay measurements where some of the overlay measurements on a sample (e.g., wafer or wafer lot) are obtained with imaging overlay metrology techniques and some of the overlay measurements are obtained with scatterometry overlay metrology techniques, which may follow the same or different sampling plans. In this general use case, the imaging overlay data may be obtained together on the same tool or on a different overlay tool as the scatterometry overlay data.

One advantage of measuring and analyzing both imaging and scatterometry overlay in the same wafer or lot is the utilization of the advantages of both techniques. For example, imaging overlay can currenlty be used on smaller targets than current scatterometry overlay technology. Satterometry overlay metrology tends to have better performance, such as better precision and likely better accuracy, than imaging overlay metrology. Scatterometry overlay metrology tend to have no associated tool induced shift (TIS), while imaging overlay metrology is associated with TIS. The acquisition time of imaging overlay data tends to shorter than acquiring scatterometry overlay due to the scatterometry targets having a larger relative size and the use of multiple targets in the scatterometry approach.

Imaging overlay metrology may be selected for specific targets of a wafer and scatterometry overlay metrology for other specific targets using any suitable criteria. Any combination of the criteria outlined below may be used to select scatterometry and/or imaging metrology for specific targets. In one embodiment, scatterometry metrology is used for the layers which have a tighter overlay budget. That is, scatterometry metrology is used for targets from the layers which have a low tolerance for overlay errors, such as the shallow trench isolation to poly layers. Imaging metrology may then be used for the layers which are noncritical or have looser overlay budgets or constraints.

Additionally, imaging or scatterometry metrology may be selected for particular targets based on analyzing the tradeoffs between performance versus throughput or wafer real estate. For instance, smaller targets may be used in tighter spaces such as in-chip, while larger targets are used larger spaces such as in the scribe lines or streets located between fields or dies, respectively. In one implantation, larger targets are distributed across the field of the lithography tool in the scribe line, while smaller targets are placed across the field within in the one or more dies. Scatterometry overlay may be used for the larger targets, e.g., in the scribe lines or streets, while imaging overlay is used for the smaller targets, e.g., that are located in-chip or within one or more dies. In one implementation, scatterometry metrology is used for targets within the scribe line (and/or streets), and imaging metrology is used for all other targets at other locations. Several embodiments for placing targets across the field either in-chip or in the streets or scribe lines are described in detail in co-pending U.S. Provisional Application No. 60/546,546, filed 20 Feb. 2004, entitled APPARATUS AND METHODS FOR DETERMINING OVERLAY AND USES OF SAME, by Mark Ghinovker et al., which application is incorporated herein by reference in its entirety for all purposes. In another implementation, overlay may be determined on two layer and simultaneous type targets as described in this provisional application. In one implementation, scatterometry metrology may be used for simultaneous or single layer targets, while imaging metrology is used for two layer targets, or visa versa.

Scatterometry metrology may also be performed on particular targets so as to facilitate calibration of the imaging overlay tool. That is, scatterometry overlay is obtained from specific sites, while imaging overlay is obtained from other sites. When scatterometry overlay differs significantly from the imaging overlay (more than a predefined value), operating parameters of the imaging tool may then be adjusted and scatterometry and imaging overlay obtained again until the scatterometry and imaging overlay data do not substantially differ (differs less than a predetermined value).

Scatterometry metrology may be associated with limited dynamic range, and accordingly, larger overlay errors may be missed by the scatterometry metrology. Thus, when overlay for a particular set of targets is expected to exceed the dynamic range limits of scatterometry metrology (or visa versa), imaging metrology may be used for such targets (or visa versa). Additionally, scatterometry may have problems with highly dense pitch patterns or targets, especially in the poly layer. In this scenario, imaging metrology may be used for highly dense targets that cause a problem for scatterometry, while scatterometry is used for more isolated (less dense) features. Alternatively, imaging overlay metrology may be found to have problems with density. In this case, scatterometry metrology would be used with highly dense features, while imaging is used-on isolated features.

In the future targets may be imprinted with a tool other than an imaging photolithography tool, such as an e-beam direct write lithography tool or a nano-imprint lithography tool. These different tools may have different sampling requirements or modalities. For instance, a tool may not have an associated field and corresponding sampling. In one example, an e-beam may directly "write" 100's of tiny targets. In this case, an imaging metrology tool may be used, while scatterometry metrology is used for targets formed from imaging lithography. In this scenario, a system which incorporates both imaging and scatterometry metrology is preferable so that the appropriate metrology may be quickly chosen for the different tool modalities.

In sum, both scatterometry and imaging overlay data may be usefully collected on a single sample, such as a wafer or wafer lot. The combined scatterometry and imaging overlay data may be used in various applications. In one application, the scatterometry and imaging overlay data are both used for lot deposition. When the scatterometry and/or the imaging overlay data is out of specification (e.g., the overlay errors are higher than a predetermined threshold), it may be determined that the current lot is out of specification or is likely to result in actual device faults. In this case, the lot may be reworked or thrown out.

In a process excursion use, the scatterometry and imaging overlay data may be used to determine whether the photolithography tool or process has deviated out of specification. In other words, the scatterometry and imaging overlay data is used to determine whether there is something wrong with the tool or process. In this use case, a special test wafer may be used to check the process or tool. Additionally, other processes and their respective tool's may be assessed via analysis of the scatterometry and imaging overlay data. When the scatterometry and imaging overlay data is out of specification (e.g., greater than a predetermined threshold), it may be determined that a problem has occurred in the process or tool and a root cause may then be investigated. By way of examples, problems of the lithography may include one or more of the following: resist thickness problems, scanner or stage alignment problems, lens movement alignment problems, focus or dose problems, and lens aberration.

The scatterometry and imaging overlay data may also be used to generate correctables for the particular lithography tool (e.g., stepper or scanner tool). In one implementation, the scatterometry and imaging overlay data are used to determine the dependency between overlay error and position (e.g., across the field). This dependency may be translated into parameters, such as translation, magnification, and rotation, for correcting the lithography tool.

Figure 11D:
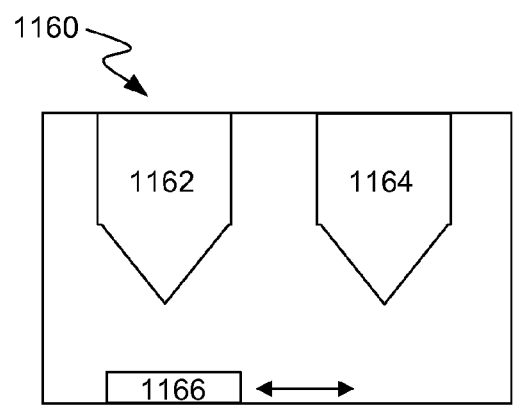
FIG. 11d illustrates a combinational imaging and scatterometry system in accordance with a first embodiment of the present invention.

Any suitable tool or combination of tools may be used to perform both imaging and scatterometry overlay. FIG. 11d illustrates a combinational imaging and scatterometry system 1160 in accordance with a first embodiment of the present invention. In this implementation, the imaging optical assembly 1162 is separate from the scatterometry optical assembly 1164. In other words, the imaging assembly 1162 is spatially separate from the scatterometry assembly 1164 and both assemblies are stand alone components. In this implementation, the assemblies 1162 and 1164 do not share any optical components, but are designed to compliment and collaborate with each other. For instance, overlay data may be passed between the two devices for implementation of one or more of the above described techniques on either assembly or on a separate processor (not shown).

The combination system 1160 also includes a stage 1166 for holding the sample thereon. The stage and the optical assemblies move in relation to one another so that the stage can be in a first position under the imaging optical assembly 1162 and in a second position under the scatterometry optical assembly 1164. The stage and/or the optical assemblies 1162 and 1164 may be coupled to a translational motor. Although a single isolation chamber and stage 1166 are shown for system 1160, the imaging and scatterometry assemblies may have their own stage and separate isolation chambers.

Any combination of the above described systems may also be used to obtain scatterometry and imaging overlay data.

Figure 11E:
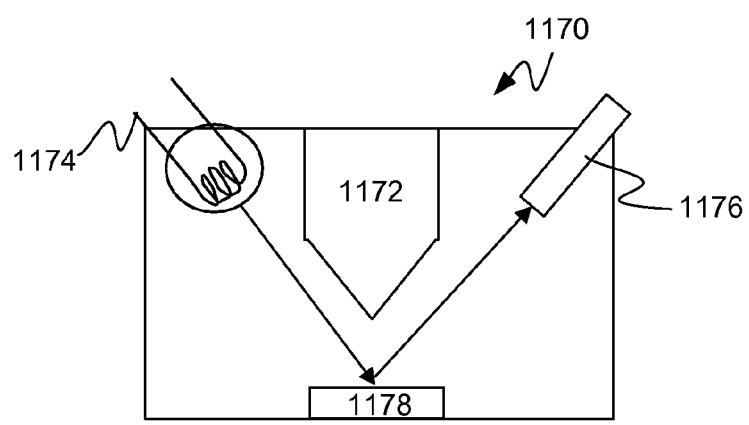
FIG. 11e illustrates a combinational imaging and scatterometry system in accordance with a second embodiment of the present invention.

FIG. 11e illustrates a combinational imaging and scatterometry system 1170 in accordance with a second embodiment of the present invention. In this implementation, the imaging and scatterometry optical assemblies are integrated together. The imaging and scatterometry optical assemblies may share one or more components. For example, the imaging and scatterometry assemblies may share a same light source. As shown, the combination system 1170 includes an imaging microscope 1172 configured for imaging overlay determination and light source 1174 for directing any form of optical beam towards a sample on stage 1178 and detector 1176 for measuring a resulting signal in response to the incident optical beam. For example, the imaging and scatterometry assemblies may share a same light source. The imaging and scatterometry assemblies may also be configured to share data, which may be analyzed in either assembly or by an independent processor (not shown).

Figure 11F:
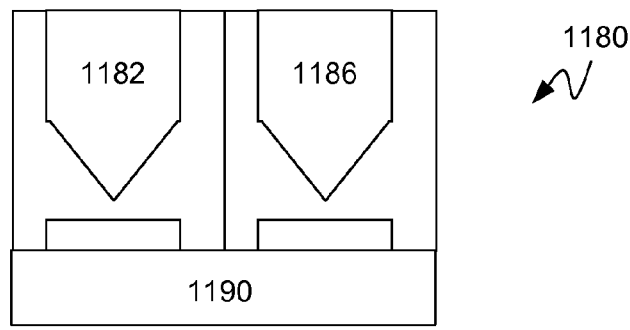
FIG. 11f illustrates a combinational imaging and scatterometry system in accordance with a third embodiment of the present invention.

FIG. 11f illustrates a combinational imaging and scatterometry system 1180 in accordance with a third embodiment of the present invention. This system 1180 is in the form of a cluster tool. As shown, the system 1180 includes a scatterometry module 1182 for obtaining and analyzing one or more scatterometry signals and an imaging module 1186 for performing imaging overlay determination. The system 1180 also includes a sample handling component 1190 for moving the sample between the two modules 1182 and 1186. The imaging and scatterometry assemblies may also be configured to share data, which may be analyzed in either assembly or by an independent processor (not shown).

The above described systems may contain any suitable components for performing imaging and scatterometry overlay determination. For instance, the imaging optical elements may be similar to the components of an Archer system from KLA-Tencor of San Jose, Calif. The scatterometry optical elements may be arranged like any scatterometry system elements described herein.

Mask Alignment During Imprint Lithography

Because the mask and sample are typically in close proximity (separated by the fluid to be polymerized) during nano-imprint lithography, the patterned surface of the mask, the fluid, and the patterned sample to be aligned to can be considered to be functionally equivalent to a scatterometry overlay target. The mask contains impression or depressions arranged in the shape of targets (as well as other structures) so that when the mask is pressed into the fluid, an impression that corresponds to the mask target shapes (and other structures) is formed in the underlying fluid. Also, a significant portion of the mask is transparent to allow radiation to pass there through onto the fluid to thereby make solidify the fluid and its impressions that were formed by the mask.

All of the methods, techniques and targets defined for scatterometry overlay would then be applicable to alignment procedures. In one embodiment, the measurement instrument projects radiation (preferably light) through the mask and onto an area of the mask and wafer which contains one or more scatterometry overlay targets. For example, the wafer may contain one or more targets on a first layer, while the mask contains one or more targets which will be used as second layer. The radiation is directed towards the mask targets and through a portion of the mask to the wafer targets.

The change in properties of the reflected light due to scattering or diffraction may then be used to determine the offset between the pattern on the mask and the pattern on the wafer. The wafer is then moved relative to the mask (or vice versa) to achieve the desired offset. A more accurate alignment may then be achieved, rather than with conventional alignment techniques such as direct imaging or moire techniques. The instrument could be a reflectometer, polarized reflectometer, spectrometer, imaging reflectometer, imaging interferometer, or other such instrument as described herein or in the above referenced provisional applications.

Disposition of Scatterometry Overlay Targets

The accuracy of scatterometry overlay systems can be improved by taking measurements at multiple targets located across the surface of interest. In one implementation, the scatterometry overlay system may utilize a plurality of scatterometry targets at various locations across the surface of interest and for each target the system may make one scatterometric measurement of overlay. In another implementation, the scatterometry overlay system may utilize a plurality of scatterometry target areas at various locations across the surface of interest. The scatterometry target areas comprise multiple targets, each of which can be measured by the scatterometry overlay system. By way of example, the scatterometry targets or scatterometric target areas may be located at the corners of one or more devices being formed on a wafer. In addition, the scatterometry targets may generally include a grating structure, which is measurable by the scatterometry overlay system.

The number of targets generally depends on the available space on the surface of interest. In most cases, the targets are placed in the scribe line between devices on a wafer. The scribe line is the place on the wafer where the wafer is separated into dies via sawing or dicing and thus the circuit itself is not patterned there. In cases such as this, the number of targets may be limited, at least in part, by the narrowness of the scribeline. As should be appreciated, the scribe lines tend to be narrow so as to maximize the amount of devices on the wafer.

In accordance with one embodiment of the present invention, the targets are strategically placed on the surface of interest in order to overcome any space constraints while increasing the number of targets. In one implementation, at least two targets are placed substantially collinearly in a first direction. For example, they may be placed collinearly in the x-direction or the y-direction. This arrangement may be useful when confronted with narrow spaces as for example scribe lines. In another implementation, multiple targets are disposed collinearly in multiple directions. For example, multiple targets may be disposed collinearly in both the x direction and the y-direction. This arrangement may be useful at the corner of a device as for example at the intersection of two scribe lines.

Although the examples given are directed at a Cartesian coordinate system as defined on the surface of interest, it should be noted that the coordinate system may be oriented arbitrarily on the surface or interest with the x and y axis being rotated or possibly interchanged. Alternatively or in combination with the Cartesian coordinate system, any other coordinate system may be used such as for example, a polar coordinate system.

FIG. 9A is a top view diagram of a scatterometric target area 900 having one or more targets 902, in accordance with one embodiment of the present invention. The scatterometric targets 902 are generally provided to determine the relative shift between two or more successive layers of a substrate or between two or more separately generated patterns on a single layer of a substrate. By way of example, the scatterometric targets may be used to determine how accurately a first layer aligns with respect to a second layer disposed above or below it or how accurately a first pattern aligns relative to a preceding or succeeding second pattern disposed on the same layer.

As shown in FIG. 9A, the scatterometric target area 900 includes at least two substantially collinear targets 902. By collinear, it is generally meant that the centers of symmetry for each of the targets 902 lie on the same axis 904. By way of example, the axis 904 may be aligned with a conventional coordinate system (Cartesian, polar, etc.) or some variation thereof. By placing the targets 902 collinearly, the scatterometric target area 900 does not take up as much width W and therefore may be placed in constrained places as for example in the scribeline of the wafer.

The targets 902 are generally juxtaposed relative to one another along the axis 904. In most cases, the juxtaposed targets 902 are spatially separated from one another so that they do not overlap portions of an adjacent target 902. Each of the targets 902 is therefore distinct, i.e., represents a different area on the substrate. This is typically done to ensure that each of the targets 902 is properly measured. The space 906 between targets 902 produces distortions in the optical signal and therefore it is excluded from the overlay calculation. The size of the space 906 is typically balanced with the size of the targets 902 so as to provide as much information as possible for the measurement of overlay. That is, it is generally desired to have larger targets 902 and smaller spaces 906 there between. The space 906 between targets 902 may be referred to as an exclusion zone.

The targets 902 may be widely varied, and may generally correspond to any of those overlay targets that can be measured via scatterometry. By way of example, the targets 902 may generally include one or more grating structures 908 having parallel segmented lines 910. Although not a requirement, the segmented lines 910 for the collinear targets 902 are generally positioned in the same direction, which may be parallel or transverse to the axis 904. In most cases, some of the segmented lines 910 are perpendicular to the axis 904 and some are parallel to the axis 904 to enable overlay measurements in x and y. Furthermore, the targets 902 may have an identical configuration or they may have a different configuration. Configuration may for example include the overall shape and size of the target 902 or perhaps the line width and spacing of the segmented lines 910 associated with the grating structure 908 contained within the target 902. Preferably the targets used for the overlay measurement in a particular direction, for example x direction, are designed to have the same configuration except for the programmed or designed overlay offsets.

The number of targets may also be widely varied. As should be appreciated, increasing the number of targets, increases the number of data collection points and therefore the accuracy of the measurement. The number of targets 902 generally depends on the overall size of the targets 902 and the space constraints in the direction of the axis 904. In the illustrated embodiment, eight side by side targets 902 are positioned within the scatterometric target area 900. A scatterometric target area may be equivalent to an xy scatterometry overlay target group as discussed above.

Using the above mentioned targets 902, scatterometric overlay measurements may be made sequentially, one target at a time, to measure overlay while eliminating effects due to variations in other sample parameters, such as film thickness. This can be accomplished via continuously scanning of the scatterometric target area (including for example the targets and the spaces there between) or by stepping to each of the targets. Alternatively, measurements may take place substantially simultaneously using two or more scatterometry signal beams for two, more than two, or all targets to increase throughput. The multiple scatterometry signal beams may come from more than one substantially independent scatterometry optical systems, or they may share much of the optical system, for example they may share the same light source, the same beam directing optics, or the same detector system.

Although the method described above includes placing the centers of symmetry for each of the targets substantially collinear, it should be noted that the centers of symmetry may be offset from the axis so long as a measurable portion of the targets still falls on the same axis.

Furthermore, although the method described above includes placing targets of similar orientation along the same axis, it should be noted that some of the targets may be positioned with a different orientation. For example, a first group of the targets 902 may have segmented lines positioned in the x dimension while a second group of the targets 902 may have segmented lines position in the y dimension.

Moreover, although the targets 902 are only shown positioned along a single axis 904, it should be noted that the targets may be positioned on multiple axis. For example, as shown in FIG. 9B, a first group of targets 902A may be disposed collinearly along a first axis 904A and a second group of targets 902B may be disposed collinearly along a second axis 904B. This implementation permits independent measurement of overlay in at least two directions. The first and second axis are typically transverse to one another and more particularly perpendicular one another. In the illustrated embodiment, the first axis 904A corresponds to the X-dimension while the second axis 904B corresponds the Y-dimension. Furthermore, each group consists of four targets 902. This implementation permits independent measurement of overlay in the X and Y directions.

Further still, although the targets have been described as having features (e.g., segmented lines) in substantially one direction, it should be noted that the targets may include features in more than one direction. In one implementation, for example, one or more of the collinearly positioned targets include features that permit scatterometric overlay measurement in first and second directions. By way of example, the features such as the segmented lines may be positioned in both the X and Y dimensions. In this case, the need for disposing targets along more than one axis as shown in FIG. 9B may be reduced or eliminated. That is, if each target has features that permit two-dimensional scatterometric measurements, overlay may be determined along both the X- and Y-axes using a single set of targets disposed substantially-collinearly along a single axis. Alternatively, one or more targets may include one or more sub-targets. If the sub-targets have features that permit two-dimensional scatterometric measurements, the number of targets desirable for a particular degree of measurement accuracy may be reduced, and the targets may be disposed along a single line.

Additionally, targets disposed along one or more axis may be used for measurement of more then one parameter. For example, a first set of targets may be used for scatterometric measurement of line width along the X-axis and a second set of targets may be used for scatterometric measurement of line width along the Y-axis. In an alternative implementation, scatterometric measurement of line width may be performed along the X-axis while spectral measurements are performed along the Y-axis.

Combined CD and Overlay Marks

Scatterometry measurement targets consume a significant area of the wafer for both metrology of CD and overlay. This wafer area becomes very valuable as design rule shrinks. Currently, scatterometry overlay marks may consume >35× 70 um space for each xy scatterometry overlay target group or mark on the wafer. These are used only for overlay measurements and therefore the wafer manufacturers consider the loss of wafer space as undesirable. Therefore, it is desirable to reduce the total wafer area required for measurement targets or measurement features. Changes to optical system design to enable measurements on smaller targets may result in greater complexity of the optical system and potentially compromise measurement performance. In scatterometry overlay measurement as describe herein, the target area typically consists of four gratings for each axis (X and Y). Each of these gratings is typically larger than 15×15 um with a limited opportunity to shrink it further using conventional techniques. Each grating is composed of a first layer grating (e.g. STI or shallow trench isolation) and a top layer grating (e.g. gate resist). One of the two layers has a programmed offset, which is typically smaller than the pitch of the top grating. In many cases the top layer is photoresist. An overlay measurement is achieved by analyzing the spectra of a reflected light from each of these gratings.

In scatterometry critical dimension (CD) or scatterometry profile measurement, the target area typically consists of a single grating or periodic structure, which may be positioned along either axis (X or Y). In some cases, the target area may include multiple gratings for each axis (X and Y). Each of these gratings is typically about 50×50 um. The measurement is typically performed on a single process layer target with no pattern underneath following completion of a L1 patterning step. This measurement is typically done on a photoresist pattern following a resist development step in a lithographic patterning process or following an etch or CMP process in other modules of the wafer fabrication process. A CD or scatterometry profile measurement is achieved by analyzing the spectra of a reflected light from the grating(s) as described in the above referenced U.S. Pat. No. 6,590,656 by Xu, et al.

In accordance with one embodiment of the present invention, the scatterometry CD marks and the scatterometry overlay marks are combined to enable the fab to save wafer space and to print larger scatterometry overlay marks with no impact on the wafer scribe-line. The combined mark is constructed with a scatterometry CD target (which is one continuous grating taking area of 4 scatterometry overlay gratings) as the first layer and scatterometry overlay target patterns (with corresponding shifts regarding to the first layer) as the top layer. This results in zero or minimal additional scribe line space allocated to scatterometry overlay.

Figure 12:
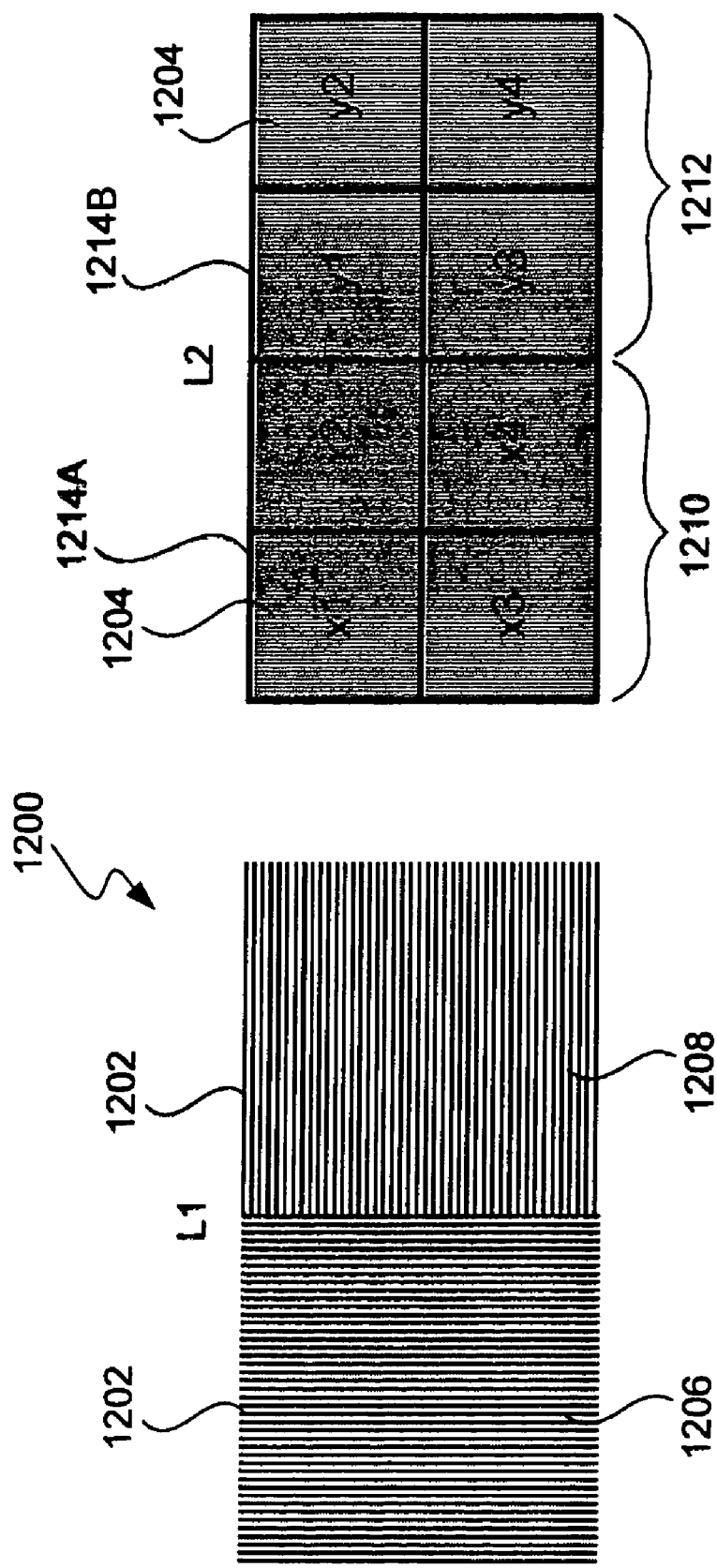
FIG. 12 is a diagram of a combined mark, in accordance with one embodiment of the present invention.

FIG. 12 is a diagram of a combined mark 1200, in accordance with one embodiment of the present invention. The combined mark 1200 provides for both scatterometry CD measurement and scatterometry overlay measurement at different steps in the wafer manufacturing process. The combined mark 1200 is formed on at least two layers of the wafer, particularly a first layer L1 and a top layer L2. The first layer L1 includes scatterometry CD/profile targets 1202 and the top layer L2 includes scatterometry overlay targets 1204. Although shown as separate layers in the diagram, it should be noted that the scatterometry overlay targets 1204 are built on (over) the scatterometry CD profile targets 1202. The scatterometry CD/profile targets 1202 form an L1 scatterometry CD mark, which can be measured to determine CD after formation or processing of the L1 pattern. The scatterometry overlay targets 1204 cooperate with the scatterometry CD/profile targets 1202 to form an L2-L1 scatterometry overlay mark, which can be measured to determine overlay between the layers after formation of the L2 pattern (which comes after L1 pattern formation). As should be readily apparent, this method may be repeated to produce a layer 2 L2 scatterometry CD/profile target(s) followed by a Layer 3 L3 pattern to create an L3-L2 scatterometry overlay mark or target area.

The configuration of the scatterometry CD/profile targets 1202 and scatterometry overlay targets 1204 may be widely varied. In the illustrated embodiment, the scatterometry CD/profile targets 1202 disposed on L1 include a first grating 1206 oriented in a first direction and a second grating 1208 oriented in a second direction. The first direction may be orthogonal to the second direction. By way of example, the first grating 1206 may include vertical lines while the second grating 1208 may include horizontal lines. In addition, the scatterometry overlay targets 1204 disposed on L2 include a first group of gratings 1210 and a second group of gratings 1212. Both the first and second groups of gratings 1210, 1212 include one or more gratings 1214. The number of gratings 1214 may be widely varied. In one implementation, both the first and second groups 1210 and 1212 include four gratings 1214. The gratings 1214A in the first group 1210 are oriented in the first direction, and the gratings 1214B in the second group 1212 are oriented in the second direction. By way of example, the gratings 1214A in the first group 1210 may include vertical lines while the gratings 1214B in the second group 1212 may include horizontal lines.

In order to produce an L2-L1 overlay mark, the first group of gratings 1210 is positioned over the first grating 1206 of the CD/profile targets 1202, and the second group of gratings 1212 is positioned over the second grating 1208 of the CD/Profile targets 1202. This places gratings with similarly directed lines together, i.e., vertical lines with vertical lines and horizontal lines with horizontal lines. The first group of gratings 1210 cooperates with the first grating 1206 of the CD/profile targets 1202 and the second group of gratings 1212 cooperates with the second grating 1208 of the CD/profile targets 1202. The alignment between layers is determined by the shift produced between the corresponding lines of these cooperating structures. The vertical lines, for example, may be used to determine X overlay and the horizontal lines, for example, may be used to determine Y overlay. In an alternative embodiment, L1 or L2 pattern may be periodic structures comprised of line segments, cylindrical holes or features (contact or via holes in resist or filled contacts, for example), device-like structures, and the like.

Although the first and second gratings 1206 and 1208 of the CD mark are shown together, it should be noted that they may be placed apart. When implemented apart, the first group of gratings 1210 and the second group of gratings 1212 would also be placed apart, i.e., the first group of gratings 1210 goes with the first grating 1206 and the second group of gratings 1212 goes with the second grating 1208.

The advantages of combining overlay and CD marks are numerous. Different embodiments or implementations may have one or more of the following advantages. One advantage of combining marks is in the ability to reduce the need for additional wafer space for scatterometry overlay targets. Another advantage is that larger scatterometry overlay targets may be allowed if they do not require as much additional scribe line space. Larger scatterometry overlay targets may make optical design or optics manufacturing easier and may provide better scatterometry overlay metrology performance than on smaller scatterometry overlay targets.

Combination of Scatterometry Overlay and CDSEM

The purpose of this embodiment is to enable measurement of critical dimensions on a semiconductor wafer with an electronic microscope (CD-SEM) and measurement of overlay using scatterometry on the same measurement system or using linked measurement systems sharing at least part of a robotic wafer handling system. The established methods of measuring critical dimensions and overlay commonly require scheduling and operating separate measurement systems. One disadvantage of the established methods of measuring critical dimensions and overlay on separate measurement systems is the additional time required to schedule and run separate operations on separate metrology tools. Another disadvantage is the redundancy of common parts and the costs associated therewith.

In order to overcome these disadvantages, a metrology system that combines Scatterometry Overlay and CDSEM may be provided. In one embodiment, a scatterometry overlay measurement (SCOL) system is integrated with a CDSEM system such that the CDSEM and SCOL systems share at least part of the robotic wafer handling system and/or data systems. Alternatively, the CDSEM and the scatterometry overlay systems may be separate systems capable of independent operation, but linked in such a way that they share at least part of a robotic wafer handling system.

In operation, a wafer, a group of wafers, or batch of multiple wafers may be introduced to the combined metrology system by loading the wafer container onto the robotic wafer handling system dedicated to this combined metrology system. Measurement recipes may be selected specifying CDSEM measurements on some or all of the wafers and scatterometry overlay measurements on some or all of the wafers. The CDSEM measurements and the SCOL measurements may be specified together in one or more recipes, or may be specified in separate recipes. The CDSEM and SCOL measurements may be done on the same wafers or on different wafers or on some of the same wafer and some different wafers. The CDSEM and SCOL systems may operate in parallel, or in series.

One example of the combined metrology system would be integration of a scatterometry system capable of scatterometry overlay measurements (such as a spectroscopic ellipsometer, spectroscopic polarized reflectometer, or +/31 1 order diffraction scatterometer) inside a CD-SEM such as any of those manufactured by KLA-Tencor of San Jose, Calif. Another example of a combined metrology system would be a linked system comprising a scatterometry overlay system, a CDSEM such as any of those manufactured by KLA-Tencor of San Jose, Calif., a robotic handler, and a wafer scheduling system. Communication to factory automation and/or factory information, and/or factory process control systems may be through separate communication or automation systems or may be at least partially or completed shared.

One advantage of the combined CDSEM and SCOL metrology system is the reduction in overall time required to complete scheduling and/or performing the CDSEM and scatterometry overlay measurements. At least one queue delay time may be eliminated. Performing CDSEM and overlay measurements in parallel can save at least part of the time required for separate measurement operations.

FIGS. 13A-13D show variations of a combined metrology tool 1300, in accordance with several embodiment of the present invention. In all the figures, the combined metrology tool 1300 includes a robotic wafer handling system 1302, a critical dimensioning scanning electron microscope (CD-SEM) 1304, a scatterometry overlay (SCOL) measurement instrument 1306, a wafer load position A 1308 and a wafer load position B and 1310, respectively. The robotic wafer handling system 1302 is configured to transfer wafers to and from the CD-SEM 1304 and SCOL measurement instrument 1306 as well as to and from the wafer load positions A and B 1308 and 1310. The critical dimensioning scanning microscope 1304 is configured to measure the critical dimensions that may include, for example, linewidth, top linewidth, via diameter, sidewall angle and profile. The scatterometry overlay measurement instrument 1306 is configured to measure the overlay as for example between two layers disposed on the wafer. The wafer load position A and wafer load position B are configured to hold one or more wafers. In most cases, they hold a plurality of wafers. The wafers may be from the same lot or from a different lot.

Figure 13A:
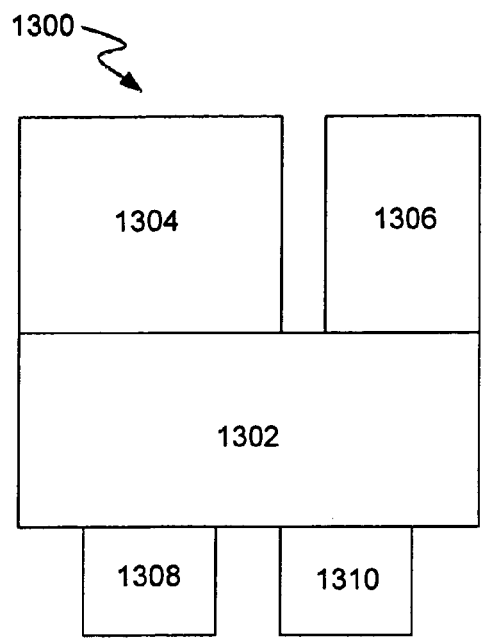
FIGS. 13A-13D show variations of a combined metrology tool, in accordance with several embodiments of the present invention.
Figure 13B:
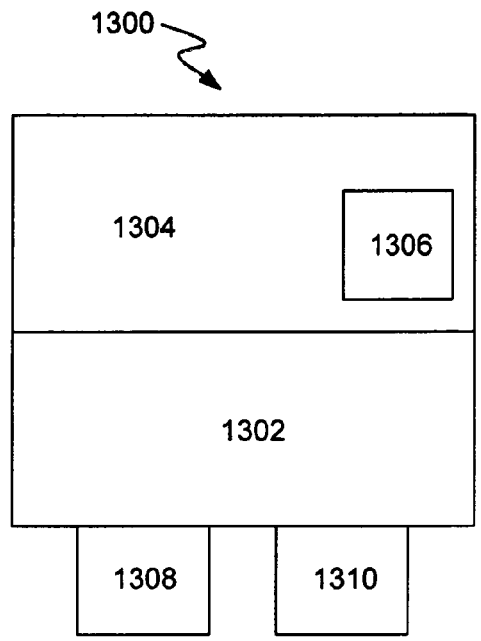
Figure 13C:
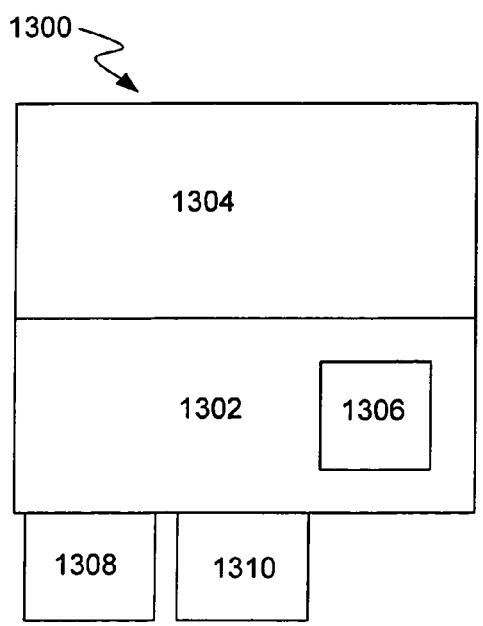
Figure 13D:
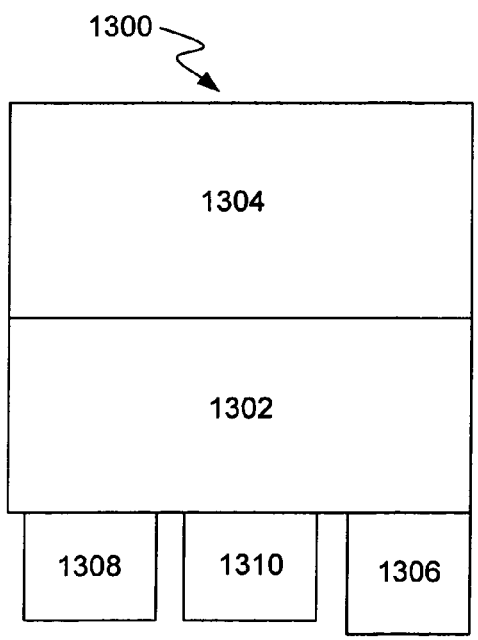

In FIGS. 13A and D, the CD-SEM 1304 and the SCOL measurement instrument 1306 are separate systems that are integrated via the robotic wafer handling system 1302. In FIG. 13B, the SCOL measurement instrument 1306 is integrated into the CDSEM 1304. In FIG. 13C, the SCOL measurement instrument 1306 is integrated into the robotic wafer handling system 1302.

In one operation, some of the wafers from wafer load position A and/or B have critical dimensions measured at the CD-SEM and thereafter have overlay measured at the scatterometry overlay measurement instrument. The wafer can be measured by both processes without being removed from the system, i.e., the wafer handling as well as the throughput issues associated therewith are reduced. In another operation, some wafers from wafer load position A and/or B have critical dimensions measured at the CDSEM and some other wafers from wafer load position A and/or B have overlay measured on SCOL measurement instrument. In any of these operations, the CDSEM and SCOL measurement instrument can proceed independently and simultaneously.

Figure 14:
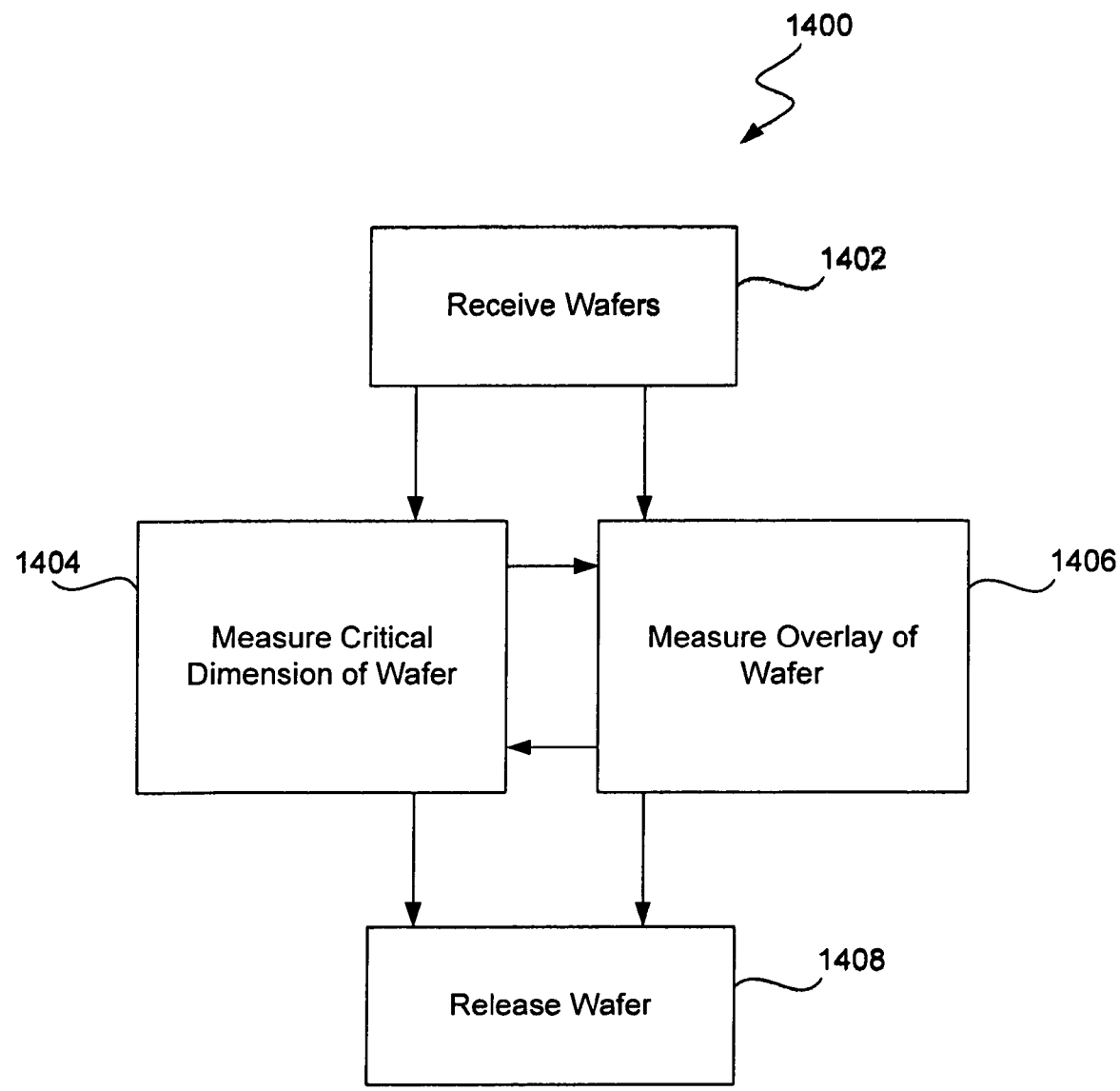
FIG. 14 is a flow diagram using a combined metrology tool, in accordance with one embodiment of the present invention.

FIG. 14 is a flow diagram 1400 using a combined metrology tool, in accordance with one embodiment of the present invention. The method generally includes step 1402 where a group of wafers are received by the metrology tool. By way of example, the wafers may be a wafer lot that is loaded at position A in FIG. 13. Following step 1402, the process flow 1400 proceeds to step 1404 where the critical dimensions of a wafer from the group of wafers is measured. By way of example, the critical dimension measurements may be performed by a CDSEM as for example the CDSEM shown in FIG. 13. The process flow 1400 also proceeds to step 1406 where the overlay of a wafer from the group of wafers is performed by a SCOL measurement instrument as for example the instrument shown in FIG. 13. Steps 1404 and 1406 may be performed at the same time on different wafers. Steps 1404 and 1406 may be performed on the same wafer in a sequence of operations, as for example, from CD to overlay or from overlay to CD. The transferring of the wafer may for example be performed by the robotic system shown in FIG. 13. When all the measurements are performed, the process flow proceeds to step 1408 where the group of wafers are released from the metrology tool.

Uses of Scatterometry Overlay Data

The overlay results obtained with scatterometry overlay techniques described herein, including the linear differential method and phase-detection algorithms, may be used to calculate corrections to the stepper settings to minimize overlay error. These calculated corrections for lithography steppers or scanners are commonly referred to as "stepper correctables." The stepper correctables obtained from scatterometry overlay measurements may be used as inputs to the stepper to minimize overlay error for subsequent wafer processing. The overlay errors or stepper correctables obtained from scatterometry overlay may be input to an automated process control system which may then calculate a set of stepper corrections to input to the stepper to minimize the overlay errors for subsequent wafer processing. The overlay errors, stepper correctables, or calculated worst overlay errors on the wafer obtained with scatterometry overlay may be used to disposition product wafers to decide if the wafer requires rework or meets overlay requirements for further wafer processing.

Combination of Scatterometry Overlay and other Metrology or Inspection Methods

Scatterometry overlay may be combined with scatterometry profile or scatterometry critical dimension systems, or other semiconductor metrology or inspections systems. Scatterometry overlay may be integrated with a semiconductor process tool, for example a lithography resist process tool (also known as a resist track). Integration of metrology systems with process systems and combinations of metrology systems are described in (1) U.S. patent application, having patent Ser. No. 09/849,622, filed 4 May 2001, entitled "METHOD AND SYSTEMS FOR LITHOGRAPHY PROCESS CONTROL", by Lakkapragada, Suresh, et al. and (2) U.S. patent, having U.S. Pat. No. 6,633,831, issued 14 Oct. 2003, entitled "METHODS AND SYSTEMS FOR DETERMINING CRITICAL DIMENSION AND A THIN FILM CHARACTERISTIC OF A SPECIMAN", by Nikoonahad et al, which applications are incorporated herein by reference in their entirety.

Scatterometric Overlay with Crossed Gratings

Scatterometry overlay line targets with L1 and L2 line elements perpendicular to underlying line grating L0 (or any number of underlying gratings). In this case the scatterometry overlay signal is not sensitive to the positions of L1 and L2 with respect to L0. One advantage is to reuse wafer area already used for scatterometry profile targets in a previous process layer. For example, targets for determining overlay in two different sets of layers can be stacked atop one another.

In another embodiment, scatterometry overlay line targets with L1 and L2 line elements perpendicular to underlying line grating L0 where L0 is one or more material(s) (copper damascene structure, for example), where the L0 pitch and line width are such that the scattered signal is substantially less sensitive (over at least part of the spectrum or signal conditions) to structures (e.g. film thickness or other structures) beneath L0 than would be the case in the absence of L0, are used. One example of an L0 structure that has these properties is a copper damascene line grating with 200 nm pitch, 100 nm line width, and 500 nm height. Proper choice of pitch, line width, etc. can produce a L0 structure that screens the underlying structures and produces a signal that is less sensitive to underlying features for at least some signal wavelengths, polarizations, etc. Optical simulations may be used to determine the preferred L0 properties including pitch and line width.

Figure 15:
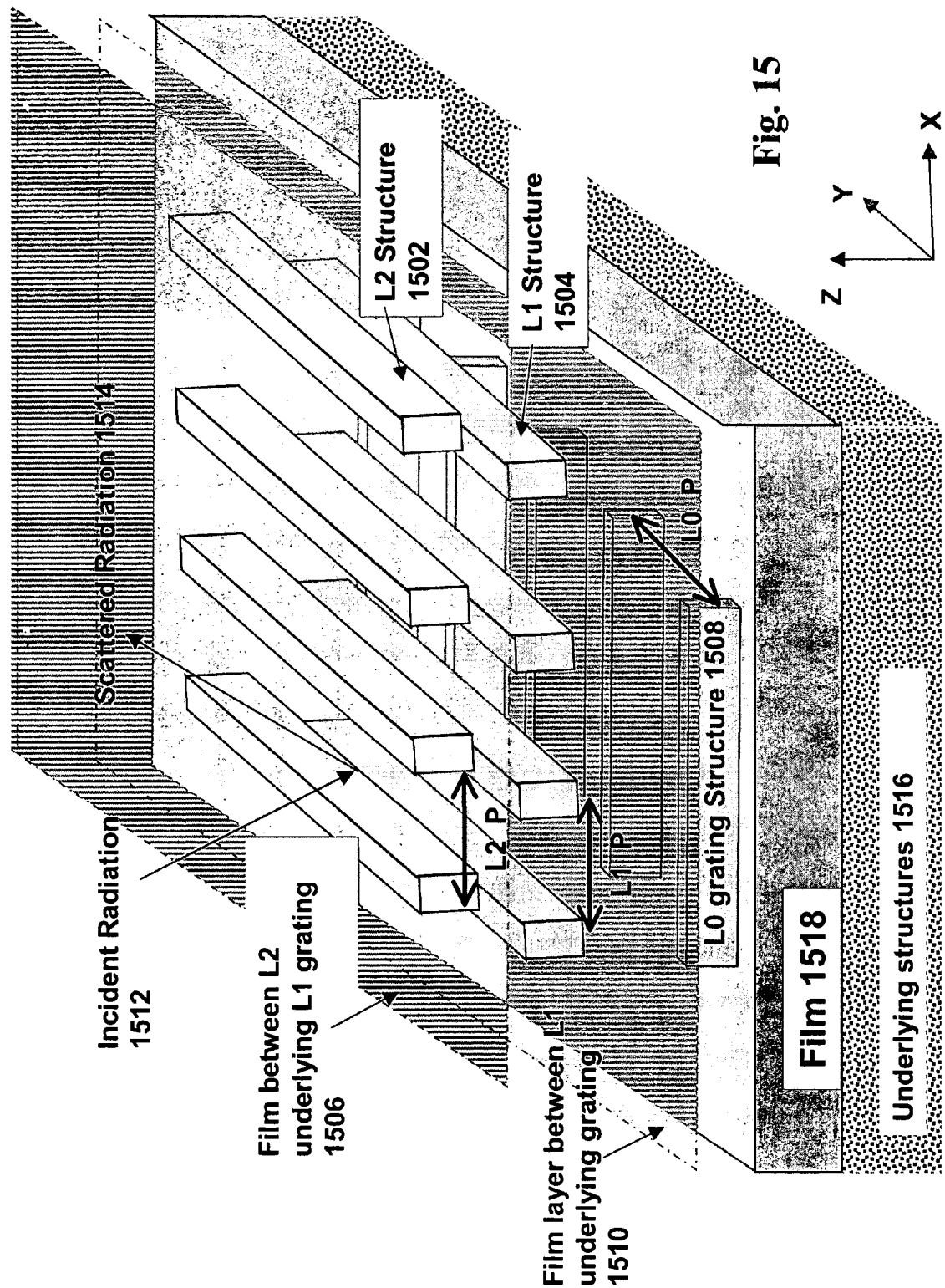
FIG. 15 is a perspective diagrammatic view of overlay line targets with L1 and L2 line elements perpendicular to underlying line grating L0 in accordance with one embodiment of the present invention.

FIG. 15 is a perspective diagrammatic view of overlay line targets with L1 and L2 line elements perpendicular to underlying line grating L0 in accordance with one embodiment of the present invention. As shown, overlay target structures are formed within layer 2 (L2) 1502 and these L2 structures 1502 are positioned over overlay target structures which are formed in layer 1 (L1) 1504. Film 1506 is disposed between L1 structures 1502 and L2 structures 1504. L1 structures are also formed over underlying structures in layer 0 (L0) 1508 with film 1510 disposed between the L1 and L0 structures.

In one implementation, the L0 structures 1508 are perpendicular to the L1 structures 1510 so as to not substantially affect the measurement of structures L1 or L2. That is, when incident radiation 1512 impinges on L1 and L2 structures 1504 and 1502, scattered radiation 1514 is not affected significantly by positioning of the L2/L1 overlay target structure above L0. Additionally, L0 structures 1508 may be formed from one or more material(s) that form a barrier or screen over the underlying layers and structures. For instance, underlying structures 1516 (and film 1518) do not significantly affect the scattered radiation 1514 for at least part of the signal spectrum or at least one of the optical signals. Film 1518 is also typically disposed between L0 structures 1508 and underlying structures 1516.

Although the foregoing invention has been described in some detail for purposes of clarity of understanding, it will be apparent that certain changes and modifications may be practiced within the scope of the appended claims. For example, although the terms wafer or sample were used throughout (e.g., semiconductor), it should be noted that any type of workpieces may be utilized, such as substrates, photomasks, flat panel displays, electro-optic devices, and the like which are associated with other types of manufacturing. The term "stepper" was used throughout as an example to generically represent lithography systems in use or in development in the semiconductor industry and related industries and is not a limitation on the lithography systems which may include steppers, scanner, imprint lithographic systems, electron based lithographic patterning systems, EUV based lithographic patterning systems and the like. Therefore, the described embodiments should be taken as illustrative and not restrictive, and the invention should not be limited to the details given herein but should be defined by the following claims and their full scope of equivalents.

What is claimed is:

1. A method of determining an overlay error between two layers of a multiple layer sample, the method comprising:

for a plurality of periodic targets that each have a first structure formed from a first layer and a second structure formed from a second layer of the sample, employing an optical system to thereby measure an optical signal from each of the periodic targets, wherein there are predefined offsets between the first and second structures; and determining and storing an overlay error between the first and second structures by analyzing the measured optical signals from the periodic targets using a scatterometry overlay technique based on the predefined offsets, wherein the scatterometry overlay technique is a phase based technique that includes representing each of the measured optical signals as a set of periodic functions having a plurality of known parameters and a plurality of unknown parameters that include an unknown overlay error parameter and analyzing the set of periodic functions to solve for the unknown overlay error parameter to thereby determine the overlay error, wherein the number of targets equals the number of unknown parameters, wherein the optical system comprises any one or more of the following apparatus: an imaging reflectometer, an imaging spectroscopic reflectometer, a polarized spectroscopic imaging reflectometer, a scanning reflectometer system, a system with two or more reflectometers capable of parallel data acquisition, a system with two or more spectroscopic reflectometers capable of parallel data acquisition, a system with two or more polarized spectroscopic reflectometers capable of parallel data acquisition, a system with two or more polarized spectroscopic reflectometers capable of serial data acquisition without moving the wafer stage or moving any optical elements or the reflectometer stage, imaging spectrometers, imaging system with wavelength filter, imaging system with long-pass wavelength filter, imaging system with short-pass wavelength filter, imaging system without wavelength filter, interferometric imaging system, imaging ellipsometer, a spectroscopic ellipsometer, a laser ellipsometer having a photoelastic modulator, an imaging spectroscopic ellipsometer, a scanning ellipsometer system, a system with two or more ellipsometers capable of parallel data acquisition, a system with two or more ellipsometers capable of serial data acquisition without moving the wafer stage or moving any optical elements or the ellipsometer stage, a Michelson interferometer, and a Mach-Zehnder interferometer, a Sagnac interferometer, a scanning angle of incidence system, a scanning azimuth angle system, a +/− first order differential reflectometer, and/or a +/− first order differential polarized reflectometer.

2. A method as recited in claim 1, wherein the optical system is a +/− first order differential reflectometer.

3. A method as recited in claim 1, wherein the optical system is a +/− first order differential polarized reflectometer.

4. A method as recited in claim 1, wherein each first structure has a first center of symmetry and each second structure has a second center of symmetry and wherein the first center of symmetry and the second center of symmetry for each target are offset with respect to each other by a selected one of the predefined offsets.

5. A method as recited in claim 1, wherein the overlay error is determined without comparing the measured optical signals to calibration data.

6. A method as recited in claim 1, wherein the optical system is an imaging reflectometer.

7. A method as recited in claim 1, wherein the optical system is an imaging spectroscopic reflectometer.

8. A method as recited in claim 1, wherein the optical system is a scanning reflectometer system.

9. A method as recited in claim 1, wherein the optical system is a system with two or more reflectometers capable of parallel data acquisition.

10. A method as recited in claim 1, wherein the optical system is a system with two or more spectroscopic reflectometers capable of parallel data acquisition.

11. A method as recited in claim 1, wherein the optical system is a system with two or more polarized spectroscopic reflectometers capable of parallel data acquisition.

12. A method as recited in claim 1, wherein the optical system is a system with two or more polarized spectroscopic reflectometers capable of serial data acquisition without moving the wafer stage or moving any optical elements or the reflectometer stage.

13. A method as recited in claim 1, herein the optical system is an imaging spectrometer.

14. A method as recited in claim 1, wherein the optical system is an imaging system with a wavelength filter.

15. A method as recited in claim 1, wherein the optical system is an interferometric imaging system.

16. A method as recited in claim 1, wherein the optical system is an imaging ellipsometer.

17. A method as recited in claim 1, wherein the optical system is an imaging spectroscopic ellipsometer.

18. A method as recited in claim 1, wherein the optical system is a scanning ellipsometer system.

19. A method as recited in claim 1, wherein the optical system is a system with two or more ellipsometers capable of parallel data acquisition.

20. A method as recited in claim 1, wherein the optical system is a system with two or more ellipsometers capable of serial data acquisition without moving the wafer stage or moving any optical elements or the ellipsometer stage.

21. A method as recited in claim 1, wherein the optical system is a Michelson interferometer.

22. A method as recited in claim 1, wherein the optical system is a Mach-Zehnder interferometer.

23. A method as recited in claim 1, wherein the optical system is a Sagnac interferometer.

24. A method as recited in claim 1, wherein the optical system is a scanning angle of incidence system.

25. A method as recited in claim 1, wherein the optical system is a scanning azimuthal angle system.

26. A method as recited in claim 1, wherein the predefined offsets include a +/−F constant and a +/−f0 constant, wherein the F constant equals ½ of a pitch of the targets and f0 constant is outside a region of interest for the determined overlay error and does not cause the uncertainty of the determined overlay error to allow an out-of-specification overlay error to be determined as an in-specification overlay error.

27. A method as recited in claim 1, wherein the optical system is a spectroscopic ellipsometer.

28. A method as recited in claim 1, wherein the optical system is a laser ellipsometer having a photoelastic modulator.

29. A method as recited in claim 1, wherein the number of terms in each set of periodic functions is three and the number of targets is four.

30. A method as recited in claim 27, wherein the spectroscopic ellipsometer comprises at least one reflective focusing element.

31. A method as recited in claim 27, wherein the spectroscopic ellipsometer comprises at least one reflective collection element.

32. A method as recited in claim 28, wherein each first structure has a first center of symmetry and each second structure has a second center of symmetry and wherein the first center of symmetry and the second center of symmetry for each target are offset with respect to each other by a selected one of the predefined offsets.

33. A method as recited in claim 29, wherein the predefined offsets can be represented as Xa, Xb, Xc, and Xd so as to meet the following condition:

Xa−Xc=Xc−Xb=Xb−Xd=Xd−Xa+P=P/4, wherein P is a pitch of each of the four targets.

34. A method of determining an overlay error between two layers of a multiple layer sample, the method comprising:

for a plurality of periodic targets that each have a first structure formed from a first layer and a second structure formed from a second layer of the sample, employing an optical system to thereby measure an optical signal from each of the periodic targets, wherein there are predefined offsets between the first and second structures; and determining an overlay error between the first and second structures by analyzing the measured optical signals from the periodic targets using a scatterometry overlay technique based on the predefined offsets, wherein the optical system is a polarized spectroscopic imaging reflectometer.

35. A method for determining an overlay error between at least two layers in a multiple layer sample, the method comprising:

providing a plurality of periodic targets that each have a first structure in a first layer and a second structure in a second layer, wherein there are predefined offsets between the first and second structures;

adjusting a polarization modulator of an ellipsometer to a plurality of different polarization states;

measuring a plurality of measured signals from the periodic targets for each different polarization state; and using a scatterometry overlay technique to analyze the measured signals of the periodic targets and the predefined offsets of the first and second structures of the periodic targets to thereby determine and store an overlay error between the first and second structures of the periodic targets, wherein, the scatterometry overlay technique is a phase based technique that includes representing each of the measured signals, that was measured for each different polarization state and periodic target, as a set of periodic functions having a plurality of known parameters and a plurality of unknown parameters that include an unknown overlay error parameter and analyzing the set of periodic functions to solve for the unknown overlay error parameter to thereby determine the overlay error, wherein the number of targets equals the number of unknown parameters.

36. A method as recited in claim 35, wherein the polarization modulator is a photoelastic modulator (PEM).

37. A method as recited in claim 35, wherein the ellipsometer includes a polarizer in an incident path and an analyzer in an output path, wherein the polarization modulator is contained in the polarizer.

38. A method as recited in claim 35, wherein the ellipsometer includes a polarizer in an incident path and an analyzer in an output path, wherein the polarization modulator is contained in the analyzer.

39. A method as recited in claim 35, wherein the ellipsometer includes a polarizer in an incident path and an analyzer in an output path, wherein the polarization modulator is contained in both the polarizer and the analyzer.

40. A method as recited in claim 35, wherein each first structure has a first center of symmetry and each second structure has a second center of symmetry and wherein the first center of symmetry and the second center of symmetry for each target are offset with respect to each other by a selected one of the predefined offsets.

41. A method as recited in claim 35, wherein the overlay error is determined without comparing the measured optical signals to calibration data.

42. A method as recited in claim 35, wherein the number of terms in each set of periodic functions is three and the number of targets is four.

43. A method as recited in claim 35, wherein the predefined offsets include a +/−F constant and a +/−f0 constant, wherein the F constant equals ½ of a pitch of the targets and f0 constant is outside a region of interest for the determined overlay error and does not cause the uncertainty of the determined overlay error to allow an out-of specification overlay error to be determined as an in-specification overlay error.

44. A method as recited in claim 42, wherein the predefined offsets can be represented as Xa, Xb, Xc, and Xd so as to meet the following condition:

$Xa-Xc=Xc-Xb=Xb-Xd=Xd-Xa+P=P/4$, wherein P is a pitch of each of the four targets.

* * * * *

UNITED STATES PATENT AND TRADEMARK OFFICE
CERTIFICATE OF CORRECTION

PATENT NO.         : 7,379,183 B2                                    Page 1 of 1
APPLICATION NO. : 10/785731
DATED              : May 27, 2008
INVENTOR(S)        : Mieher et al.

It is certified that error appears in the above-identified patent and that said Letters Patent is hereby corrected as shown below:

In the Claims:

1. In line 1 of claim 13 (column 53, line 26) change "herein" to --wherein--.

2. In line 3 of claim 26 (column 53, line 57) change "1/2" to --1/4--.

3. In line 3 of claim 43 (column 56, line 7) change "1/2" to --1/4--.

Signed and Sealed this

Thirtieth Day of September, 2008

JON W. DUDAS
*Director of the United States Patent and Trademark Office*